US011732271B2

(12) United States Patent
Steuernagel et al.

(10) Patent No.: US 11,732,271 B2
(45) Date of Patent: Aug. 22, 2023

(54) STEM RUST RESISTANCE GENES AND METHODS OF USE

(71) Applicant: The Sainsbury Laboratory, Norwich (GB)

(72) Inventors: Burkhard Steuernagel, Norwich (GB); Sanu Arora, Norwich (GB); Brande Wulff, Norwich (GB)

(73) Assignee: The Sainsbury Laboratory, Norwich (GB)

( * ) Notice: Subject to any disclaimer, the term of this patent is extended or adjusted under 35 U.S.C. 154(b) by 0 days.

(21) Appl. No.: 16/960,618

(22) PCT Filed: Jan. 14, 2019

(86) PCT No.: PCT/US2019/013430
§ 371 (c)(1),
(2) Date: Jul. 8, 2020

(87) PCT Pub. No.: WO2019/140351
PCT Pub. Date: Jul. 18, 2019

(65) Prior Publication Data

US 2020/0362367 A1 Nov. 19, 2020

Related U.S. Application Data

(60) Provisional application No. 62/616,553, filed on Jan. 12, 2018.

(51) Int. Cl.
*C12N 15/82* (2006.01)
*C07K 14/415* (2006.01)
*C12Q 1/6895* (2018.01)

(52) U.S. Cl.
CPC ........ *C12N 15/8282* (2013.01); *C07K 14/415* (2013.01); *C12Q 1/6895* (2013.01); *C12Q 2600/13* (2013.01)

(58) Field of Classification Search
None
See application file for complete search history.

(56) References Cited

FOREIGN PATENT DOCUMENTS

WO 2014194371 A1 12/2014

OTHER PUBLICATIONS

Periyannan et al. "The Gene Sr33, an Ortholog of Barley Mla Genes, Encodes Resistance to Wheat Stem Rust Race Ug99". Science. 341(6147):786-788. (Year: 2013).*
Periyannan et al. "The Gene Sr33, an Ortholog of Barley Mla Genes, Encodes Resistance to Wheat Stem Rust Race Ug99". 341(6147):786-788 (Year: 2013).*
Gen Bank accession AGQ17378 (Year: 2013).*
Gen Bank accession KF031287 (Year: 2013) (Year: 2013).*
International Search Report and Written Opinion of the International Searching Authority dated Oct. 4, 2019 in PCT/US02019/013430.
Database UniProt [Online] Oct. 16, 2013 (Oct. 16, 2013), "Subname: Full=RGA1a {ECO:0000313:EMBL:AGQ17370.1} XP002789997" retrieved from EBI accession No. S5DIG5 sequence.
Database UniProt [Online] Oct. 16, 2013 (Oct. 16, 2013), "Subname: Full=RGA1a {ECO:0000313:EMBL:AGQ17378.1} XP002789998" retrieved from EBI accession No. S5DIR7 sequence.
Database UniProt [Online] May 29, 2013 (May 29, 2013), "Subname: Full=Disease resistance protein RPP13 {ECO:0000313:EnsemblPlants: EMT28227} XP002789999" retrieved from EBI accession No. UniProt: M8CLG2 sequence.
S. Periyannan et al: "The Gene Sr33, an Ortholog of Barely Mla Genes, Encodes Resistance to Wheat Stem Rust Race Ug99," Science, Aug. 16, 2013, pp. 786-788, vol. 341 No. 6147.
Olsen, Eric L., et al, "Simultaneous transfer, introgression, and genomic localization of genes for resistance to stem rust race TTKSK (Ug99) from *Aegilops tauschitto* wheat," Theoretical and Applied Genetics, Feb. 3, 2013, pp. 1179-1188, vol. 126 No. 5.

* cited by examiner

*Primary Examiner* — Matthew R Keogh
*Assistant Examiner* — David R Byrnes
(74) *Attorney, Agent, or Firm* — Williams Mullen; David M. Saravitz

(57) ABSTRACT

Compositions and methods and for enhancing the resistance of wheat plants to wheat stem rust caused by *Puccinia graminis* f. sp. *tritici* are provided. The compositions comprise nucleic acid molecules encoding resistance (R) gene products and variants thereof and plants, seeds, and plant cells comprising such nucleic acid molecules. The methods for enhancing the resistance of a wheat plant to wheat stem rust comprise introducing a nucleic acid molecule encoding an R gene product into a wheat plant cell. Additionally provided are methods for using the wheat plants in agriculture to limit wheat stem rust.

19 Claims, 2 Drawing Sheets

Specification includes a Sequence Listing.

SEQUENCE LISTING

```
<160> NUMBER OF SEQ ID NOS: 11

<210> SEQ ID NO 1
<211> LENGTH: 7640
<212> TYPE: DNA
<213> ORGANISM: Aegilops tauschii
<220> FEATURE:
<221> NAME/KEY: misc_feature
<222> LOCATION: (591)..(4520)
<223> OTHER INFORMATION: Open reading frame (ORF)

<400> SEQUENCE: 1

gagtgctgcc atccctccct ctcatctcag tcttctccat tgcgctgcct tgttgcctcc      60

gagctcgccc ctgccagctg actgccagag acatttgtgg tatgttactt tcctgtcaga     120

tttgtttcca gcgaaactag caatgcttgg atctaaaagg tgacctctcc aggatggtag     180

tggaatagca acaagtagaa ccatggagtt tccggtcatt attcagagca cgttgcatcg     240

gctagcggcc tggtaaattt ctccctccca tctttcttgc tgttcttatt aatctgctga     300

ttgctagatt ataccaagtt tttattcttc cagatcctcc gccgccgtgt gcccttctca     360

cgcatctggc ctctggtgcc ctggcactgc ttccacttca ttgtcctgct cttttctgct     420

ctgcctatga agcatcaaag gtgaagcatc gaggtgagct tggtccagat ctagatatgt     480

tttagcttgg cgactctcag tttttgagct tggattgcat tcagctcctg acatttatgg     540

atctgcagtt ttccagctga ttggtccaga tagctgctcc tgctgatctc atggaggtcg     600

tcacgggtgc catgggcagc ctgctcccca agctgggcaa gctgctcctg gaggagtaca     660

agctgcacaa gggcgtcaag gaaaatatcg aggacctccg gaaggagctt gagagcatga     720

accttgccct cgtcaagatt gatgaggtgc cgcgggacca gctcgacaga caagacaagc     780

tctgggcaga tgatgtcaga gatctctcct acaagattga ggatgtcgtc gacaagttcc     840

tcatgcacgt cgaccgcatt cagcctgacg acaccaccaa tggattcaag gggctcatga     900

agaggacggc cgagttgttc aagaaaggca aggatcggaa tcggataggg cacgcgatga     960

agggcatcca ggaggaactt cagaaggtgg ctgctaggcg tgacaggaac aaggtcgacg    1020
```

-continued

```
gtatggctcc taatactagg gaagcagttg ttatcgatcc tcgtctccgt gctctgtaca   1080
cagaagcgac agagctggtt ggcatctacg ggaagaggga tcaggacctc atgagtttgc   1140
tctccctgga gggcggcgat gcctctaaca agagactgaa gaaggtctcc attgttggat   1200
ttggtggatt gggcaagacc actcttgcta gagcagtata caacaagatt aaaggtgttt   1260
tcgattgtcg ggcatttgtc cccgtcggcc ggaaccccaa catcaagaag gtttttaggg   1320
atatcctcat tgatctcggc aactctaact cagatcttgc attattggat gaaaggcagc   1380
ttatcaacaa gcttcatgaa ttcctcgaga acaagaggta tgcgttactt ccagctgaaa   1440
caactatact ttgatatgtt cgtttctatg ctagctatcc aacactatta tgagtttatg   1500
ataaatacat tgtaaccatc acagagaagg ctggttcaga ataatttttc atttaggtca   1560
gtttcaagac tgtataagca tatatgtttg atcctcctct cctctatctg aataagtagt   1620
aaactacttc tcattgcatt agttgcggtg gcttaaattt aatgccattg gtctaggaaa   1680
tccatctcag catttataca tttcatcaga gatataagta atgagcataa taagagttgt   1740
actggataat acaccaaaat gtaaaggaaa gaactcactt agttctttct ttatcctaac   1800
ccaccccatt aaaacaaaga tcaaatggtg catcgtgcac caaaggctgc ccttttctc    1860
ttaatacacc aagaagttaa atttgctctt tgatatcaca ttctatttcc ccttttcgcc   1920
ttgtttagaa acttactatc agcagaatat actcgaaagg gaaatgtcat gtaaaatttg   1980
agtctccggg agttttatca gcggccatac agtatattgg tgggcaaatc agtgctccga   2040
tctttccaat agatctacct aaccattgta atatttgaaa tgttgtattc catccgatcc   2100
aaaataagtg tcgtggtttt agttcaaacg cttattttgg atcagatgga gtaacaaatt   2160
aatcgtactt ctatctatgt cgttgatgca acaatttgct cttcgtgttt tactcccttg   2220
aatcttaaat ttgtattcat tttattcatc atctgactgg cagtgcataa tgcacagttc   2280
ttaatatcag attatcgaga ttgagacgcc tgattcttat tagtttgttt ctgaatatgt   2340
gcacttatag atgtgtagtt ccacccacat attcttatgg ccctaagctt tgtgatgtgt   2400
ataaacctta cactgatact ctgaactaat gtaggtatct ggtcataatt gatgatatat   2460
gggatgaaaa attgtgggaa tacatcaact tggctttctc cgacaggaat aatctaggca   2520
gtcggctaat caccacaacc cgcattgtca gtgtctccaa ttcatgttgc tcgtcggcta   2580
atgattcaat ttatcaaatg aaacctcttt ctactgatga ttccagaagg ctcttccata   2640
agagaatatt tcccgacaag agtgcatgtc caaatgaatt tgaacaagtg tctaatgata   2700
tattgaaaaa atgtggtgga gtaccactag ccatcattac tattgctagt gctttggcca   2760
gtggccagca ggtgaaacca aagcgtgagt gggatattct gctccagtcc cttggctctg   2820
gactaacaga agataacagt ttagaggaga tgcgtagaat actctctttc agctattata   2880
atctaccata tgatctaaaa acctgtctat tgtacctatg tatatatcca gaagatcacg   2940
agattaatag agataaactg atatggaagt gggtggccga aggatttgtc ctccatggaa   3000
atcaaggaac tagcctgttt ttgctcggat taaattactt caacgaactc atcaatagaa   3060
gtatgatcca gccaatatat gatcctctcg gccaggtata tgcttgccgt gtacatgata   3120
tggttctgga ccttatctgc aacttgtcac atgaagcaaa gtttgttaat gtattcgatg   3180
gcactgggaa tatcatgtct tcacaaagta atgttcgtcg tttgtccctt cagaataaaa   3240
tggaagatca tcaagccaag cctctcacaa atatcatgag tatgtcacga gtgaggtcaa   3300
ttactatctt tccacctgct gttagtatca tgccagctct gtcaaggttt gaagttctgc   3360
gtgtacttga tatgtcggac tgtaaccttg ggaaagtag cagcctgcag cctaacctca    3420
```

agggtgttgg acacttaatt cacctaaggt acctaggtct atcaggtacc ggaattagta 3480
aactcccggc tgagatagga accctgcagt ttctggaggt gttggatctt ggatacaatc 3540
atgagctaga tgaattgccg tccactcttt ttaaattgag aaggttaatc tacctaaatg 3600
ttcggttcta taaggtggtt ccaactcctg gtgtgttgca gaatctgaca tccatagaag 3660
tgttgagggg gctcttggtc tctctgaaca tcattgcaca agagcttggc aacctggcaa 3720
ggctgaggga gcttgagatt cgcttcaagg atggtagttt ggatttgtat gaaggtttcg 3780
tgaagtctct gtgcaaccta catcatatcg aaagcctaag tattagttgc aattccaaag 3840
aaacatcttt tgaactgatg gatctcttgg gagaacgctg ggtgcctcct gtacatctcc 3900
gcgaatttgt gtcatacatc cccagccaaa tctctgcact gcgagggtgg atagagagag 3960
acccctcgca tctctcgaac ctctccgagt taatcctcac gtcagtgaag gaggtgcagc 4020
aggaggacgt ggaaatcatt ggggggttgc tgtcccttcg caatctctgg ataacgagca 4080
cccaccaaac acagcggctg ctagtcatcc gtgcagatgg gttccgctgt atgctaaact 4140
ttgagttgaa ttgtggatca gccgcacaaa taatgtttga atcaggagct ttgccgaggg 4200
cggaaagagt tgagttcagt ctcggcgtgc gggtggcgaa agaggatggt aaccgtggtt 4260
tcaacttggg cctgcagggg aacctgctct cccttcggcg tggtgtccgg atttggatgt 4320
attgtggtgg agcgagggtt ggggaggcca aggaagcgga ggctgcggtg aggcacgccc 4380
tcgacgccca tcccagccat cccctgattt tgattgagat gaggccgcgt atacaagaag 4440
gtactcatgt cgcacctaac tactcacgct caactcccat cccaatcatc cccgattacg 4500
tatatgtttt tttcgaatga tggactgacc ttattactct ctgcattgat tttgatctct 4560
gaatctacca agatgctcat gatgacgatt tgtgtgagga cgaggaggag aactgatttc 4620
tgatccagag cgactcacaa tattgcatca gatgtgctct cgggtatgta acagatattt 4680
gcctgttatg ttttccatct tttatttgcc tgttatgttc gcctgctata acggctgtat 4740
ggaaattaga aacagattaa tgtatttaca aaaattgcta gacataagta tctgaccaga 4800
aaactgaact tgcccgatct gttttatggc aagggctgat gaaagataag aattatttta 4860
tgcaaatttg tagaaggata gttagtaatg gggaatttgg gatagaacta gattttggga 4920
agatttatgg acagggggtg ctgtttttgg tgaccagtac tccaggttat acaacttatc 4980
aatatataag catatctctg tagctagaat gctgcacgct aatttcactg ctctaaaatt 5040
tagagggggt ctgtatggtg aaacggctga gctatcgtat cgattcttgc tgatcgtcaa 5100
ggttagtctt gaggaatgag caagattcat gtagatgatc ccataaaaaa ggttaatgta 5160
aatggctttt agagaagaat gttgtggtta gcattcacca ctatttctgt tgattcagaa 5220
atgagcaaga tcatagtatt tttgtggtta gcattcagaa attatcggca cagttaatct 5280
gaagcgtcga ggtagtgtgg tataggaaag tgtcttttgt ataccacact acctcgacgc 5340
ttcagattag catggaggga ctttgtgctt gagtgatgaa tttcagggta aaggtaggaa 5400
tatggtttct gctagggtag tggctattat ttggtctata tggaaactga ggaatcataa 5460
ttgcttgaaa aatattttcc ctatcgatat tagatgtttt attgggctat cttacagaga 5520
agaattgcac gatatgcagg tagcaggggc gtgggacggt gggggttact gctggtggca 5580
acggagatga atgtttccca aacattttgg gtgggcgctc gccgtgcaaa ggtttcgaac 5640
attctggagg ttgtgtgatg agcttctttt aaatggcact cagcttgcag aaagagatat 5700
tccttggttt tgtaacgaat aagtaaggtg ttggggcgaa ttgatcctta caaggatagc 5760

-continued

```
tttgctttgc ttcagttgag ggtcattgtt gctcctctgt tttgcatgtt gttgttacat   5820

gggagggcta gcccatgaca tgctggtgta ttttgttttt taagctgagc cggacaaacc   5880

tatgggtgta ttatcagttt cctgatgaat gaaatggggg gctcacctga gctccttaat   5940

ttgaataaaa actgcggttc actgttggga tttgttactt gaaaaatatt tacaagttct   6000

accaacatgt ctctgttaca gacaaatgga aagcgtgctt ccaactaaca agcatgtgta   6060

gcccactgta gcaaattatt ttcgtatttt tgaaagtgtc gtcgcaaagc caattgaagc   6120

ctaaattcga cagtggagga aagggcctag aacgaaaagg gccatatatg tttgtacaga   6180

aagtggcaga gctacaaaga aaagatggag agcacaaatg agagttccag ggcttccatt   6240

tccacagtaa aggtatttct tgactatagt tgtgcttaga caagagctaa tgggggagtg   6300

aaactctatg gtagttaaca ataacataag ccgatgaatg gtccactaac taacgatcct   6360

ttagttccta atgtctctca gtccgttcag tccgtaatgc ttacttaacc ttcttatgtt   6420

caggactagc tctgcttttt tctccactgt cacgagtatt tgaatgcgat ggaaggtgtt   6480

ctaactagga gatcttgaga gaagatggag cggtatatat gtgcacacga cggaaccagt   6540

atgagtgttc acagctagaa gttattgggt aagtactatt ttacattgac gccacgtctt   6600

tatattttgt aatggtttaa gatagtaatt tggcaatggc aaagcatata caatttttac   6660

cattaatgat gccacatata tctagattat agaataataa ctacgaccca tgaataaaaa   6720

atttaaagtt ttgacaccga aatatattag actgtatatc ttgtagtgta cactagaaga   6780

tgcattttgt aggagcgcgg acatttaact acccatgcat cttactcaag tcggttgttt   6840

atttattgta accccgatgg tcaagtctgt tcgacacaaa caaaaatagt gaggaaaggg   6900

cctagaacga aaagggctat atatgtttgt acagaaagtg gcagagctac aaagaaaaga   6960

tggagagcac aaaaacttca aattctgaac catatgtact attgagtgaa ttatatattt   7020

attatgctac caaattggaa actattgtta aaccgtgagc tagcaacaat caatgccttt   7080

gttgtgaact tgtataaact ataaaggtgg cctttgttgt gaaccagtaa aatgcaaaga   7140

acaatggctt tccatggtat aaactataaa acaacaagat ttcggtgtgg attatttatg   7200

ctaaagtcca tagatgatga cgtaagtgaa atttagggga agaaatttgg gaagattcag   7260

agaaatttac ctatacagct tgcagggggt gcatgcagat tcagagaagg acctcatcag   7320

gttggctcgc cgctgctagc tacgtcgcct cgcggagtca tggtgggagc actaggcggc   7380

tgatgtgtgc aactgtgccg gtgtgccgga agccggccac cgcgatggcc ggcggctgct   7440

gtgtgcctgt gtcgcggctg ctccgcttct caatgttgcg ttacgtgcct tcgttgtttt   7500

ctctgagaaa cagtgctgga taatcacagt gctgcgactt tgatgtgagc ttcgctgggc   7560

tgaggtgtgc gttgtacttg ctcaatgccg gtcagcagtt gtgggctggg ctcaacgtaa   7620

atttatttct tgctccaaca                                               7640
```

<210> SEQ ID NO 2
<211> LENGTH: 9967
<212> TYPE: DNA
<213> ORGANISM: Aegilops tauschii
<220> FEATURE:
<221> NAME/KEY: misc_feature
<222> LOCATION: (2918)..(6847)
<223> OTHER INFORMATION: Open reading frame (ORF)

<400> SEQUENCE: 2

```
aagtgggggg actattcaac caactcgttc attagaaata gagattgtta cagtttagcg     60

tgtgtgcatg atcgctcagt tttgcaagca aggtttcagg ttctgaactt ccaaaccatg    120
```

-continued

```
acttaagttc tatttccatt cactgaactg gttatattgg gggtctgtgg tggggatttg    180
ttggttcttc acgttcatga ttcttgtgct accttcaaat caatatggtg cagcattttg    240
tgttctgatg cttgctgccc aaaaattctt ttgatatttt ataaaaaaaa gtcctaaact    300
agtgaccatt gttttttgcc tcatgacgtg acctcagatg tccctctcaa tatttagata    360
ggcaacctaa tgcatgagct ctgatgttcc gttgaacttt ttatgcgagt ataacattag    420
atcacgtgtg ttccaaaacg ttcgagaatt ttttgacctt tttgcaactt ctattctttt    480
tcgattcagg tgcactggat ccgagatcca ttgggtattt tcggtatcga ttgcttttga    540
gtactgcata tgaggaaatt taccacctgg caaatgtccg catgaaggag acagaggggt    600
aatgcatgat gtggactgac caacctactg agagtgattc agagaaatgg gaggagtaaa    660
atgcaatgaa gcaatggctg gtggacggac catatatata cagtagtatg taattatttt    720
ctctgaatcc ctgtgtctct gtgacccact caataaacac atcagccaaa agcaatactg    780
ttcggaggta tcgtgggggc tctgtaatct ctgtgaccca ctcaataaac agatcggcca    840
aaagcagtgc tactggtaat ttcctctctt gactgttgtt gttggtcttc ctcggcctcc    900
actgaaactc tgtgttcact ggtaaagttt agcatatgtt catgatcgct caattttgta    960
ggcgaggctt caggttctgt tacagtttaa gtatgctcat gaactgaaac tatgctttcc   1020
ctagtactag tacccaaagg cattcagtat tcacgaccaa accgaagttt tcaaactgaa   1080
cggagggatt caattattca ccggttgcaa agatgaacgc tagtgaggaa aattaatagt   1140
gtcattgcct gataaatgca tgaaggagag agagatggta aatgaccggc aggcgcatga   1200
gggacctaca attattgtct ctgaatgacc cactgaacag ttacatgtgc caaaagcagt   1260
acgtactatt cagaggcatc gtgggggctc tgtatctctt gacttgctgt tgttggtctt   1320
cctctgtatc tcagtcctca tctccaccac tgacagagtc ctcttctccg ttgcgctgcc   1380
tggaataagg tcgatcctcc tcgttgtttg gtgatctcct ccaacctccg agctcgcccc   1440
tgccaactga ctgccagagg cctttgacac ccgtggaggt atatttcctg tcgatttctt   1500
tccagctgaa gtaaaaagta cgcttggatc aaaaaactta cttctcctgc ttcactgctt   1560
gcttgggagt ctgatcgatt tgtgttggtt gaatcatttg gggtggcagt ggaacagcaa   1620
gcaagaacca tggagtttcc gatcattatt cagagcagca cgcatcgaat ccactgaccc   1680
ggttagcggc ctggtaactt tgtctcatct ttcttgctac tgtaatatat ttcacatcca   1740
taccttcttg ttaatctgct gaccctccct tccagatcga gagagagagc gccccttcca   1800
actcacgcct gtgctgtgga ggtatatttc cagtctattt ttccaacctc gttgcatgaa   1860
gcttggatct aaaaaaggac ttctcctgcg cgcgtggttg gcagtgaaat agcaagaaga   1920
tgaactatcg agtttccagt cgttcagagc atgatgcatc aaatccactg aaatcttttt   1980
tgtctcatct tttttgctat tctgctctac tgaaattttt gacatccaca ccttctagtt   2040
aatctgctga tttgctagat tataaattct tgttcctctt tgcagttggt aataattgaa   2100
tcactccgtc ctgtttggta gaggagagag gggtaaatgc atgaagcatg gcagatggac   2160
tgatcgtata cagtacaagt aattattttc tctgaatccc tgtctctctg tgacccactc   2220
actcaataaa cacatcagcc aaaagcgcta ctgctcagag gtatcaatca ttatctctct   2280
tgactgctgt tattggtctt cctctgctag taattattgt atccactgag tgctgccatc   2340
cctccctctc atctcagtct tctccattgc gctgccttgt tgcctccgag ctcgcccctg   2400
ccagctgact gccagagaca tttgtggtat gttactttcc tgtcagattt gtttccagcg   2460
```

-continued

```
aaactagcaa tgcttggatc taaaaggtga cctctccagg atggtagtgg aatagcaaca   2520
agtagaacca tggagtttcc ggtcattatt cagagcacgt tgcatcggct agcggcctgg   2580
taaatttctc cctcccatct ttcttgctgt tcttattaat ctgctgattg ctagattata   2640
ccaagttttt attcttccag atcctccgcc gccgtgtgcc cttctcacgc atctggcctc   2700
tggtgccctg gcactgcttc cacttcattg tcctgctctt ttctgctctg cctatgaagc   2760
atcaaaggtg aagcatcgag gtgagcttgg tccagatcta gatatgtttt agcttggcga   2820
ctctcagttt ttgagcttgg attgcattca gctcctgaca tttatggatc tgcagttttc   2880
cagctgattg gtccagatag ctgctcctgc tgatctcatg gaggtcgtca cgggtgccat   2940
gggcagcctg ctccccaagc tgggcaagct gctcctggag gagtacaagc tgcacaaggg   3000
cgtcaaggaa aatatcgagg acctccggaa ggagcttgag agcatgaacc ttgccctcgt   3060
caagattgat gaggtgccgc gggaccagct cgacagacaa gacaagctct gggcagatga   3120
tgtcagagat ctctcctaca agattgagga tgtcgtcgac aagttcctca tgcacgtcga   3180
ccgcattcag cctgacgaca ccaccaatgg attcaagggg ctcatgaaga ggacggccga   3240
gttgttcaag aaaggcaagg atcggaatcg gatagggcac gcgatgaagg gcatccagga   3300
ggaacttcag aaggtggctg ctaggcgtga caggaacaag gtcgacggta tggctcctaa   3360
tactagggaa gcagttgtta tcgatcctcg tctccgtgct ctgtacacag aagcgacaga   3420
gctggttggc atctacggga agagggatca ggacctcatg agtttgctct ccctggaggg   3480
cggcgatgcc tctaacaaga gactgaagaa ggtctccatt gttggatttg gtggattggg   3540
caagaccact cttgctagag cagtatacaa caagattaaa ggtgttttcg attgtcgggc   3600
atttgtcccc gtcggccgga accccaacat caagaaggtt tttagggata tcctcattga   3660
tctcggcaac tctaactcag atcttgcatt attggatgaa aggcagctta tcaacaagct   3720
tcatgaattc ctcgagaaca agaggtatgc gttacttcca gctgaaacaa ctatactttg   3780
atatgttcgt ttctatgcta gctatccaac actattatga gtttatgata aatacattgt   3840
aaccatcaca gagaaggctg gttcagaata atttttcatt taggtcagtt tcaagactgt   3900
ataagcatat atgtttgatc ctcctctcct ctatctgaat aagtagtaaa ctacttctca   3960
ttgcattagt tgcggtggct taaatttaat gccattggtc taggaaatcc atctcagcat   4020
ttatacattt catcagagat ataagtaatg agcataataa gagttgtact ggataataca   4080
ccaaaatgta aaggaaagaa ctcacttagt tctttcttta tcctaaccca ccccattaaa   4140
acaaagatca aatggtgcat cgtgcaccaa aggctgccct ttttctctta atacaccaag   4200
aagttaaatt tgctctttga tatcacattc tatttcccct tttcgccttg tttagaaact   4260
tactatcagc agaatatact cgaaagggaa atgtcatgta aaatttgagt ctccgggagt   4320
tttatcagcg gccatacagt atattggtgg gcaaatcagt gctccgatct ttccaataga   4380
tctacctaac cattgtaata tttgaaatgt tgtattccat ccgatccaaa ataagtgtcg   4440
tggttttagt tcaaacgctt attttggatc agatggagta acaaattaat cgtacttcta   4500
tctatgtcgt tgatgcaaca atttgctctt cgtgttttac tcccttgaat cttaaatttg   4560
tattcatttt attcatcatc tgactggcag tgcataatgc acagttctta atatcagatt   4620
atcgagattg agacgcctga ttcttattag tttgtttctg aatatgtgca cttatagatg   4680
tgtagttcca cccacatatt cttatggccc taagctttgt gatgtgtata aaccttacac   4740
tgatactctg aactaatgta ggtatctggt cataattgat gatatatggg atgaaaaatt   4800
gtgggaatac atcaacttgg ctttctccga caggaataat ctaggcagtc ggctaatcac   4860
```

```
cacaacccgc attgtcagtg tctccaattc atgttgctcg tcggctaatg attcaattta   4920
tcaaatgaaa cctctttcta ctgatgattc cagaaggctc ttccataaga gaatatttcc   4980
cgacaagagt gcatgtccaa atgaatttga acaagtgtct aatgatatat tgaaaaaatg   5040
tggtggagta ccactagcca tcattactat tgctagtgct ttggccagtg gccagcaggt   5100
gaaaccaaag cgtgagtggg atattctgct ccagtccctt ggctctggac taacagaaga   5160
taacagttta gaggagatgc gtagaatact ctctttcagc tattataatc taccatatga   5220
tctaaaaacc tgtctattgt acctatgtat atatccagaa gatcacgaga ttaatagaga   5280
taaactgata tggaagtggg tggccgaagg atttgtcctc catggaaatc aaggaactag   5340
cctgtttttg ctcggattaa attacttcaa cgaactcatc aatagaagta tgatccagcc   5400
aatatatgat cctctcggcc aggtatatgc ttgccgtgta catgatatgg ttctggacct   5460
tatctgcaac ttgtcacatg aagcaaagtt tgttaatgta ttcgatggca ctgggaatat   5520
catgtcttca caaagtaatg ttcgtcgttt gtcccttcag aataaaatgg aagatcatca   5580
agccaagcct ctcacaaata tcatgagtat gtcacgagtg aggtcaatta ctatctttcc   5640
acctgctgtt agtatcatgc cagctctgtc aaggtttgaa gttctgcgtg tacttgatat   5700
gtcggactgt aaccttgggg aaagtagcag cctgcagcct aacctcaagg gtgttggaca   5760
cttaattcac ctaaggtacc taggtctatc aggtaccgga attagtaaac tcccggctga   5820
gataggaacc ctgcagtttc tggaggtgtt ggatcttgga tacaatcatg agctagatga   5880
attgccgtcc actcttttta aattgagaag gttaatctac ctaaatgttc ggttctataa   5940
ggtggttcca actcctggtg tgttgcagaa tctgacatcc atagaagtgt tgaggggcct   6000
cttggtctct ctgaacatca ttgcacaaga gcttggcaac ctggcaaggc tgagggagct   6060
tgagattcgc ttcaaggatg gtagtttgga tttgtatgaa ggtttcgtga agtctctgtg   6120
caacctacat catatcgaaa gcctaagtat tagttgcaat tccaaagaaa catcttttga   6180
actgatggat ctcttgggag aacgctgggt gcctcctgta catctccgcg aatttgtgtc   6240
atacatcccc agccaaatct ctgcactgcg agggtggata gagagagacc cctcgcatct   6300
ctcgaacctc tccgagttaa tcctcacgtc agtgaaggag gtgcagcagg aggacgtgga   6360
aatcattggg gggttgctgt cccttcgcaa tctctggata acgagcaccc accaaacaca   6420
gcggctgcta gtcatccgtg cagatgggtt ccgctgtatg ctaaactttg agttgaattg   6480
tggatcagcc gcacaaataa tgtttgaatc aggagctttg ccgagggcgg aaagagttga   6540
gttcagtctc ggcgtgcggg tggcgaaaga ggatggtaac cgtggtttca acttgggcct   6600
gcaggggaac ctgctctccc ttcggcgtgg tgtccggatt tggatgtatt gtggtggagc   6660
gagggttggg gaggccaagg aagcggaggc tgcggtgagg cacgccctcg acgcccatcc   6720
cagccatccc ctgattttga ttgagatgag gccgcgtata caagaaggta ctcatgtcgc   6780
acctaactac tcacgctcaa ctcccatccc aatcatcccc gattacgtat atgttttttt   6840
cgaatgatgg actgacctta ttactctctg cattgatttt gatctctgaa tctaccaaga   6900
tgctcatgat gacgatttgt gtgaggacga ggaggagaac tgatttctga tccagagcga   6960
ctcacaatat tgcatcagat gtgctctcgg gtatgtaaca gatatttgcc tgttatgttt   7020
tccatctttt atttgcctgt tatgttcgcc tgctataacg gctgtatgga aattagaaac   7080
agattaatgt atttacaaaa attgctagac ataagtatct gaccagaaaa ctgaacttgc   7140
ccgatctgtt ttatggcaag ggctgatgaa agataagaat tattttatgc aaatttgtag   7200
```

-continued

```
aaggatagtt agtaatgggg aatttgggat agaactagat tttgggaaga tttatggaca   7260
gggggtgctg tttttggtga ccagtactcc aggttataca acttatcaat atataagcat   7320
atctctgtag ctagaatgct gcacgctaat ttcactgctc taaaatttag agggggtctg   7380
tatggtgaaa cggctgagct atcgtatcga ttcttgctga tcgtcaaggt tagtcttgag   7440
gaatgagcaa gattcatgta gatgatccca taaaaaaggt taatgtaaat ggcttttaga   7500
gaagaatgtt gtggttagca ttcaccacta tttctgttga ttcagaaatg agcaagatca   7560
tagtattttt gtggttagca ttcagaaatt atcggcacag ttaatctgaa gcgtcgaggt   7620
agtgtggtat aggaaagtgt cttttgtata ccacactacc tcgacgcttc agattagcat   7680
ggagggactt tgtgcttgag tgatgaattt cagggtaaag gtaggaatat ggtttctgct   7740
agggtagtgg ctattatttg gtctatatgg aaactgagga atcataattg cttgaaaaat   7800
attttcccta tcgatattag atgttttatt gggctatctt acagagaaga attgcacgat   7860
atgcaggtag caggggcgtg ggacggtggg ggttactgct ggtggcaacg gagatgaatg   7920
tttcccaaac attttgggtg ggcgctcgcc gtgcaaaggt ttcgaacatt ctggaggttg   7980
tgtgatgagc ttcttttaaa tggcactcag cttgcagaaa gagatattcc ttggttttgt   8040
aacgaataag taaggtgttg gggcgaattg atccttacaa ggatagcttt gctttgcttc   8100
agttgagggt cattgttgct cctctgtttt gcatgttgtt gttacatggg agggctagcc   8160
catgacatgc tggtgtattt tgttttttaa gctgagccgg acaaacctat gggtgtatta   8220
tcagtttcct gatgaatgaa atggggggct cacctgagct ccttaatttg aataaaaact   8280
gcggttcact gttgggattt gttacttgaa aaatatttac aagttctacc aacatgtctc   8340
tgttacagac aaatggaaag cgtgcttcca actaacaagc atgtgtagcc cactgtagca   8400
aattattttc gtatttttga aagtgtcgtc gcaaagccaa ttgaagccta aattcgacag   8460
tggaggaaag ggcctagaac gaaaagggcc atatatgttt gtacagaaag tggcagagct   8520
acaaagaaaa gatggagagc acaaatgaga gttccagggc ttccatttcc acagtaaagg   8580
tatttcttga ctatagttgt gcttagacaa gagctaatgg gggagtgaaa ctctatggta   8640
gttaacaata acataagccg atgaatggtc cactaactaa cgatccttta gttcctaatg   8700
tctctcagtc cgttcagtcc gtaatgctta cttaaccttc ttatgttcag gactagctct   8760
gcttttttct ccactgtcac gagtatttga atgcgatgga aggtgttcta actaggagat   8820
cttgagagaa gatggagcgg tatatatgtg cacacgacgg aaccagtatg agtgttcaca   8880
gctagaagtt attgggtaag tactatttta cattgacgcc acgtctttat attttgtaat   8940
ggtttaagat agtaatttgg caatggcaaa gcatatacaa tttttaccat taatgatgcc   9000
acatatatct agattataga ataataacta cgacccatga ataaaaaatt taaagttttg   9060
acaccgaaat atattagact gtatatcttg tagtgtacac tagaagatgc attttgtagg   9120
agcgcggaca tttaactacc catgcatctt actcaagtcg gttgtttatt tattgtaacc   9180
ccgatggtca agtctgttcg acacaaacaa aaatagtgag gaaagggcct agaacgaaaa   9240
gggctatata tgtttgtaca gaaagtggca gagctacaaa gaaaagatgg agagcacaaa   9300
aacttcaaat tctgaaccat atgtactatt gagtgaatta tatatttatt atgctaccaa   9360
attggaaact attgttaaac cgtgagctag caacaatcaa tgcctttgtt gtgaacttgt   9420
ataaactata aaggtggcct ttgttgtgaa ccagtaaaat gcaaagaaca atggctttcc   9480
atggtataaa ctataaaaca acaagatttc ggtgtggatt atttatgcta aagtccatag   9540
atgatgacgt aagtgaaatt taggggaaga aatttgggaa gattcagaga aatttaccta   9600
```

tacagcttgc agggggtgca tgcagattca gagaaggacc tcatcaggtt ggctcgccgc 9660
tgctagctac gtcgcctcgc ggagtcatgg tgggagcact aggcggctga tgtgtgcaac 9720
tgtgccggtg tgccggaagc cggccaccgc gatggccggc ggctgctgtg tgcctgtgtc 9780
gcggctgctc cgcttctcaa tgttgcgtta cgtgccttcg ttgttttctc tgagaaacag 9840
tgctggataa tcacagtgct gcgactttga tgtgagcttc gctgggctga ggtgtgcgtt 9900
gtacttgctc aatgccggtc agcagttgtg ggctgggctc aacgtaaatt tatttcttgc 9960
tccaaca 9967

<210> SEQ ID NO 3
<211> LENGTH: 2910
<212> TYPE: DNA
<213> ORGANISM: Aegilops tauschii

<400> SEQUENCE: 3
atggaggtcg tcacgggtgc catgggcagc ctgctcccca agctgggcaa gctgctcctg 60
gaggagtaca agctgcacaa gggcgtcaag gaaaatatcg aggacctccg gaaggagctt 120
gagagcatga accttgccct cgtcaagatt gatgaggtgc cgcgggacca gctcgacaga 180
caagacaagc tctgggcaga tgatgtcaga gatctctcct acaagattga ggatgtcgtc 240
gacaagttcc tcatgcacgt cgaccgcatt cagcctgacg acaccaccaa tggattcaag 300
gggctcatga agaggacggc cgagttgttc aagaaaggca aggatcggaa tcggataggg 360
cacgcgatga agggcatcca ggaggaactt cagaaggtgg ctgctaggcg tgacaggaac 420
aaggtcgacg gtatggctcc taatactagg gaagcagttg ttatcgatcc tcgtctccgt 480
gctctgtaca cagaagcgac agagctggtt ggcatctacg ggaagaggga tcaggacctc 540
atgagtttgc tctccctgga gggcggcgat gcctctaaca agagactgaa gaaggtctcc 600
attgttggat ttggtggatt gggcaagacc actcttgcta gagcagtata caacaagatt 660
aaaggtgttt tcgattgtcg ggcatttgtc cccgtcggcc ggaaccccaa catcaagaag 720
gtttttaggg atatcctcat tgatctcggc aactctaact cagatcttgc attattggat 780
gaaaggcagc ttatcaacaa gcttcatgaa ttcctcgaga acaagaggta tctggtcata 840
attgatgata tatgggatga aaaattgtgg gaatacatca acttggcttt ctccgacagg 900
aataatctag gcagtcggct aatcaccaca acccgcattg tcagtgtctc caattcatgt 960
tgctcgtcgg ctaatgattc aatttatcaa atgaaacctc tttctactga tgattccaga 1020
aggctcttcc ataagagaat atttcccgac aagagtgcat gtccaaatga atttgaacaa 1080
gtgtctaatg atatattgaa aaaatgtggt ggagtaccac tagccatcat tactattgct 1140
agtgctttgg ccagtggcca gcaggtgaaa ccaaagcgtg agtgggatat tctgctccag 1200
tcccttggct ctggactaac agaagataac agtttagagg agatgcgtag aatactctct 1260
ttcagctatt ataatctacc atatgatcta aaaacctgtc tattgtacct atgtatatat 1320
ccagaagatc acgagattaa tagagataaa ctgatatgga agtgggtggc cgaaggattt 1380
gtcctccatg gaaatcaagg aactagcctg tttttgctcg gattaaatta cttcaacgaa 1440
ctcatcaata gaagtatgat ccagccaata tatgatcctc tcggccaggt atatgcttgc 1500
cgtgtacatg atatggttct ggaccttatc tgcaacttgt cacatgaagc aaagtttgtt 1560
aatgtattcg atggcactgg gaatatcatg tcttcacaaa gtaatgttcg tcgtttgtcc 1620
cttcagaata aaatggaaga tcatcaagcc aagcctctca caaatatcat gagtatgtca 1680

```
cgagtgaggt caattactat ctttccacct gctgttagta tcatgccagc tctgtcaagg   1740

tttgaagttc tgcgtgtact tgatatgtcg gactgtaacc ttggggaaag tagcagcctg   1800

cagcctaacc tcaagggtgt tggacactta attcacctaa ggtacctagg tctatcaggt   1860

accggaatta gtaaactccc ggctgagata ggaaccctgc agtttctgga ggtgttggat   1920

cttggataca atcatgagct agatgaattg ccgtccactc tttttaaatt gagaaggtta   1980

atctacctaa atgttcggtt ctataaggtg gttccaactc ctggtgtgtt gcagaatctg   2040

acatccatag aagtgttgag gggctcttg gtctctctga acatcattgc acaagagctt   2100

ggcaacctgg caaggctgag ggagcttgag attcgcttca aggatggtag tttggatttg   2160

tatgaaggtt tcgtgaagtc tctgtgcaac ctacatcata tcgaaagcct aagtattagt   2220

tgcaattcca aagaaacatc ttttgaactg atggatctct tgggagaacg ctgggtgcct   2280

cctgtacatc tccgcgaatt tgtgtcatac atccccagcc aaatctctgc actgcgaggg   2340

tggatagaga gagacccctc gcatctctcg aacctctccg agttaatcct cacgtcagtg   2400

aaggaggtgc agcaggagga cgtggaaatc attgggggt tgctgtccct tcgcaatctc   2460

tggataacga gcacccacca aacacagcgg ctgctagtca tccgtgcaga tgggttccgc   2520

tgtatgctaa actttgagtt gaattgtgga tcagccgcac aaataatgtt tgaatcagga   2580

gctttgccga gggcggaaag agttgagttc agtctcggcg tgcgggtggc gaaagaggat   2640

ggtaaccgtg gtttcaactt gggcctgcag gggaacctgc tctcccttcg gcgtggtgtc   2700

cggatttgga tgtattgtgg tggagcgagg gttggggagg ccaaggaagc ggaggctgcg   2760

gtgaggcacg ccctcgacgc ccatcccagc catcccctga ttttgattga gatgaggccg   2820

cgtatacaag aaggtactca tgtcgcacct aactactcac gctcaactcc catcccaatc   2880

atccccgatt acgtatatgt ttttttcgaa                                    2910


<210> SEQ ID NO 4
<211> LENGTH: 970
<212> TYPE: PRT
<213> ORGANISM: Aegilops tauschii

<400> SEQUENCE: 4

Met Glu Val Val Thr Gly Ala Met Gly Ser Leu Leu Pro Lys Leu Gly
1               5                   10                  15

Lys Leu Leu Leu Glu Glu Tyr Lys Leu His Lys Gly Val Lys Glu Asn
            20                  25                  30

Ile Glu Asp Leu Arg Lys Glu Leu Glu Ser Met Asn Leu Ala Leu Val
        35                  40                  45

Lys Ile Asp Glu Val Pro Arg Asp Gln Leu Asp Arg Gln Asp Lys Leu
    50                  55                  60

Trp Ala Asp Asp Val Arg Asp Leu Ser Tyr Lys Ile Glu Asp Val Val
65                  70                  75                  80

Asp Lys Phe Leu Met His Val Asp Arg Ile Gln Pro Asp Asp Thr Thr
                85                  90                  95

Asn Gly Phe Lys Gly Leu Met Lys Arg Thr Ala Glu Leu Phe Lys Lys
            100                 105                 110

Gly Lys Asp Arg Asn Arg Ile Gly His Ala Met Lys Gly Ile Gln Glu
        115                 120                 125

Glu Leu Gln Lys Val Ala Ala Arg Arg Asp Arg Asn Lys Val Asp Gly
    130                 135                 140

Met Ala Pro Asn Thr Arg Glu Ala Val Val Ile Asp Pro Arg Leu Arg
145                 150                 155                 160
```

-continued

```
Ala Leu Tyr Thr Glu Ala Thr Glu Leu Val Gly Ile Tyr Gly Lys Arg
                165                 170                 175

Asp Gln Asp Leu Met Ser Leu Leu Ser Leu Glu Gly Gly Asp Ala Ser
            180                 185                 190

Asn Lys Arg Leu Lys Lys Val Ser Ile Val Gly Phe Gly Gly Leu Gly
        195                 200                 205

Lys Thr Thr Leu Ala Arg Ala Val Tyr Asn Lys Ile Lys Gly Val Phe
    210                 215                 220

Asp Cys Arg Ala Phe Val Pro Val Gly Arg Asn Pro Asn Ile Lys Lys
225                 230                 235                 240

Val Phe Arg Asp Ile Leu Ile Asp Leu Gly Asn Ser Asn Ser Asp Leu
                245                 250                 255

Ala Leu Leu Asp Glu Arg Gln Leu Ile Asn Lys Leu His Glu Phe Leu
            260                 265                 270

Glu Asn Lys Arg Tyr Leu Val Ile Ile Asp Asp Ile Trp Asp Glu Lys
        275                 280                 285

Leu Trp Glu Tyr Ile Asn Leu Ala Phe Ser Asp Arg Asn Asn Leu Gly
    290                 295                 300

Ser Arg Leu Ile Thr Thr Thr Arg Ile Val Ser Val Ser Asn Ser Cys
305                 310                 315                 320

Cys Ser Ser Ala Asn Asp Ser Ile Tyr Gln Met Lys Pro Leu Ser Thr
                325                 330                 335

Asp Asp Ser Arg Arg Leu Phe His Lys Arg Ile Phe Pro Asp Lys Ser
            340                 345                 350

Ala Cys Pro Asn Glu Phe Glu Gln Val Ser Asn Asp Ile Leu Lys Lys
        355                 360                 365

Cys Gly Gly Val Pro Leu Ala Ile Ile Thr Ile Ala Ser Ala Leu Ala
    370                 375                 380

Ser Gly Gln Gln Val Lys Pro Lys Arg Glu Trp Asp Ile Leu Leu Gln
385                 390                 395                 400

Ser Leu Gly Ser Gly Leu Thr Glu Asp Asn Ser Leu Glu Glu Met Arg
                405                 410                 415

Arg Ile Leu Ser Phe Ser Tyr Tyr Asn Leu Pro Tyr Asp Leu Lys Thr
            420                 425                 430

Cys Leu Leu Tyr Leu Cys Ile Tyr Pro Glu Asp His Glu Ile Asn Arg
        435                 440                 445

Asp Lys Leu Ile Trp Lys Trp Val Ala Glu Gly Phe Val Leu His Gly
    450                 455                 460

Asn Gln Gly Thr Ser Leu Phe Leu Leu Gly Leu Asn Tyr Phe Asn Glu
465                 470                 475                 480

Leu Ile Asn Arg Ser Met Ile Gln Pro Ile Tyr Asp Pro Leu Gly Gln
                485                 490                 495

Val Tyr Ala Cys Arg Val His Asp Met Val Leu Asp Leu Ile Cys Asn
            500                 505                 510

Leu Ser His Glu Ala Lys Phe Val Asn Val Phe Asp Gly Thr Gly Asn
        515                 520                 525

Ile Met Ser Ser Gln Ser Asn Val Arg Arg Leu Ser Leu Gln Asn Lys
    530                 535                 540

Met Glu Asp His Gln Ala Lys Pro Leu Thr Asn Ile Met Ser Met Ser
545                 550                 555                 560

Arg Val Arg Ser Ile Thr Ile Phe Pro Pro Ala Val Ser Ile Met Pro
                565                 570                 575
```

```
Ala Leu Ser Arg Phe Glu Val Leu Arg Val Leu Asp Met Ser Asp Cys
            580                 585                 590

Asn Leu Gly Glu Ser Ser Ser Leu Gln Pro Asn Leu Lys Gly Val Gly
        595                 600                 605

His Leu Ile His Leu Arg Tyr Leu Gly Leu Ser Gly Thr Gly Ile Ser
    610                 615                 620

Lys Leu Pro Ala Glu Ile Gly Thr Leu Gln Phe Leu Glu Val Leu Asp
625                 630                 635                 640

Leu Gly Tyr Asn His Glu Leu Asp Glu Leu Pro Ser Thr Leu Phe Lys
                645                 650                 655

Leu Arg Arg Leu Ile Tyr Leu Asn Val Arg Phe Tyr Lys Val Val Pro
            660                 665                 670

Thr Pro Gly Val Leu Gln Asn Leu Thr Ser Ile Glu Val Leu Arg Gly
        675                 680                 685

Leu Leu Val Ser Leu Asn Ile Ile Ala Gln Glu Leu Gly Asn Leu Ala
    690                 695                 700

Arg Leu Arg Glu Leu Glu Ile Arg Phe Lys Asp Gly Ser Leu Asp Leu
705                 710                 715                 720

Tyr Glu Gly Phe Val Lys Ser Leu Cys Asn Leu His His Ile Glu Ser
                725                 730                 735

Leu Ser Ile Ser Cys Asn Ser Lys Glu Thr Ser Phe Glu Leu Met Asp
            740                 745                 750

Leu Leu Gly Glu Arg Trp Val Pro Pro Val His Leu Arg Glu Phe Val
        755                 760                 765

Ser Tyr Ile Pro Ser Gln Ile Ser Ala Leu Arg Gly Trp Ile Glu Arg
    770                 775                 780

Asp Pro Ser His Leu Ser Asn Leu Ser Glu Leu Ile Leu Thr Ser Val
785                 790                 795                 800

Lys Glu Val Gln Gln Glu Asp Val Glu Ile Ile Gly Gly Leu Leu Ser
                805                 810                 815

Leu Arg Asn Leu Trp Ile Thr Ser Thr His Gln Thr Gln Arg Leu Leu
            820                 825                 830

Val Ile Arg Ala Asp Gly Phe Arg Cys Met Leu Asn Phe Glu Leu Asn
        835                 840                 845

Cys Gly Ser Ala Ala Gln Ile Met Phe Glu Ser Gly Ala Leu Pro Arg
    850                 855                 860

Ala Glu Arg Val Glu Phe Ser Leu Gly Val Arg Val Ala Lys Glu Asp
865                 870                 875                 880

Gly Asn Arg Gly Phe Asn Leu Gly Leu Gln Gly Asn Leu Leu Ser Leu
                885                 890                 895

Arg Arg Gly Val Arg Ile Trp Met Tyr Cys Gly Gly Ala Arg Val Gly
            900                 905                 910

Glu Ala Lys Glu Ala Glu Ala Ala Val Arg His Ala Leu Asp Ala His
        915                 920                 925

Pro Ser His Pro Leu Ile Leu Ile Glu Met Arg Pro Arg Ile Gln Glu
    930                 935                 940

Gly Thr His Val Ala Pro Asn Tyr Ser Arg Ser Thr Pro Ile Pro Ile
945                 950                 955                 960

Ile Pro Asp Tyr Val Tyr Val Phe Phe Glu
                965                 970


<210> SEQ ID NO 5
<211> LENGTH: 19250
<212> TYPE: DNA
```

<213> ORGANISM: Artificial Sequence
<220> FEATURE:
<223> OTHER INFORMATION: nucleotide sequence of synthetic vector construct
<220> FEATURE:
<221> NAME/KEY: promoter
<222> LOCATION: (2969)..(5349)
<223> OTHER INFORMATION: Sr33 promoter
<220> FEATURE:
<221> NAME/KEY: misc_feature
<222> LOCATION: (5354)..(9283)
<223> OTHER INFORMATION: SrTA1662 open reading frame (ORF)
<220> FEATURE:
<221> NAME/KEY: terminator
<222> LOCATION: (9288)..(10708)
<223> OTHER INFORMATION: Sr33 terminator

<400> SEQUENCE: 5
tcgacgatct tgctgcgttc ggatattttc gtggagttcc cgccacagac ccggattgaa 60
ggcgagatcc agcaactcgc gccagatcat cctgtgacgg aactttggcg cgtgatgact 120
ggccaggacg tcggccgaaa gagcgacaag cagatcacga ttttcgacag cgtcggattt 180
gcgatcgagg atttttcggc gctgcgctac gtccgcgacc gcgttgaggg atcaagccac 240
agcagcccac tcgaccttct agccgaccca gacgagccaa gggatctttt tggaatgctg 300
ctccgtcgtc aggctttccg acgtttgggt ggttgaacag aagtcattat cgcacggaat 360
gccaagcact cccgagggga accctgtggt tggcatgcac atacataatg gacgaagcgg 420
ataaaccttt tcacgccctt ttaaatatcc gattattcta ataaacgctc ttttctctta 480
ggtttacccg ccaatatatc ctgtcaaaca ctgatagttt aaactgaagg cgggaaacga 540
caatctgatc atgagcggag aattaaggga gtcacgttat gaccccgcc gatgacgcgg 600 gacaagccgt tttacgtttg gaactgacag aaccgcaacg ttgaaggagc cactcagccg 660
cgggtttctg gagtttaatg agctaagcac atacgtcaga aaccattatt gcgcgttcaa 720
aagtcgccta aggtcactat cagctagcaa atatttcttg tcaaaaatgc tccactgacg 780
ttccataaat tcccctcggt atccaattag agtctcatat tcactctcaa tccaaataat 840
ctgcaatggc aattacctta tccgcaactt ctttacctat ttccgcccgg atctgatatc 900
atcgatgaat tccgatctag tcacatagat gacaccgcgc gcgataattt agtcctagtt 960
tgcgcgctat attttgtttt ctatcgcgta ttaaatgtat aattgcgggg actctaatca 1020
taaaaaccca tctcataaat aacgtcatgc attacatgtt aattattaca tgcttaacgt 1080
aatcaacaga aattatatga taatcatcgc aagaccggca acaggattca atcttaagaa 1140
actttattgc caaatgtttg aacgatccga gctctccgga tcccggtcgg catctactct 1200
attcctttgc cctcggacga gtgctggggc gtcggtttcc actatcggcg agtacttcta 1260
cacagccatc ggtccagacg gccgcgcttc tgcgggcgat ttgtgtacgc ccgacagtcc 1320
cggctccgga tcggacgatt gcgtcgcatc gaccctgcgc ccaagctgca tcatcgaaat 1380
tgccgtcaac caagctctga tagagttggt caagaccaat gcggagcata tacgcccgga 1440
gccgcggcga tcctgcaagc tccggatgcc tccgctcgaa gtagcgcgtc tgctgctcca 1500
tacaagccaa ccacggcctc cagaagaaga tgttggcgac ctcgtattgg gaatccccga 1560
acatcgcctc gctccagtca atgaccgctg ttatgcggcc attgtccgtc aggacattgt 1620
tggagccgaa atccgcgtgc acgaggtgcc ggacttcggg gcagtcctcg gcccaaagca 1680
tcagctcatc gagagcctgc gcgacggacg cactgacggt gtcgtccatc acagtttgcc 1740
agtgatacac atggggatca gcaatcgcgc atatgaaatc acgccatgta gtgtattgac 1800

-continued

```
cgattccttg cggtccgaat gggccgaacc cgctcgtctg gctaagatcg gccgcagcga   1860
tcgcatccat ggcctccgcg accggctgca gttatcatca tcatcataga cacacgaaat   1920
aaagtaatca gattatcagt taaagctatg taatatttac accataacca atcaattaaa   1980
aaatagatca gtttaaagaa agatcaaagc tcaaaaaaat aaaaagagaa aagggtccta   2040
accaagaaaa tgaaggagaa aaactagaaa tttacctgca gaacagcggg cagttcggtt   2100
tcaggcaggt cttgcaacgt gacaccctgt gcacggcggg agatgcaata ggtcaggctc   2160
tcgctgaatt ccccaatgtc aagcacttcc ggaatcggga gcgcggccga tgcaaagtgc   2220
cgataaacat aacgatcttt gtagaaacca tcggcgcagc tatttacccg caggacatat   2280
ccacgccctc ctacatcgaa gctgaaagca cgagattctt cgccctccga gagctgcatc   2340
aggtcggaga cgctgtcgaa cttttcgatc agaaacttct cgacagacgt cgcggtgagt   2400
tcaggctttt tcatatcggg gtcgtcctct ccaaatgaaa tgaacttcct tatatagagg   2460
aagggtcttg cgaaggatag tgggattgtg cgtcatccct tacgtcagtg gagatatcac   2520
atcaatccac ttgctttgaa gacgtggttg gaacgtcttc tttttccacg atgctcctcg   2580
tgggtggggg tccatctttg ggaccactgt cggcagaggc atcttgaacg atagcctttc   2640
ctttatcgca atgtaccgta aacatccacg gtggaaggaa aagatgacag gaaaactact   2700
tcactgtcta tcgatggcat ttgtaggtgc caccttcctt ttctactgtc cttttgatga   2760
agtgacagat agctgggcaa tggaatccga ggaggtttcc cgatattacc ctttgttgaa   2820
aagtctcaat agccctttgg tcttctgaga ctgtatcttt gatattcttg gagtagacga   2880
gagtgtcgtg ctccaccatg ttgacggatc tctaggacgc gtcgagtcta gaggagcatg   2940
cgacgtcggg ccctctagat gcggccgctt taagagtgtt gaggatgtgc ttacttaaat   3000
ttcaaaaggg ctatttaggg ataatatttg gtgaagcatg gctggtggac tgaccatagg   3060
tacccactga ataaacatat cagcccaaag gcagagggta tccctccctg taatacgtac   3120
tagtattcga ggagcgtgct aaagtagtat cctctcttga tgctcctcgt ctccctccac   3180
tgagtactcc cttcctctcc tcattctcat ctcagtcctc tcctcctccc tcgaataaga   3240
tagatccgcc cttgttgctg atctcatctc gcctcctatt ggcctcgccc ctgccaactg   3300
actgctctat tggtgaccgt ggactttttg ggtatatata tttcctgtcg atttgtttcc   3360
acttaaagta gcaatgcttg gatctaaaac ttattacttc tcctgcttca gattctgatc   3420
catttgtgtt gattgaactc agggtgggat cgtggggctc tgtatctatc taggatggat   3480
attccaagca atttactctc ttgagtgctg ttggtcttcc tctgctcctc gtctccgctt   3540
cctctcagtc tcctccattg cgctgcctgg aacagatcga tccgccttgt tgctgatctc   3600
atccatcctc cgtggagatt tcgggtggca gtttccagtg actattcaga gcaccatact   3660
agtggcctgg taaaaatttc cctcccatct ttcttgctat tctcttctta ttaatctgct   3720
gatttgcttg atggtaagtt cttacttatt cttccagatc gagtgaagcg acatccgccg   3780
ccgtcttgtc ccctacgacg ccgctgtgtt ctgctctgtc ctcctctgcc ggtgaagcat   3840
caacggtgac ggccatccgg tgttgacgcc gcggctgtgt tctcctctgc cgtgaagtat   3900
caaaggtggg tttggatgga tatcacagtt tggattggca actctgttct atagctcgtt   3960
gaaattaaag cttcacacag ttttgattgg attacagctc cccatattca tctattttgc   4020
accatgcatc gaatccactg acctccacac gctcacggat ctggcctctg gtgcccacac   4080
gctcacggat ccgacagagt gctcccttcc tatcatctca gtcctcatct cctggtcgat   4140
ccggcttctt gtttggtgag ctcgtccaac ctccgagctc gcccctgaca cctgtggagt   4200
```

-continued

```
ggaggtatat ttctttccag ctgaagtacg cttggatcta aaaacttacg tctcctgctt   4260
cactgcttgc ttgggagtct gatcgatttg tgttggttga atcatttggg gtggcagtgg   4320
agcagctagc aagaatcatg gagtttccaa tcattattca gagcaccacg catggaatcc   4380
actgacctgg taactttgtc tcatctttct tgctactgaa atcttccaca tccccacctt   4440
ccttgttcat ctgctgattt cccagattat acttccagat tgagtgaagc gccgtcttgt   4500
cccctcacgg atctggcctc tggtgcccag ccgccgcttt cgcttcgttg tccgacgagg   4560
ccaccgccgc tgtgttctgc tctgccgtga agcacaaaaa ggtggggtct tcctctgctc   4620
tttctccact gacggcgatc cgaccttgac acccgtggcc gtggcagtgg ggtcttcctc   4680
tgctctgttt ttttaccagt tattggatct aaaaagggat ctaaaagtta ttacttctcc   4740
tgcttgagat tctgaccgat ttgtgttgat tgaatccagg gtggggtcgt ggggctctgt   4800
atctatctag tacggagtac cactgtattc caagcaattt actctcttga ctgctgttgg   4860
acttcctctg tccccgcttc cattgtgctg ccttgaacag atccatccac cttgttgcta   4920
atctcatcca acctccgggt atgtttcttg tcgatttgtt tccagtaaag tagcaatgct   4980
tgggtctaaa aagtcattgc ttctcctgct tgacgagtct cattgatttg cccagtcatt   5040
attcagagca ccatgcatcc aaggcgctga cccggctata agtttttatt acagggccgc   5100
cgtgttgtcc ccatcgagca aagcgtttaa tccactgacc cgcttcgttg tccgcacagc   5160
gtgaccatcc gacgaagacg ccgccgttgt gttctgctct cctctgaagc atcaaaaggt   5220
gggcttggtc cagatcccca cattcatcga tttggcttgc caactcagtt ccaccagagc   5280
ttggattgtg ttacagatcc ctaaattcat cgatttgcag gtttcagctg attgatcaag   5340
agagctctca atgatggagg tcgtcacggg tgccatgggc agcctgctcc ccaagctggg   5400
caagctgctc ctggaggagt acaagctgca caagggcgtc aaggaaaata tcgaggacct   5460
ccggaaggag cttgagagca tgaaccttgc cctcgtcaag attgatgagg tgccgcggga   5520
ccagctcgac agacaagaca agctctgggc agatgatgtc agagatctct cctacaagat   5580
tgaggatgtc gtcgacaagt tcctcatgca cgtcgaccgc attcagcctg acgacaccac   5640
caatggattc aaggggctca tgaagaggac ggccgagttg ttcaagaaag gcaaggatcg   5700
gaatcggata gggcacgcga tgaagggcat ccaggaggaa cttcagaagg tggctgctag   5760
gcgtgacagg aacaaggtcg acggtatggc tcctaatact agggaagcag ttgttatcga   5820
tcctcgtctc cgtgctctgt acacagaagc gacagagctg gttggcatct acgggaagag   5880
ggatcaggac ctcatgagtt tgctctccct ggagggcggc gatgcctcta acaagagact   5940
gaagaaggtg tccattgttg gatttggtgg attgggcaag accactcttg ctagagcagt   6000
atacaacaag attaaaggtg ttttcgattg tcgggcattt gtccccgtcg gccggaaccc   6060
caacatcaag aaggttttta gggatatcct cattgatctc ggcaactcta actcagatct   6120
tgcattattg gatgaaaggc agcttatcaa caagcttcat gaattcctcg agaacaagag   6180
gtatgcgtta cttccagctg aaacaactat actttgatat gttcgtttct atgctagcta   6240
tccaacacta ttatgagttt atgataaata cattgtaacc atcacagaga aggctggttc   6300
agaataattt ttcatttagg tcagtttcaa gactgtataa gcatatatgt ttgatcctcc   6360
tctcctctat ctgaataagt agtaaactac ttctcattgc attagttgcg gtggcttaaa   6420
tttaatgcca ttggtctagg aaatccatct cagcatttat acatttcatc agagatataa   6480
gtaatgagca taataagagt tgtactggat aatacaccaa aatgtaaagg aaagaactca   6540
```

-continued

```
cttagttctt tctttatcct aacccacccc attaaaacaa agatcaaatg gtgcatcgtg   6600
caccaaaggc tgcccttttt ctcttaatac accaagaagt taaatttgct ctttgatatc   6660
acattctatt tcccctttc gccttgttta gaaacttact atcagcagaa tatactcgaa   6720
agggaaatgt catgtaaaat ttgagtctcc gggagtttta tcagcggcca tacagtatat   6780
tggtgggcaa atcagtgctc cgatctttcc aatagatcta cctaaccatt gtaatatttg   6840
aaatgttgta ttccatccga tccaaaataa gtgtcgtggt tttagttcaa acgcttattt   6900
tggatcagat ggagtaacaa attaatcgta cttctatcta tgtcgttgat gcaacaattt   6960
gctcttcgtg ttttactccc ttgaatctta aatttgtatt cattttattc atcatctgac   7020
tggcagtgca taatgcacag ttcttaatat cagattatcg agattgagac gcctgattct   7080
tattagtttg tttctgaata tgtgcactta tagatgtgta gttccaccca catattctta   7140
tggccctaag ctttgtgatg tgtataaacc ttacactgat actctgaact aatgtaggta   7200
tctggtcata attgatgata tatgggatga aaaattgtgg gaatacatca acttggcttt   7260
ctccgacagg aataatctag gcagtcggct aatcaccaca acccgcattg tcagtgtctc   7320
caattcatgt tgctcgtcgg ctaatgattc aatttatcaa atgaaacctc tttctactga   7380
tgattccaga aggctcttcc ataagagaat atttcccgac aagagtgcat gtccaaatga   7440
atttgaacaa gtgtctaatg atatattgaa aaaatgtggt ggagtaccac tagccatcat   7500
tactattgct agtgctttgg ccagtggcca gcaggtgaaa ccaaagcgtg agtgggatat   7560
tctgctccag tcccttggct ctggactaac agaagataac agtttagagg agatgcgtag   7620
aatactctct ttcagctatt ataatctacc atatgatcta aaaacctgtc tattgtacct   7680
atgtatatat ccagaagatc acgagattaa tagagataaa ctgatatgga agtgggtggc   7740
cgaaggattt gtcctccatg gaaatcaagg aactagcctg tttttgctcg gattaaatta   7800
cttcaacgaa ctcatcaata gaagtatgat ccagccaata tatgatcctc tcggccaggt   7860
atatgcttgc cgtgtacatg atatggttct ggaccttatc tgcaacttgt cacatgaagc   7920
aaagtttgtt aatgtattcg atggcactgg gaatatcatg tcctcacaaa gtaatgttcg   7980
tcgtttgtcc cttcagaata aaatggaaga tcatcaagcc aagcctctca caaatatcat   8040
gagtatgtca cgagtgaggt caattactat ctttccacct gctgttagta tcatgccagc   8100
tctgtcaagg tttgaagttc tgcgtgtact tgatatgtcg gactgtaacc ttggggaaag   8160
tagcagcctg cagcctaacc tcaagggtgt tggacactta attcacctaa ggtacctagg   8220
tctatcaggt accggaatta gtaaactccc ggctgagata ggaaccctgc agtttctgga   8280
ggtgttggat cttggataca atcatgagct agatgaattg ccgtccactc tttttaaatt   8340
gagaaggtta atctacctaa atgttcggtt ctataaggtg gttccaactc ctggtgtgtt   8400
gcagaatctg acatccatag aagtgttgag gggctcttg gtgtctctga acatcattgc   8460
acaagagctt ggcaacctgg caaggctgag ggagcttgag attcgcttca aggatggtag   8520
tttggatttg tatgaaggtt tcgtgaagtc tctgtgcaac ctacatcata tcgaaagcct   8580
aagtattagt tgcaattcca aagaaacatc ttttgaactg atggatctct tgggagaacg   8640
ctgggtgcct cctgtacatc tccgcgaatt tgtgtcatac atccccagcc aaatctctgc   8700
actgcgaggg tggatagaga gagatccctc gcatctctcg aacctctccg agttaatcct   8760
cacgtcagtg aaggaggtgc agcaggagga cgtggaaatc attgggggt tgctgtccct   8820
tcgcaatctc tggataacga gcacccacca aacacagcgg ctgctagtca tccgtgcaga   8880
tgggttccgc tgtatgctaa actttgagtt gaattgtgga tcagccgcac aaataatgtt   8940
```

-continued

```
tgaatcagga gctttgccga gggcggaaag agttgagttc agtctcggcg tgcgggtggc   9000
gaaagaggat ggtaaccgtg gtttcaactt gggcctgcag gggaacctgc tctcccttcg   9060
gcgtggtgtc cggatttgga tgtattgtgg tggagcgagg gttggggagg ccaaggaagc   9120
ggaggctgcg gtgaggcacg ccctcgacgc ccatcccagc catcccctga ttttgattga   9180
gatgaggccg cgtatacaag aaggtactca tgtcgcacct aactactcac gctcaactcc   9240
catcccaatc atccccgatt acgtatatgt ttttttcgaa tgagcttctg acgttgcttc   9300
aggtgtgctc tcaatctata catatttact catcatatta ttctccacct ttttttccat   9360
ctctagagct cagcttgtca ttgcattgtt caattgtgct tctctagcag ctacggaaat   9420
tctgaacagg caaaggtaat tttacagaag tttctttggc ataagtatct gagaaaaatg   9480
cacttggcac aatttacctt ttcgcagtag aaaagagtca gtggatcata ccttcttaat   9540
tgttcgattg ctcgtaatac ttgggggcac tctatgattg ctgtgtgctt ttagttttga   9600
tatagttcct gttagcatgg acagactgtg tgattggttc atgaatttca gggtggttct   9660
aatgaggaaa tgatgcttgc ttcagaaata gtttccattt gtacctaagc tgtgtagttg   9720
gtaaagttgc attttggatg ttctgttggt atagcttaca gaagaaagac ttgcgttgtg   9780
caggtaccag gggcgcaggt tactgctagt ggcgtctgag atgtttcata aacgttgggt   9840
gggcaccggt catgcaaaaa attgaaggat aaaaaggttc cgagaggttg tgtgatgtgc   9900
tccttttaaa tggcagtcgc ttgcataaag agatgttgct tggtttttta gtaaagcgtt   9960
gtagtaagtt gctctgtttc ggctgagagc catcgttgtt gctgtctgtt acatcgaatg  10020
gctggctcat gtcatgttga tgtttttttt atctgaaccg gacaaacctg agggtgtagt  10080
atcatgtttg taatgactga aattctgggc tcacccgagc tccttaattc gtaaacaact  10140
gcgactcatt gttggattcc ttacttcaga aaatatttac ttgctctggc tcatacagct  10200
ctgcatgttt tgtagtggtt tgtcgctgtt taggtgctgc ttcagactcc tggtaccttt  10260
ggccgctgct gctactgcat gagctttgta tggcattgtt agtatagttt ggtgtcattg  10320
ggttttcgcc ccatggtgag tgtccattgc gcgcactcgc agcggtttcc tggcgataag  10380
ttgaacttga tctttctctt tcccacctcc taaacgtcta ttcagacttg tgtatatttg  10440
cattacgggg attacccgag ttcaaaaata aatattattt actagttctg ccaatgtgtt  10500
tccgttacat acaaataaaa gggtgcttcc agctacaagt atatttttga gaagggccat  10560
tgcaaaacga aatgaagccc aaattctacc aacatgtttc tgtcacatat acattaaaaa  10620
aacggtgtaa atgtcccgtc aaaaaagggt gtatgtagga aaaggagttc gacgccgcca  10680
gctccctcct aacgctcaga ttgtcttcgc ggccgcatgc ataagcttat cgatgataag  10740
ctgtcaaaca tgagaattca gtacattaaa aacgtccgca atgtgttatt aagttgtcta  10800
agcgtcaatt tgtttacacc acaatatatc ctgccaccag ccagccaaca gctccccgac  10860
cggcagctcg gcacaaaatc accactcgat acaggcagcc catcagtccg ggacggcgtc  10920
agcgggagag ccgttgtaag gcggcagact ttgctcatgt taccgatgct attcggaaga  10980
acggcaacta agctgccggg tttgaaacac ggatgatctc gcggagggta gcatgttgat  11040
tgtaacgatg acagagcgtt gctgcctgtg atcaaatatc atctccctcg cagagatccg  11100
aattatcagc cttcttattc atttctcgct taaccgtgac aggctgtcga tcttgagaac  11160
tatgccgaca taataggaaa tcgctggata aagccgctga ggaagctgag tggcgctatt  11220
tctttagaag tgaacgttga cgatcgtcga cggatctttt ccgctgcata accctgcttc  11280
```

-continued

```
ggggtcatta tagcgatttt ttcggtatat ccatcctttt tcgcacgata tacaggattt  11340
tgccaaaggg ttcgtgtaga ctttccttgg tgtatccaac ggcgtcagcc gggcaggata  11400
ggtgaagtag gcccacccgc gagcgggtgt tccttcttca ctgtccctta ttcgcacctg  11460
gcggtgctca acgggaatcc tgctctgcga ggctggccgg ctaccgccgg cgtaacagat  11520
gagggcaagc ggatggctga tgaaaccaag ccaaccaggg gtgatgctgc caacttactg  11580
atttagtgta tgatggtgtt tttgaggtgc tccagtggct tctgtttcta tcagctgtcc  11640
ctcctgttca gctactgacg gggtggtgcg taacggcaaa agcaccgccg gacatcagcg  11700
ctatctctgc tctcactgcc gtaaaacatg gcaactgcag ttcacttaca ccgcttctca  11760
acccggtacg caccagaaaa tcattgatat ggccatgaat ggcgttggat gccgggcaac  11820
agcccgcatt atgggcgttg gcctcaacac gattttacgt cacttaaaaa actcaggccg  11880
cagtcggtaa cctcgcgcat acagccgggc agtgacgtca tcgtctgcgc ggaaatggac  11940
gaacagtggg gctatgtcgg ggctaaatcg cgccagcgct ggctgtttta cgcgtatgac  12000
agtctccgga agacggttgt tgcgcacgta ttcggtgaac gcactatggc gacgctgggg  12060
cgtcttatga gcctgctgtc accctttgac gtggtgatat ggatgacgga tggctggccg  12120
ctgtatgaat cccgcctgaa gggaaagctg cacgtaatca gcaagcgata tacgcagcga  12180
attgagcggc ataacctgaa tctgaggcag cacctggcac ggctgggacg gaagtcgctg  12240
tcgttctcaa aatcggtgga gctgcatgac aaagtcatcg ggcattatct gaacataaaa  12300
cactatcaat aagttggagt cattacccaa ccaggaaggg cagcccacct atcaaggtgt  12360
actgccttcc agacgaacga agagcgattg aggaaaaggc ggcggcggcc ggcatgagcc  12420
tgtcggccta cctgctggcc gtcggccagg gctacaaaat cacgggcgtc gtggactatg  12480
agcacgtccg cgagctggcc cgcatcaatg gcgacctggg ccgcctgggc ggcctgctga  12540
aactctggct caccgacgac ccgcgcacgg cgcggttcgg tgatgccacg atcctcgccc  12600
tgctggcgaa gatcgaagag aagcaggacg agcttggcaa ggtcatgatg ggcgtggtcc  12660
gcccgagggc agagccatga ctttttttagc cgctaaaacg gccggggggt gcgcgtgatt  12720
gccaagcacg tccccatgcg ctccatcaag aagagcgact tcgcggagct ggtattcgtg  12780
cagggcaaga ttcggaatac caagtacgag aaggacggcc agacggtcta cgggaccgac  12840
ttcattgccg ataaggtgga ttatctggac accaaggcac caggcgggtc aaatcaggaa  12900
taagggcaca ttgccccggc gtgagtcggg gcaatcccgc aaggagggtg aatgaatcgg  12960
acgtttgacc ggaaggcata caggcaagaa ctgatcgacg cggggttttc cgccgaggat  13020
gccgaaacca tcgcaagccg caccgtcatg cgtgcgcccc gcgaaacctt ccagtccgtc  13080
ggctcgatgg tccagcaagc tacggccaag atcgagcgcg acagcgtgca actggctccc  13140
cctgccctgc ccgcgccatc ggccgccgtg gagcgttcgc gtcgtctcga acaggaggcg  13200
gcaggtttgg cgaagtcgat gaccatcgac acgcgaggaa ctatgacgac caagaagcga  13260
aaaaccgccg gcgaggacct ggcaaaacag gtcagcgagg ccaagcaggc cgcgttgctg  13320
aaacacacga agcagcagat caaggaaatg cagctttcct tgttcgatat tgcgccgtgg  13380
ccggacacga tgcgagcgat gccaaacgac acggcccgct ctgccctgtt caccacgcgc  13440
aacaagaaaa tcccgcgcga ggcgctgcaa aacaaggtca ttttccacgt caacaaggac  13500
gtgaagatca cctacaccgg cgtcgagctg cgggccgacg atgacgaact ggtgtggcag  13560
caggtgttgg agtacgcgaa gcgcacccct atcggcgagc cgatcacctt cacgttctac  13620
gagctttgcc aggacctggg ctggtcgatc aatggccggt attacacgaa ggccgaggaa  13680
```

```
tgcctgtcgc gcctacaggc gacggcgatg ggcttcacgt ccgaccgcgt tgggcacctg  13740
gaatcggtgt cgctgctgca ccgcttccgc gtcctggacc gtggcaagaa aacgtcccgt  13800
tgccaggtcc tgatcgacga ggaaatcgtc gtgctgtttg ctggcgacca ctacacgaaa  13860
ttcatatggg agaagtaccg caagctgtcg ccgacggccc gacggatgtt cgactatttc  13920
agctcgcacc gggagccgta cccgctcaag ctggaaacct tccgcctcat gtgcggatcg  13980
gattccaccc gcgtgaagaa gtggcgcgag caggtcggcg aagcctgcga agagttgcga  14040
ggcagcggcc tggtggaaca cgcctgggtc aatgatgacc tggtgcattg caaacgctag  14100
ggccttgtgg ggtcagttcc ggctgggggt tcagcagcca gcgctttact ggcatttcag  14160
gaacaagcgg gcactgctcg acgcacttgc ttcgctcagt atcgctcggg acgcacggcg  14220
cgctctacga actgccgata aacagaggat taaaattgac aattgtgatt aaggctcaga  14280
ttcgacggct tggagcggcc gacgtgcagg atttccgcga gatccgattg tcggccctga  14340
agaaagctcc agagatgttc gggtccgttt acgagcacga ggagaaaaag cccatggagg  14400
cgttcgctga acggttgcga gatgccgtgg cattcggcgc ctacatcgac ggcgagatca  14460
ttgggctgtc ggtcttcaaa caggaggacg gccccaagga cgctcacaag gcgcatctgt  14520
ccggcgtttt cgtggagccc gaacagcgag gccgaggggt cgccggtatg ctgctgcggg  14580
cgttgccggc gggtttattg ctcgtgatga tcgtccgaca gattccaacg ggaatctggt  14640
ggatgcgcat cttcatcctc ggcgcactta atatttcgct attctggagc ttgttgttta  14700
tttcggtcta ccgcctgccg ggcggggtcg cggcgacggt aggcgctgtg cagccgctga  14760
tggtcgtgtt catctctgcc gctctgctag gtagcccgat acgattgatg gcggtcctgg  14820
gggctatttg cggaactgcg ggcgtggcgc tgttggtgtt gacaccaaac gcagcgctag  14880
atcctgtcgg cgtcgcagcg ggcctggcgg gggcggtttc catggcgttc ggaaccgtgc  14940
tgacccgcaa gtggcaacct cccgtgcctc tgctcacctt taccgcctgg caactggcgg  15000
ccggaggact tctgctcgtt ccagtagctt tagtgtttga tccgccaatc ccgatgccta  15060
caggaaccaa tgttctcggc ctggcgtggc tcggcctgat cggagcgggt ttaacctact  15120
tcctttggtt ccgggggatc tcgcgactcg aacctacagt tgtttcctta ctgggctttc  15180
tcagccggga tggcgctaag aagctattgc cgccgatctt catatgcggt gtgaaatacc  15240
gcacagatgc gtaaggagaa aataccgcat caggcgctct tccgcttcct cgctcactga  15300
ctcgctgcgc tcggtcgttc ggctgcggcg agcggtatca gctcactcaa aggcggtaat  15360
acggttatcc acagaatcag gggataacgc aggaaagaac atgtgagcaa aaggccagca  15420
aaaggccagg aaccgtaaaa aggccgcgtt gctggcgttt ttccataggc tccgcccccc  15480
tgacgagcat cacaaaaatc gacgctcaag tcagaggtgg cgaaacccga caggactata  15540
aagataccag gcgtttcccc ctggaagctc cctcgtgcgc tctcctgttc cgaccctgcc  15600
gcttaccgga tacctgtccg cctttctccc ttcgggaagc gtggcgcttt ctcaatgctc  15660
acgctgtagg tatctcagtt cggtgtaggt cgttcgctcc aagctgggct gtgtgcacga  15720
accccccgtt cagcccgacc gctgcgcctt atccggtaac tatcgtcttg agtccaaccc  15780
ggtaagacac gacttatcgc cactggcagc agccactggt aacaggatta gcagagcgag  15840
gtatgtaggc ggtgctacag agttcttgaa gtggtggcct aactacggct acactagaag  15900
gacagtattt ggtatctgcg ctctgctgaa gccagttacc ttcggaaaaa gagttggtag  15960
ctcttgatcc ggcaaacaaa ccaccgctgg tagcggtggt ttttttgttt gcaagcagca  16020
```

-continued gattacgcgc agaaaaaaag gatatcaaga agatcctttg atcttttcta cggggtctga 16080
cgctcagtgg aacgaaaact cacgttaagg gattttggtc atgagattat caaaaaggat 16140
cttcacctag atccttttaa attaaaaatg aagttttaaa tcaatctaaa gtatatatga 16200
gtaaacttgg tctgacagtt accaatgctt aatcagtgag gcacctatct cagcgatctg 16260
tctatttcgt tcatccatag ttgcctgact ccccgtcgtg tagataacta cgatacggga 16320
gggcttacca tctggcccca gtgctgcaat gataccgcga gacccacgct caccggctcc 16380
agatttatca gcaataaacc agccagccgg aagggccgag cgcagaagtg gtcctgcaac 16440
tttatccgcc tccatccagt ctattaaaca agtggcagca acggattcgc aaacctgtca 16500
cgccttttgt gccaaaagcc gcgccaggtt tgcgatccgc tgtgccaggc gttaggcgtc 16560
atatgaagat ttcggtgatc cctgagcagg tggcggaaac attggatgct gagaaccatt 16620
tcattgttcg tgaagtgttc gatgtgcacc tatccgacca aggctttgaa ctatctacca 16680
gaagtgtgag cccctaccgg aaggattaca tctcggatga tgactctgat gaagactctg 16740
cttgctatgg cgcattcatc gaccaagagc ttgtcgggaa gattgaactc aactcaacat 16800
ggaacgatct agcctctatc gaacacattg ttgtgtcgca cacgcaccga ggcaaaggag 16860
tcgcgcacag tctcatcgaa tttgcgaaaa agtgggcact aagcagacag ctccttggca 16920
tacgattaga gacacaaacg aacaatgtac ctgcctgcaa tttgtacgca aaatgtggct 16980
ttactctcgg cggcattgac ctgttcacgt ataaaactag acctcaagtc tcgaacgaaa 17040
cagcgatgta ctggtactgg ttctcgggag cacaggatga cgcctaacaa ttcattcaag 17100
ccgacaccgc ttcgcggcgc ggcttaattc aggagttaaa catcatgagg gaagcggtga 17160
tcgccgaagt atcgactcaa ctatcagagg tagttggcgt catcgagcgc catctcgaac 17220
cgacgttgct ggccgtacat ttgtacggct ccgcagtgga tggcggcctg aagccacaca 17280
gtgatattga tttgctggtt acggtgaccg taaggcttga tgaaacaacg cggcgagctt 17340
tgatcaacga ccttttggaa acttcggctt cccctggaga gagcgagatt ctccgcgctg 17400
tagaagtcac cattgttgtg cacgacgaca tcattccgtg gcgttatcca gctaagcgcg 17460
aactgcaatt tggagaatgg cagcgcaatg acattcttgc aggtatcttc gagccagcca 17520
cgatcgacat tgatctggct atcttgctga caaaagcaag agaacatagc gttgccttgg 17580
taggtccagc ggcggaggaa ctctttgatc cggttcctga acaggatcta tttgaggcgc 17640
taaatgaaac cttaacgcta tggaactcgc cgcccgactg ggctggcgat gagcgaaatg 17700
tagtgcttac gttgtcccgc atttggtaca gcgcagtaac cggcaaaatc gcgccgaagg 17760
atgtcgctgc cgactgggca atggagcgcc tgccggccca gtatcagccc gtcatacttg 17820
aagctaggca ggcttatctt ggacaagaag atcgcttggc ctcgcgcgca gatcagttgg 17880
aagaatttgt tcactacgtg aaaggcgaga tcaccaaggt agtcggcaaa taatgtctaa 17940
caattcgttc aagccgacgc cgcttcgcgg cgcggcttaa ctcaagcgtt agagagctgg 18000
ggaagactat gcgcgatctg ttgaaggtgg ttctaagcct cgtacttgcg atggcatcgg 18060
ggcaggcact tgctgacctg ccaattgttt tagtggatga agctcgtctt ccctatgact 18120
actccccatc caactacgac atttctccaa gcaactacga caactccata agcaattacg 18180
acaatagtcc atcaaattac gacaactctg agagcaacta cgataatagt tcatccaatt 18240
acgacaatag tcgcaacgga aatcgtaggc ttatatatag cgcaaatggg tctcgcactt 18300
tcgccggcta ctacgtcatt gccaacaatg ggacaacgaa cttcttttcc acatctggca 18360
aaaggatgtt ctacacccca aaagggggc gcggcgtcta tggcggcaaa gatgggagct 18420

-continued tctgcggggc attggtcgtc ataaatggcc aattttcgct tgccctgaca gataacggcc 18480
tgaagatcat gtatctaagc aactagcctg ctctctaata aaatgttagg agcttggctg 18540
ccatttttgg ggtgaggccg ttcgcggccg aggggcgcag cccctggggg gatgggaggc 18600
ccgcgttagc gggccgggag ggttcgagaa ggggggcac cccccttcgg cgtgcgcggt 18660
cacgcgccag ggcgcagccc tggttaaaaa caaggtttat aaatattggt ttaaaagcag 18720
gttaaaagac aggttagcgg tggccgaaaa acgggcggaa acccttgcaa atgctggatt 18780
ttctgcctgt ggacagcccc tcaaatgtca ataggtgcgc ccctcatctg tcagcactct 18840
gcccctcaag tgtcaaggat cgcgcccctc atctgtcagt agtcgcgccc ctcaagtgtc 18900
aataccgcag ggcacttatc cccaggcttg tccacatcat ctgtgggaaa ctcgcgtaaa 18960
atcaggcgtt ttcgccgatt tgcgaggctg gccagctcca cgtcgccggc cgaaatcgag 19020
cctgcccctc atctgtcaac gccgcgccgg gtgagtcggc ccctcaagtg tcaacgtccg 19080
cccctcatct gtcagtgagg gccaagtttt ccgcgaggta tccacaacgc cggcggccgg 19140
ccgcggtgtc tcgcacacgg cttcgacggc gtttctggcg cgtttgcagg gccatagacg 19200
gccgccagcc cagcggcgag ggcaaccagc ccggtgagcg tcggaaaggg 19250

<210> SEQ ID NO 6
<211> LENGTH: 3933
<212> TYPE: DNA
<213> ORGANISM: Artificial Sequence
<220> FEATURE:
<223> OTHER INFORMATION: Artificial sequence comprising domesticated SrTA1662 open reading frame

<400> SEQUENCE: 6
atgatggagg tcgtcacggg tgccatgggc agcctgctcc ccaagctggg caagctgctc 60
ctggaggagt acaagctgca caagggcgtc aaggaaaaata tcgaggacct ccggaaggag 120
cttgagagca tgaaccttgc cctcgtcaag attgatgagg tgccgcggga ccagctcgac 180
agacaagaca agctctgggc agatgatgtc agagatctct cctacaagat tgaggatgtc 240
gtcgacaagt tcctcatgca cgtcgaccgc attcagcctg acgacaccac caatggattc 300
aaggggctca tgaagaggac ggccgagttg ttcaagaaag gcaaggatcg gaatcggata 360
gggcacgcga tgaagggcat ccaggaggaa cttcagaagg tggctgctag gcgtgacagg 420
aacaaggtcg acggtatggc tcctaatact agggaagcag ttgttatcga tcctcgtctc 480
cgtgctctgt acacagaagc gacagagctg gttggcatct acgggaagag ggatcaggac 540
ctcatgagtt tgctctccct ggagggcggc gatgcctcta acaagagact gaagaaggtg 600
tccattgttg gatttggtgg attgggcaag accactcttg ctagagcagt atacaacaag 660
attaaaggtg ttttcgattg tcgggcattt gtccccgtcg gccggaaccc caacatcaag 720
aaggttttta gggatatcct cattgatctc ggcaactcta actcagatct tgcattattg 780
gatgaaaggc agcttatcaa caagcttcat gaattcctcg agaacaagag gtatgcgtta 840
cttccagctg aaacaactat actttgatat gttcgtttct atgctagcta tccaacacta 900
ttatgagttt atgataaata cattgtaacc atcacagaga aggctggttc agaataattt 960
ttcatttagg tcagtttcaa gactgtataa gcatatatgt ttgatcctcc tctcctctat 1020
ctgaataagt agtaaactac ttctcattgc attagttgcg gtggcttaaa tttaatgcca 1080
ttggtctagg aaatccatct cagcatttat acatttcatc agagatataa gtaatgagca 1140
taataagagt tgtactggat aatacaccaa aatgtaaagg aaagaactca cttagttctt 1200

-continued

```
tctttatcct aacccacccc attaaaacaa agatcaaatg gtgcatcgtg caccaaaggc   1260
tgcccttttt ctcttaatac accaagaagt taaatttgct ctttgatatc acattctatt   1320
tccccttttc gccttgttta gaaacttact atcagcagaa tatactcgaa agggaaatgt   1380
catgtaaaat ttgagtctcc gggagtttta tcagcggcca tacagtatat tggtgggcaa   1440
atcagtgctc cgatctttcc aatagatcta cctaaccatt gtaatatttg aaatgttgta   1500
ttccatccga tccaaaataa gtgtcgtggt tttagttcaa acgcttattt tggatcagat   1560
ggagtaacaa attaatcgta cttctatcta tgtcgttgat gcaacaattt gctcttcgtg   1620
ttttactccc ttgaatctta aatttgtatt cattttattc atcatctgac tggcagtgca   1680
taatgcacag ttcttaatat cagattatcg agattgagac gcctgattct tattagtttg   1740
tttctgaata tgtgcactta tagatgtgta gttccaccca catattctta tggccctaag   1800
ctttgtgatg tgtataaacc ttacactgat actctgaact aatgtaggta tctggtcata   1860
attgatgata tatgggatga aaaattgtgg gaatacatca acttggcttt ctccgacagg   1920
aataatctag gcagtcggct aatcaccaca acccgcattg tcagtgtctc caattcatgt   1980
tgctcgtcgg ctaatgattc aatttatcaa atgaaacctc tttctactga tgattccaga   2040
aggctcttcc ataagagaat atttcccgac aagagtgcat gtccaaatga atttgaacaa   2100
gtgtctaatg atatattgaa aaaatgtggt ggagtaccac tagccatcat tactattgct   2160
agtgctttgg ccagtggcca gcaggtgaaa ccaaagcgtg agtgggatat tctgctccag   2220
tcccttggct ctggactaac agaagataac agtttagagg agatgcgtag aatactctct   2280
ttcagctatt ataatctacc atatgatcta aaaacctgtc tattgtacct atgtatatat   2340
ccagaagatc acgagattaa tagagataaa ctgatatgga agtgggtggc cgaaggattt   2400
gtcctccatg gaaatcaagg aactagcctg tttttgctcg gattaaatta cttcaacgaa   2460
ctcatcaata gaagtatgat ccagccaata tatgatcctc tcggccaggt atatgcttgc   2520
cgtgtacatg atatggttct ggaccttatc tgcaacttgt cacatgaagc aaagtttgtt   2580
aatgtattcg atggcactgg gaatatcatg tcctcacaaa gtaatgttcg tcgtttgtcc   2640
cttcagaata aaatggaaga tcatcaagcc aagcctctca caaatatcat gagtatgtca   2700
cgagtgaggt caattactat ctttccacct gctgttagta tcatgccagc tctgtcaagg   2760
tttgaagttc tgcgtgtact tgatatgtcg gactgtaacc ttggggaaag tagcagcctg   2820
cagcctaacc tcaagggtgt tggacactta attcacctaa ggtacctagg tctatcaggt   2880
accggaatta gtaaactccc ggctgagata ggaaccctgc agtttctgga ggtgttggat   2940
cttggataca atcatgagct agatgaattg ccgtccactc tttttaaatt gagaaggtta   3000
atctacctaa atgttcggtt ctataaggtg gttccaactc ctggtgtgtt gcagaatctg   3060
acatccatag aagtgttgag gggctcttg gtgtctctga acatcattgc acaagagctt   3120
ggcaacctgg caaggctgag ggagcttgag attcgcttca aggatggtag tttggatttg   3180
tatgaaggtt tcgtgaagtc tctgtgcaac ctacatcata tcgaaagcct aagtattagt   3240
tgcaattcca aagaaacatc ttttgaactg atggatctct tgggagaacg ctgggtgcct   3300
cctgtacatc tccgcgaatt tgtgtcatac atccccagcc aaatctctgc actgcgaggg   3360
tggatagaga gagatccctc gcatctctcg aacctctccg agttaatcct cacgtcagtg   3420
aaggaggtgc agcaggagga cgtggaaatc attgggggt tgctgtccct tcgcaatctc   3480
tggataacga gcacccacca aacacagcgg ctgctagtca tccgtgcaga tgggttccgc   3540
```

-continued

```
tgtatgctaa actttgagtt gaattgtgga tcagccgcac aaataatgtt tgaatcagga   3600

gctttgccga gggcggaaag agttgagttc agtctcggcg tgcgggtggc gaaagaggat   3660

ggtaaccgtg gtttcaactt gggcctgcag gggaacctgc tctcccttcg gcgtggtgtc   3720

cggatttgga tgtattgtgg tggagcgagg gttggggagg ccaaggaagc ggaggctgcg   3780

gtgaggcacg ccctcgacgc ccatcccagc catcccctga ttttgattga gatgaggccg   3840

cgtatacaag aaggtactca tgtcgcacct aactactcac gctcaactcc catcccaatc   3900

atccccgatt acgtatatgt ttttttcgaa tga                                 3933
```

```
<210> SEQ ID NO 7
<211> LENGTH: 971
<212> TYPE: PRT
<213> ORGANISM: Artificial Sequence
<220> FEATURE:
<223> OTHER INFORMATION: Fusion protein

<400> SEQUENCE: 7

Met Met Glu Val Val Thr Gly Ala Met Gly Ser Leu Leu Pro Lys Leu
1               5                   10                  15

Gly Lys Leu Leu Leu Glu Glu Tyr Lys Leu His Lys Gly Val Lys Glu
            20                  25                  30

Asn Ile Glu Asp Leu Arg Lys Glu Leu Glu Ser Met Asn Leu Ala Leu
        35                  40                  45

Val Lys Ile Asp Glu Val Pro Arg Asp Gln Leu Asp Arg Gln Asp Lys
    50                  55                  60

Leu Trp Ala Asp Asp Val Arg Asp Leu Ser Tyr Lys Ile Glu Asp Val
65                  70                  75                  80

Val Asp Lys Phe Leu Met His Val Asp Arg Ile Gln Pro Asp Asp Thr
                85                  90                  95

Thr Asn Gly Phe Lys Gly Leu Met Lys Arg Thr Ala Glu Leu Phe Lys
            100                 105                 110

Lys Gly Lys Asp Arg Asn Arg Ile Gly His Ala Met Lys Gly Ile Gln
        115                 120                 125

Glu Glu Leu Gln Lys Val Ala Ala Arg Arg Asp Arg Asn Lys Val Asp
    130                 135                 140

Gly Met Ala Pro Asn Thr Arg Glu Ala Val Val Ile Asp Pro Arg Leu
145                 150                 155                 160

Arg Ala Leu Tyr Thr Glu Ala Thr Glu Leu Val Gly Ile Tyr Gly Lys
                165                 170                 175

Arg Asp Gln Asp Leu Met Ser Leu Leu Ser Leu Glu Gly Gly Asp Ala
            180                 185                 190

Ser Asn Lys Arg Leu Lys Lys Val Ser Ile Val Gly Phe Gly Gly Leu
        195                 200                 205

Gly Lys Thr Thr Leu Ala Arg Ala Val Tyr Asn Lys Ile Lys Gly Val
    210                 215                 220

Phe Asp Cys Arg Ala Phe Val Pro Val Gly Arg Asn Pro Asn Ile Lys
225                 230                 235                 240

Lys Val Phe Arg Asp Ile Leu Ile Asp Leu Gly Asn Ser Asn Ser Asp
                245                 250                 255

Leu Ala Leu Leu Asp Glu Arg Gln Leu Ile Asn Lys Leu His Glu Phe
            260                 265                 270

Leu Glu Asn Lys Arg Tyr Leu Val Ile Ile Asp Asp Ile Trp Asp Glu
        275                 280                 285

Lys Leu Trp Glu Tyr Ile Asn Leu Ala Phe Ser Asp Arg Asn Asn Leu
```

-continued

```
    290                 295                 300

Gly Ser Arg Leu Ile Thr Thr Thr Arg Ile Val Ser Val Ser Asn Ser
305                 310                 315                 320

Cys Cys Ser Ser Ala Asn Asp Ser Ile Tyr Gln Met Lys Pro Leu Ser
                325                 330                 335

Thr Asp Asp Ser Arg Arg Leu Phe His Lys Arg Ile Phe Pro Asp Lys
            340                 345                 350

Ser Ala Cys Pro Asn Glu Phe Glu Gln Val Ser Asn Asp Ile Leu Lys
        355                 360                 365

Lys Cys Gly Gly Val Pro Leu Ala Ile Ile Thr Ile Ala Ser Ala Leu
    370                 375                 380

Ala Ser Gly Gln Gln Val Lys Pro Lys Arg Glu Trp Asp Ile Leu Leu
385                 390                 395                 400

Gln Ser Leu Gly Ser Gly Leu Thr Glu Asp Asn Ser Leu Glu Glu Met
                405                 410                 415

Arg Arg Ile Leu Ser Phe Ser Tyr Tyr Asn Leu Pro Tyr Asp Leu Lys
            420                 425                 430

Thr Cys Leu Leu Tyr Leu Cys Ile Tyr Pro Glu Asp His Glu Ile Asn
        435                 440                 445

Arg Asp Lys Leu Ile Trp Lys Trp Val Ala Glu Gly Phe Val Leu His
    450                 455                 460

Gly Asn Gln Gly Thr Ser Leu Phe Leu Leu Gly Leu Asn Tyr Phe Asn
465                 470                 475                 480

Glu Leu Ile Asn Arg Ser Met Ile Gln Pro Ile Tyr Asp Pro Leu Gly
                485                 490                 495

Gln Val Tyr Ala Cys Arg Val His Asp Met Val Leu Asp Leu Ile Cys
            500                 505                 510

Asn Leu Ser His Glu Ala Lys Phe Val Asn Val Phe Asp Gly Thr Gly
        515                 520                 525

Asn Ile Met Ser Ser Gln Ser Asn Val Arg Arg Leu Ser Leu Gln Asn
    530                 535                 540

Lys Met Glu Asp His Gln Ala Lys Pro Leu Thr Asn Ile Met Ser Met
545                 550                 555                 560

Ser Arg Val Arg Ser Ile Thr Ile Phe Pro Pro Ala Val Ser Ile Met
                565                 570                 575

Pro Ala Leu Ser Arg Phe Glu Val Leu Arg Val Leu Asp Met Ser Asp
            580                 585                 590

Cys Asn Leu Gly Glu Ser Ser Ser Leu Gln Pro Asn Leu Lys Gly Val
        595                 600                 605

Gly His Leu Ile His Leu Arg Tyr Leu Gly Leu Ser Gly Thr Gly Ile
    610                 615                 620

Ser Lys Leu Pro Ala Glu Ile Gly Thr Leu Gln Phe Leu Glu Val Leu
625                 630                 635                 640

Asp Leu Gly Tyr Asn His Glu Leu Asp Glu Leu Pro Ser Thr Leu Phe
                645                 650                 655

Lys Leu Arg Arg Leu Ile Tyr Leu Asn Val Arg Phe Tyr Lys Val Val
            660                 665                 670

Pro Thr Pro Gly Val Leu Gln Asn Leu Thr Ser Ile Glu Val Leu Arg
        675                 680                 685

Gly Leu Leu Val Ser Leu Asn Ile Ile Ala Gln Glu Leu Gly Asn Leu
    690                 695                 700

Ala Arg Leu Arg Glu Leu Glu Ile Arg Phe Lys Asp Gly Ser Leu Asp
705                 710                 715                 720
```

```
Leu Tyr Glu Gly Phe Val Lys Ser Leu Cys Asn Leu His His Ile Glu
                725                 730                 735

Ser Leu Ser Ile Ser Cys Asn Ser Lys Glu Thr Ser Phe Glu Leu Met
            740                 745                 750

Asp Leu Leu Gly Glu Arg Trp Val Pro Pro Val His Leu Arg Glu Phe
        755                 760                 765

Val Ser Tyr Ile Pro Ser Gln Ile Ser Ala Leu Arg Gly Trp Ile Glu
    770                 775                 780

Arg Asp Pro Ser His Leu Ser Asn Leu Ser Glu Leu Ile Leu Thr Ser
785                 790                 795                 800

Val Lys Glu Val Gln Gln Glu Asp Val Glu Ile Ile Gly Gly Leu Leu
                805                 810                 815

Ser Leu Arg Asn Leu Trp Ile Thr Ser Thr His Gln Thr Gln Arg Leu
            820                 825                 830

Leu Val Ile Arg Ala Asp Gly Phe Arg Cys Met Leu Asn Phe Glu Leu
        835                 840                 845

Asn Cys Gly Ser Ala Ala Gln Ile Met Phe Glu Ser Gly Ala Leu Pro
    850                 855                 860

Arg Ala Glu Arg Val Glu Phe Ser Leu Gly Val Arg Val Ala Lys Glu
865                 870                 875                 880

Asp Gly Asn Arg Gly Phe Asn Leu Gly Leu Gln Gly Asn Leu Leu Ser
                885                 890                 895

Leu Arg Arg Gly Val Arg Ile Trp Met Tyr Cys Gly Gly Ala Arg Val
            900                 905                 910

Gly Glu Ala Lys Glu Ala Glu Ala Ala Val Arg His Ala Leu Asp Ala
        915                 920                 925

His Pro Ser His Pro Leu Ile Leu Ile Glu Met Arg Pro Arg Ile Gln
    930                 935                 940

Glu Gly Thr His Val Ala Pro Asn Tyr Ser Arg Ser Thr Pro Ile Pro
945                 950                 955                 960

Ile Ile Pro Asp Tyr Val Tyr Val Phe Phe Glu
                965                 970
```

<210> SEQ ID NO 8
<211> LENGTH: 10445
<212> TYPE: DNA
<213> ORGANISM: Aegilops tauschii

<400> SEQUENCE: 8

```
atgaggcgtt ttaggtcacg gaagtctggc atggctgcat ctattttgaa cacggtctgt     60

acacgtagac ataacaaaga aagaaaacct gtgtgttcat acctggggtt gaaaccgtac    120

agcgtcgccg atcgcacgtt ccgcggcgcc ccacgatcta gaatctgcca gcggcggcgg    180

ccctatcgag tcgttccgtg gcggcggcgc tgtggagtcg ttccgcggcg gcggcgctgt    240

ggagtgcgca gcgatccaga aacgtggcgg cggcgctgtg gagtgcgcag atcgcacgac    300

ggctgtgcag atctgatcgg cagcggggta tggggatggg cgtcagggcg atcctgatcg    360

gcggcagggt gctgcttctt acgtgcgtgg gtggggttcg gtgggtgggc gtgggggtgg    420

gggtaatttg atggaaaaaa acaggttgaa aaaaaccagt cgaaaaaaaa ccagacgaaa    480

gtggggggac tattcaacca actcgttcat tagaaataga gattgttaca gtttagcgtg    540

tgtgcatgat cgctcagttt tgcaagcaag gtttcaggtt ctgaacttcc aaaccatgac    600

ttaagttcta tttccattca ctgaactggt tatattgggg gtctgtggtg gggatttgtt    660
```

-continued

```
ggttcttcac gttcatgatt cttgtgctac cttcaaatca atatggtgca gcattttgtg    720
ttctgatgct tgctgcccaa aaattctttt gatattttat aaaaaaaagt cctaaactag    780
tgaccattgt tttttgcctc atgacgtgac ctcagatgtc cctctcaata tttagatagg    840
caacctaatg catgagctct gatgttccgt tgaacttttt atgcgagtat aacattagat    900
cacgtgtgtt ccaaaacgtt cgagaatttt ttgacctttt tgcaacttct attctttttc    960
gattcaggtg cactggatcc gagatccatt gggtattttc ggtatcgatt gcttttgagt   1020
actgcatatg aggaaattta ccacctggca aatgtccgca tgaaggagac agaggggtaa   1080
tgcatgatgt ggactgacca acctactgag agtgattcag agaaatggga ggagtaaaat   1140
gcaatgaagc aatggctggt ggacggacca tatatataca gtagtatgta attattttct   1200
ctgaatccct gtgtctctgt gacccactca ataaacacat cagccaaaag caatactgtt   1260
cggaggtatc gtgggggctc tgtaatctct gtgacccact caataaacag atcggccaaa   1320
agcagtgcta ctggtaattt cctctcttga ctgttgttgt tggtcttcct cggcctccac   1380
tgaaactctg tgttcactgg taaagtttag catatgttca tgatcgctca attttgtagg   1440
cgaggcttca ggttctgtta cagtttaagt atgctcatga actgaaacta tgctttccct   1500
agtactagta cccaaaggca ttcagtattc acgaccaaac cgaagttttc aaactgaacg   1560
gagggattca attattcacc ggttgcaaag atgaacgcta gtgaggaaaa ttaatagtgt   1620
cattgcctga taaatgcatg aaggagagag agatggtaaa tgaccggcag gcgcatgagg   1680
gacctacaat tattgtctct gaatgaccca ctgaacagtt acatgtgcca aaagcagtac   1740
gtactattca gaggcatcgt gggggctctg tatctcttga cttgctgttg ttggtcttcc   1800
tctgtatctc agtcctcatc tccaccactg acagagtcct cttctccgtt gcgctgcctg   1860
gaataaggtc gatcctcctc gttgtttggt gatctcctcc aacctccgag ctcgcccctg   1920
ccaactgact gccagaggcc tttgacaccc gtggaggtat atttcctgtc gatttctttc   1980
cagctgaagt aaaaagtacg cttggatcaa aaaacttact tctcctgctt cactgcttgc   2040
ttgggagtct gatcgatttg tgttggttga atcatttggg gtggcagtgg aacagcaagc   2100
aagaaccatg gagtttccga tcattattca gagcagcacg catcgaatcc actgacccgg   2160
ttagcggcct ggtaactttg tctcatcttt cttgctactg taatatattt cacatccata   2220
ccttcttgtt aatctgctga ccctcccttc cagatcgaga gagagagcgc cccttccaac   2280
tcacgcctgt gctgtggagg tatatttcca gtctattttt ccaacctcgt tgcatgaagc   2340
ttggatctaa aaaaggactt ctcctgcgcg cgtggttggc agtgaaatag caagaagatg   2400
aactatcgag tttccagtcg ttcagagcat gatgcatcaa atccactgaa atctttttttg  2460
tctcatcttt tttgctattc tgctctactg aaatttttga catccacacc ttctagttaa   2520
tctgctgatt tgctagatta taaattcttg ttcctctttg cagttggtaa taattgaatc   2580
actccgtcct gtttggtaga ggagagaggg gtaaatgcat gaagcatggc agatggactg   2640
atcgtataca gtacaagtaa ttattttctc tgaatccctg tctctctgtg acccactcac   2700
tcaataaaca catcagccaa aagcgctact gctcagaggt atcaatcatt atctctcttg   2760
actgctgtta ttggtcttcc tctgctagta attattgtat ccactgagtg ctgccatccc   2820
tccctctcat ctcagtcttc tccattgcgc tgccttgttg cctccgagct cgcccctgcc   2880
agctgactgc cagagacatt tgtggtatgt tactttcctg tcagatttgt ttccagcgaa   2940
actagcaatg cttggatcta aaaggtgacc tctccaggat ggtagtggaa tagcaacaag   3000
tagaaccatg gagtttccgg tcattattca gagcacgttg catcggctag cggcctggta   3060
```

-continued

```
aatttctccc tcccatcttt cttgctgttc ttattaatct gctgattgct agattatacc   3120
aagtttttat tcttccagat cctccgccgc cgtgtgccct tctcacgcat ctggcctctg   3180
gtgccctggc actgcttcca cttcattgtc ctgctctttt ctgctctgcc tatgaagcat   3240
caaaggtgaa gcatcgaggt gagcttggtc cagatctaga tatgttttag cttggcgact   3300
ctcagttttt gagcttggat tgcattcagc tcctgacatt tatggatctg cagttttcca   3360
gctgattggt ccagatagct gctcctgctg atctcatgga ggtcgtcacg ggtgccatgg   3420
gcagcctgct ccccaagctg ggcaagctgc tcctggagga gtacaagctg cacaagggcg   3480
tcaaggaaaa tatcgaggac ctccggaagg agcttgagag catgaacctt gccctcgtca   3540
agattgatga ggtgccgcgg gaccagctcg acagacaaga caagctctgg gcagatgatg   3600
tcagagatct ctcctacaag attgaggatg tcgtcgacaa gttcctcatg cacgtcgacc   3660
gcattcagcc tgacgacacc accaatggat tcaaggggct catgaagagg acggccgagt   3720
tgttcaagaa aggcaaggat cggaatcgga tagggcacgc gatgaagggc atccaggagg   3780
aacttcagaa ggtggctgct aggcgtgaca ggaacaaggt cgacggtatg gctcctaata   3840
ctagggaagc agttgttatc gatcctcgtc tccgtgctct gtacacagaa gcgacagagc   3900
tggttggcat ctacgggaag agggatcagg acctcatgag tttgctctcc ctggagggcg   3960
gcgatgcctc taacaagaga ctgaagaagg tctccattgt tggatttggt ggattgggca   4020
agaccactct tgctagagca gtatacaaca agattaaagg tgttttcgat tgtcgggcat   4080
ttgtccccgt cggccggaac cccaacatca agaaggtttt tagggatatc ctcattgatc   4140
tcggcaactc taactcagat cttgcattat tggatgaaag gcagcttatc aacaagcttc   4200
atgaattcct cgagaacaag aggtatgcgt tacttccagc tgaaacaact atactttgat   4260
atgttcgttt ctatgctagc tatccaacac tattatgagt ttatgataaa tacattgtaa   4320
ccatcacaga gaaggctggt tcagaataat ttttcattta ggtcagtttc aagactgtat   4380
aagcatatat gtttgatcct cctctcctct atctgaataa gtagtaaact acttctcatt   4440
gcattagttg cggtggctta aatttaatgc cattggtcta ggaaatccat ctcagcattt   4500
atacatttca tcagagatat aagtaatgag cataataaga gttgtactgg ataatacacc   4560
aaaatgtaaa ggaaagaact cacttagttc tttctttatc ctaacccacc ccattaaaac   4620
aaagatcaaa tggtgcatcg tgcaccaaag gctgcccttt ttctcttaat acaccaagaa   4680
gttaaatttg ctctttgata tcacattcta tttccccttt tcgccttgtt tagaaactta   4740
ctatcagcag aatatactcg aaagggaaat gtcatgtaaa atttgagtct ccgggagttt   4800
tatcagcggc catacagtat attggtgggc aaatcagtgc tccgatcttt ccaatagatc   4860
tacctaacca ttgtaatatt tgaaatgttg tattccatcc gatccaaaat aagtgtcgtg   4920
gttttagttc aaacgcttat tttggatcag atggagtaac aaattaatcg tacttctatc   4980
tatgtcgttg atgcaacaat ttgctcttcg tgttttactc ccttgaatct taaatttgta   5040
ttcattttat tcatcatctg actggcagtg cataatgcac agttcttaat atcagattat   5100
cgagattgag acgcctgatt cttattagtt tgtttctgaa tatgtgcact tatagatgtg   5160
tagttccacc cacatattct tatggcccta agctttgtga tgtgtataaa ccttacactg   5220
atactctgaa ctaatgtagg tatctggtca taattgatga tatatgggat gaaaaattgt   5280
gggaatacat caacttggct ttctccgaca ggaataatct aggcagtcgg ctaatcacca   5340
caacccgcat tgtcagtgtc tccaattcat gttgctcgtc ggctaatgat tcaatttatc   5400
```

-continued

```
aaatgaaacc tctttctact gatgattcca gaaggctctt ccataagaga atatttcccg   5460
acaagagtgc atgtccaaat gaatttgaac aagtgtctaa tgatatattg aaaaaatgtg   5520
gtggagtacc actagccatc attactattg ctagtgcttt ggccagtggc cagcaggtga   5580
aaccaaagcg tgagtgggat attctgctcc agtcccttgg ctctggacta acagaagata   5640
acagtttaga ggagatgcgt agaatactct ctttcagcta ttataatcta ccatatgatc   5700
taaaaacctg tctattgtac ctatgtatat atccagaaga tcacgagatt aatagagata   5760
aactgatatg gaagtgggtg gccgaaggat ttgtcctcca tggaaatcaa ggaactagcc   5820
tgtttttgct cggattaaat tacttcaacg aactcatcaa tagaagtatg atccagccaa   5880
tatatgatcc tctcggccag gtatatgctt gccgtgtaca tgatatggtt ctggacctta   5940
tctgcaactt gtcacatgaa gcaaagtttg ttaatgtatt cgatggcact gggaatatca   6000
tgtcttcaca aagtaatgtt cgtcgtttgt cccttcagaa taaaatggaa gatcatcaag   6060
ccaagcctct cacaaatatc atgagtatgt cacgagtgag gtcaattact atctttccac   6120
ctgctgttag tatcatgcca gctctgtcaa ggtttgaagt tctgcgtgta cttgatatgt   6180
cggactgtaa ccttggggaa agtagcagcc tgcagcctaa cctcaagggt gttggacact   6240
taattcacct aaggtaccta ggtctatcag gtaccggaat tagtaaactc ccggctgaga   6300
taggaaccct gcagtttctg gaggtgttgg atcttggata caatcatgag ctagatgaat   6360
tgccgtccac tctttttaaa ttgagaaggt taatctacct aaatgttcgg ttctataagg   6420
tggttccaac tcctggtgtg ttgcagaatc tgacatccat agaagtgttg aggggggctct   6480
tggtctctct gaacatcatt gcacaagagc ttggcaacct ggcaaggctg agggagcttg   6540
agattcgctt caaggatggt agtttggatt tgtatgaagg tttcgtgaag tctctgtgca   6600
acctacatca tatcgaaagc ctaagtatta gttgcaattc caaagaaaca tcttttgaac   6660
tgatggatct cttgggagaa cgctgggtgc ctcctgtaca tctccgcgaa tttgtgtcat   6720
acatccccag ccaaatctct gcactgcgag ggtggataga gagagacccc tcgcatctct   6780
cgaacctctc cgagttaatc ctcacgtcag tgaaggaggt gcagcaggag gacgtggaaa   6840
tcattggggg gttgctgtcc cttcgcaatc tctggataac gagcacccac caaacacagc   6900
ggctgctagt catccgtgca gatgggttcc gctgtatgct aaactttgag ttgaattgtg   6960
gatcagccgc acaaataatg tttgaatcag gagctttgcc gagggcggaa agagttgagt   7020
tcagtctcgg cgtgcgggtg gcgaaagagg atggtaaccg tggtttcaac ttgggcctgc   7080
aggggaacct gctctccctt cggcgtggtg tccggatttg gatgtattgt ggtggagcga   7140
gggttgggga ggccaaggaa gcggaggctg cggtgaggca cgccctcgac gcccatccca   7200
gccatcccct gattttgatt gagatgaggc cgcgtataca agaaggtact catgtcgcac   7260
ctaactactc acgctcaact cccatcccaa tcatccccga ttacgtatat gttttttttcg   7320
aatgatggac tgaccttatt actctctgca ttgattttga tctctgaatc taccaagatg   7380
ctcatgatga cgatttgtgt gaggacgagg aggagaactg atttctgatc cagagcgact   7440
cacaatattg catcagatgt gctctcgggt atgtaacaga tatttgcctg ttatgttttc   7500
catcttttat ttgcctgtta tgttcgcctg ctataacggc tgtatggaaa ttagaaacag   7560
attaatgtat ttacaaaaat tgctagacat aagtatctga ccagaaaact gaacttgccc   7620
gatctgtttt atggcaaggg ctgatgaaag ataagaatta ttttatgcaa atttgtagaa   7680
ggatagttag taatggggaa tttgggatag aactagattt tgggaagatt tatggacagg   7740
gggtgctgtt tttggtgacc agtactccag gttatacaac ttatcaatat ataagcatat   7800
```

```
ctctgtagct agaatgctgc acgctaattt cactgctcta aaatttagag ggggtctgta   7860
tggtgaaacg gctgagctat cgtatcgatt cttgctgatc gtcaaggtta gtcttgagga   7920
atgagcaaga ttcatgtaga tgatcccata aaaaaggtta atgtaaatgg cttttagaga   7980
agaatgttgt ggttagcatt caccactatt tctgttgatt cagaaatgag caagatcata   8040
gtatttttgt ggttagcatt cagaaattat cggcacagtt aatctgaagc gtcgaggtag   8100
tgtggtatag gaaagtgtct tttgtatacc acactacctc gacgcttcag attagcatgg   8160
agggactttg tgcttgagtg atgaatttca gggtaaaggt aggaatatgg tttctgctag   8220
ggtagtggct attatttggt ctatatggaa actgaggaat cataattgct tgaaaaatat   8280
tttccctatc gatattagat gttttattgg gctatcttac agagaagaat tgcacgatat   8340
gcaggtagca ggggcgtggg acggtggggg ttactgctgg tggcaacgga gatgaatgtt   8400
tcccaaacat tttgggtggg cgctcgccgt gcaaaggttt cgaacattct ggaggttgtg   8460
tgatgagctt cttttaaatg gcactcagct tgcagaaaga gatattcctt ggttttgtaa   8520
cgaataagta aggtgttggg gcgaattgat ccttacaagg atagctttgc tttgcttcag   8580
ttgagggtca ttgttgctcc tctgttttgc atgttgttgt tacatgggag ggctagccca   8640
tgacatgctg gtgtattttg ttttttaagc tgagccggac aaacctatgg gtgtattatc   8700
agtttcctga tgaatgaaat ggggggctca cctgagctcc ttaatttgaa taaaaactgc   8760
ggttcactgt tgggatttgt tacttgaaaa atatttacaa gttctaccaa catgtctctg   8820
ttacagacaa atggaaagcg tgcttccaac taacaagcat gtgtagccca ctgtagcaaa   8880
ttattttcgt atttttgaaa gtgtcgtcgc aaagccaatt gaagcctaaa ttcgacagtg   8940
gaggaaaggg cctagaacga aaagggccat atatgtttgt acagaaagtg gcagagctac   9000
aaagaaaaga tggagagcac aaatgagagt tccagggctt ccatttccac agtaaaggta   9060
tttcttgact atagttgtgc ttagacaaga gctaatgggg gagtgaaact ctatggtagt   9120
taacaataac ataagccgat gaatggtcca ctaactaacg atcctttagt tcctaatgtc   9180
tctcagtccg ttcagtccgt aatgcttact taaccttctt atgttcagga ctagctctgc   9240
tttttctcc actgtcacga gtatttgaat gcgatggaag gtgttctaac taggagatct   9300
tgagagaaga tggagcggta tatatgtgca cacgacggaa ccagtatgag tgttcacagc   9360
tagaagttat tgggtaagta ctattttaca ttgacgccac gtctttatat tttgtaatgg   9420
tttaagatag taatttggca atggcaaagc atatacaatt tttaccatta atgatgccac   9480
atatatctag attatagaat aataactacg acccatgaat aaaaaattta aagttttgac   9540
accgaaatat attagactgt atatcttgta gtgtacacta gaagatgcat tttgtaggag   9600
cgcggacatt taactaccca tgcatcttac tcaagtcggt tgtttattta ttgtaacccc   9660
gatggtcaag tctgttcgac acaaacaaaa atagtgagga aagggcctag aacgaaaagg   9720
gctatatatg tttgtacaga aagtggcaga gctacaaaga aaagatggag agcacaaaaa   9780
cttcaaattc tgaaccatat gtactattga gtgaattata tatttattat gctaccaaat   9840
tggaaactat tgttaaaccg tgagctagca acaatcaatg cctttgttgt gaacttgtat   9900
aaactataaa ggtggccttt gttgtgaacc agtaaaatgc aaagaacaat ggctttccat   9960
ggtataaact ataaaacaac aagatttcgg tgtggattat ttatgctaaa gtccatagat  10020
gatgacgtaa gtgaaattta ggggaagaaa tttgggaaga ttcagagaaa tttacctata  10080
cagcttgcag gggtgcatg cagattcaga gaaggacctc atcaggttgg ctcgccgctg  10140
```

-continued

```
ctagctacgt cgcctcgcgg agtcatggtg ggagcactag gcggctgatg tgtgcaactg  10200

tgccggtgtg ccggaagccg gccaccgcga tggccggcgg ctgctgtgtg cctgtgtcgc  10260

ggctgctccg cttctcaatg ttgcgttacg tgccttcgtt gttttctctg agaaacagtg  10320

ctggataatc acagtgctgc gactttgatg tgagcttcgc tgggctgagg tgtgcgttgt  10380

acttgctcaa tgccggtcag cagttgtggg ctgggctcaa cgtaaattta tttcttgctc  10440

caaca                                                              10445
```

<210> SEQ ID NO 9
<211> LENGTH: 2874
<212> TYPE: DNA
<213> ORGANISM: Aegilops tauschii

<400> SEQUENCE: 9

```
atggaggtcg tcacgggtgc catgggcagc ctgctcccca agctgggcaa gctgctcctg     60

gaggagtaca agctgcacaa gggcgtcaag gaaaatatcg aggacctccg gaaggagctt    120

gagagcatga accttgccct cgtcaagatt gatgaggtgc cgcgggacca gctcgacaga    180

caagacaagc tctgggcaga tgatgtcaga gatctctcct acaagattga ggatgtcgtc    240

gacaagttcc tcatgcacgt cgaccgcatt cagcctgacg acaccaccaa tggattcaag    300

gggctcatga agaggacggc cgagttgttc aagaaaggca aggatcggaa tcggataggg    360

cacgcgatga agggcatcca ggaggaactt cagaaggtgg ctgctaggcg tgacaggaac    420

aaggtcgacg gtatggctcc taatactagg gaagcagttg ttatcgatcc tcgtctccgt    480

gctctgtaca cagaagcgac agagctggtt ggcatctacg ggaagaggga tcaggacctc    540

atgagtttgc tctccctgga gggcggcgat gcctctaaca agagactgaa gaaggtctcc    600

attgttggat ttggtggatt gggcaagacc actcttgcta gagcagtata caacaagatt    660

aaaggtgttt tcgattgtcg ggcatttgtc cccgtcggcc ggaaccccaa catcaagaag    720

gtttttaggg atatcctcat tgatctcggc aactctaact cagatcttgc attattggat    780

gaaaggcagc ttatcaacaa gcttcatgaa ttcctcgaga acaagaggta tctggtcata    840

attgatgata tatgggatga aaaattgtgg gaatacatca acttggcttt ctccgacagg    900

aataatctag gcagtcggct aatcaccaca acccgcattg tcagtgtctc caattcatgt    960

tgctcgtcgg ctaatgattc aatttatcaa atgaaacctc tttctactga tgattccaga   1020

aggctcttcc ataagagaat atttcccgac aagagtgcat gtccaaatga atttgaacaa   1080

gtgtctaatg atatattgaa aaaatgtggt ggagtaccac tagccatcat tactattgct   1140

agtgctttgg ccagtggcca gcaggtgaaa ccaaagcgtg agtgggatat tctgctccag   1200

tcccttggct ctggactaac agaagataac agtttagagg agatgcgtag aatactctct   1260

ttcagctatt ataatctacc atatgatcta aaaacctgtc tattgtacct atgtatatat   1320

ccagaagatc acgagattaa tagagataaa ctgatatgga agtgggtggc cgaaggattt   1380

gtcctccatg gaaatcaagg aactagcctg tttttgctcg gattaaatta cttcaacgaa   1440

ctcatcaata gaagtatgat ccagccaata tatgatcctc tcggccaggt atatgcttgc   1500

cgtgtacatg atatggttct ggaccttatc tgcaacttgt cacatgaagc aaagtttgtt   1560

aatgtattcg atggcactgg gaatatcatg tcttcacaaa gtaatgttcg tcgtttgtcc   1620

cttcagaata aaatggaaga tcatcaagcc aagcctctca caaatatcat gagtatgtca   1680

cgagtgaggt caattactat ctttccacct gctgttagta tcatgccagc tctgtcaagg   1740

tttgaagttc tgcgtgtact tgatatgtcg gactgtaacc ttggggaaag tagcagcctg   1800
```

```
cagcctaacc tcaagggtgt tggacactta attcacctaa ggtacctagg tctatcaggt   1860
accggaatta gtaaactccc ggctgagata ggaaccctgc agtttctgga ggtgttggat   1920
cttggataca atcatgagct agatgaattg ccgtccactc tttttaaatt gagaaggtta   1980
atctacctaa atgttcggtt ctataaggtg gttccaactc ctggtgtgtt gcagaatctg   2040
acatccatag aagtgttgag gggctcttg gtctctctga acatcattgc acaagagctt   2100
ggcaacctgg caaggctgag ggagcttgag attcgcttca aggatggtag tttggatttg   2160
tatgaaggtt tcgtgaagtc tctgtgcaac ctacatcata tcgaaagcct aagtattagt   2220
tgcaattcca aagaaacatc ttttgaactg atggatctct tgggagaacg ctgggtgcct   2280
cctgtacatc tccgcgaatt tgtgtcatac atccccagcc aaatctctgc actgcgaggg   2340
tggatagaga gagacccctc gcatctctcg aacctctccg agttaatcct cacgtcagtg   2400
aaggaggtgc agcaggagga cgtggaaatc attgggggt tgctgtccct tcgcaatctc    2460
tggataacga gcacccacca aacacagcgg ctgctagtca tccgtgcaga tgggttccgc   2520
tgtatgctaa actttgagtt gaattgtgga tcagccgcac aaataatgtt tgaatcagga   2580
gctttgccga gggcggaaag agttgagttc agtctcggcg tgcgggtggc gaaagaggat   2640
ggtaaccgtg gtttcaactt gggcctgcag gggaacctgc tctcccttcg gcgtggtgtc   2700
cggatttgga tgtattgtgg tggagcgagg gttggggagg ccaaggaagc ggaggctgcg   2760
gtgaggcacg ccctcgacgc ccatcccagc catcccctga ttttgattga gatgaggccg   2820
cgtatacaag aagatgctca tgatgacgat ttgtgtgagg acgaggagga gaac         2874
```

<210> SEQ ID NO 10
<211> LENGTH: 4026
<212> TYPE: DNA
<213> ORGANISM: Aegilops tauschii

<400> SEQUENCE: 10

```
atggaggtcg tcacgggtgc catgggcagc ctgctcccca agctgggcaa gctgctcctg     60
gaggagtaca agctgcacaa gggcgtcaag gaaaatatcg aggacctccg gaaggagctt    120
gagagcatga accttgccct cgtcaagatt gatgaggtgc cgcgggacca gctcgacaga    180
caagacaagc tctgggcaga tgatgtcaga gatctctcct acaagattga ggatgtcgtc    240
gacaagttcc tcatgcacgt cgaccgcatt cagcctgacg acaccaccaa tggattcaag    300
gggctcatga agaggacggc cgagttgttc aagaaaggca aggatcggaa tcggataggg    360
cacgcgatga agggcatcca ggaggaactt cagaaggtgg ctgctaggcg tgacaggaac    420
aaggtcgacg gtatggctcc taatactagg gaagcagttg ttatcgatcc tcgtctccgt    480
gctctgtaca cagaagcgac agagctggtt ggcatctacg ggaagaggga tcaggacctc    540
atgagtttgc tctccctgga gggcggcgat gcctctaaca agagactgaa gaaggtctcc    600
attgttggat ttggtggatt gggcaagacc actcttgcta gagcagtata caacaagatt    660
aaaggtgttt tcgattgtcg ggcatttgtc cccgtcggcc ggaaccccaa catcaagaag    720
gtttttaggg atatcctcat tgatctcggc aactctaact cagatcttgc attattggat    780
gaaaggcagc ttatcaacaa gcttcatgaa ttcctcgaga acaagaggta tgcgttactt    840
ccagctgaaa caactatact ttgatatgtt cgtttctatg ctagctatcc aacactatta    900
tgagtttatg ataaatacat tgtaaccatc acagagaagg ctggttcaga ataatttttc    960
atttaggtca gtttcaagac tgtataagca tatatgtttg atcctcctct cctctatctg   1020
```

-continued

```
aataagtagt aaactacttc tcattgcatt agttgcggtg gcttaaattt aatgccattg   1080
gtctaggaaa tccatctcag catttataca tttcatcaga gatataagta atgagcataa   1140
taagagttgt actggataat acaccaaaat gtaaaggaaa gaactcactt agttctttct   1200
ttatcctaac ccaccccatt aaaacaaaga tcaaatggtg catcgtgcac caaaggctgc   1260
cctttttctc ttaatacacc aagaagttaa atttgctctt tgatatcaca ttctatttcc   1320
ccttttcgcc ttgtttagaa acttactatc agcagaatat actcgaaagg gaaatgtcat   1380
gtaaaatttg agtctccggg agttttatca gcggccatac agtatattgg tgggcaaatc   1440
agtgctccga tctttccaat agatctacct aaccattgta atatttgaaa tgttgtattc   1500
catccgatcc aaaataagtg tcgtggtttt agttcaaacg cttattttgg atcagatgga   1560
gtaacaaatt aatcgtactt ctatctatgt cgttgatgca acaatttgct cttcgtgttt   1620
tactcccttg aatcttaaat ttgtattcat tttattcatc atctgactgg cagtgcataa   1680
tgcacagttc ttaatatcag attatcgaga ttgagacgcc tgattcttat tagtttgttt   1740
ctgaatatgt gcacttatag atgtgtagtt ccacccacat attcttatgg ccctaagctt   1800
tgtgatgtgt ataaacctta cactgatact ctgaactaat gtaggtatct ggtcataatt   1860
gatgatatat gggatgaaaa attgtgggaa tacatcaact tggctttctc cgacaggaat   1920
aatctaggca gtcggctaat caccacaacc cgcattgtca gtgtctccaa ttcatgttgc   1980
tcgtcggcta atgattcaat ttatcaaatg aaacctcttt ctactgatga ttccagaagg   2040
ctcttccata agagaatatt tcccgacaag agtgcatgtc caaatgaatt tgaacaagtg   2100
tctaatgata tattgaaaaa atgtggtgga gtaccactag ccatcattac tattgctagt   2160
gctttggcca gtggccagca ggtgaaacca aagcgtgagt gggatattct gctccagtcc   2220
cttggctctg gactaacaga agataacagt ttagaggaga tgcgtagaat actctctttc   2280
agctattata atctaccata tgatctaaaa acctgtctat tgtacctatg tatatatcca   2340
gaagatcacg agattaatag agataaactg atatggaagt gggtggccga aggatttgtc   2400
ctccatggaa atcaaggaac tagcctgttt ttgctcggat taaattactt caacgaactc   2460
atcaatagaa gtatgatcca gccaatatat gatcctctcg gccaggtata tgcttgccgt   2520
gtacatgata tggttctgga ccttatctgc aacttgtcac atgaagcaaa gtttgttaat   2580
gtattcgatg gcactgggaa tatcatgtct tcacaaagta atgttcgtcg tttgtccctt   2640
cagaataaaa tggaagatca tcaagccaag cctctcacaa atatcatgag tatgtcacga   2700
gtgaggtcaa ttactatctt tccacctgct gttagtatca tgccagctct gtcaaggttt   2760
gaagttctgc gtgtacttga tatgtcggac tgtaaccttg gggaaagtag cagcctgcag   2820
cctaacctca agggtgttgg acacttaatt cacctaaggt acctaggtct atcaggtacc   2880
ggaattagta aactcccggc tgagatagga accctgcagt ttctggaggt gttggatctt   2940
ggatacaatc atgagctaga tgaattgccg tccactcttt ttaaattgag aaggttaatc   3000
tacctaaatg ttcggttcta taaggtggtt ccaactcctg gtgtgttgca gaatctgaca   3060
tccatagaag tgttgagggg gctcttggtc tctctgaaca tcattgcaca agagcttggc   3120
aacctggcaa ggctgaggga gcttgagatt cgcttcaagg atggtagttt ggatttgtat   3180
gaaggtttcg tgaagtctct gtgcaaccta catcatatcg aaagcctaag tattagttgc   3240
aattccaaag aaacatcttt tgaactgatg gatctcttgg gagaacgctg ggtgcctcct   3300
gtacatctcc gcgaatttgt gtcatacatc cccagccaaa tctctgcact gcgagggtgg   3360
atagagagag acccctcgca tctctcgaac ctctccgagt taatcctcac gtcagtgaag   3420
```

```
gaggtgcagc aggaggacgt ggaaatcatt ggggggttgc tgtcccttcg caatctctgg   3480

ataacgagca cccaccaaac acagcggctg ctagtcatcc gtgcagatgg gttccgctgt   3540

atgctaaact ttgagttgaa ttgtggatca gccgcacaaa taatgtttga atcaggagct   3600

ttgccgaggg cggaaagagt tgagttcagt ctcggcgtgc gggtggcgaa agaggatggt   3660

aaccgtggtt tcaacttggg cctgcagggg aacctgctct cccttcggcg tggtgtccgg   3720

atttggatgt attgtggtgg agcgagggtt ggggaggcca aggaagcgga ggctgcggtg   3780

aggcacgccc tcgacgccca tcccagccat cccctgattt tgattgagat gaggccgcgt   3840

atacaagaag gtactcatgt cgcacctaac tactcacgct caactcccat cccaatcatc   3900

cccgattacg tatatgtttt tttcgaatga tggactgacc ttattactct ctgcattgat   3960

tttgatctct gaatctacca agatgctcat gatgacgatt tgtgtgagga cgaggaggag   4020

aactga                                                              4026
```

<210> SEQ ID NO 11
<211> LENGTH: 958
<212> TYPE: PRT
<213> ORGANISM: Aegilops tauschii

<400> SEQUENCE: 11

```
Met Glu Val Val Thr Gly Ala Met Gly Ser Leu Leu Pro Lys Leu Gly
1               5                   10                  15

Lys Leu Leu Leu Glu Glu Tyr Lys Leu His Lys Gly Val Lys Glu Asn
            20                  25                  30

Ile Glu Asp Leu Arg Lys Glu Leu Glu Ser Met Asn Leu Ala Leu Val
        35                  40                  45

Lys Ile Asp Glu Val Pro Arg Asp Gln Leu Asp Arg Gln Asp Lys Leu
    50                  55                  60

Trp Ala Asp Asp Val Arg Asp Leu Ser Tyr Lys Ile Glu Asp Val Val
65                  70                  75                  80

Asp Lys Phe Leu Met His Val Asp Arg Ile Gln Pro Asp Asp Thr Thr
                85                  90                  95

Asn Gly Phe Lys Gly Leu Met Lys Arg Thr Ala Glu Leu Phe Lys Lys
            100                 105                 110

Gly Lys Asp Arg Asn Arg Ile Gly His Ala Met Lys Gly Ile Gln Glu
        115                 120                 125

Glu Leu Gln Lys Val Ala Ala Arg Arg Asp Arg Asn Lys Val Asp Gly
    130                 135                 140

Met Ala Pro Asn Thr Arg Glu Ala Val Val Ile Asp Pro Arg Leu Arg
145                 150                 155                 160

Ala Leu Tyr Thr Glu Ala Thr Glu Leu Val Gly Ile Tyr Gly Lys Arg
                165                 170                 175

Asp Gln Asp Leu Met Ser Leu Leu Ser Leu Glu Gly Gly Asp Ala Ser
            180                 185                 190

Asn Lys Arg Leu Lys Lys Val Ser Ile Val Gly Phe Gly Gly Leu Gly
        195                 200                 205

Lys Thr Thr Leu Ala Arg Ala Val Tyr Asn Lys Ile Lys Gly Val Phe
    210                 215                 220

Asp Cys Arg Ala Phe Val Pro Val Gly Arg Asn Pro Asn Ile Lys Lys
225                 230                 235                 240

Val Phe Arg Asp Ile Leu Ile Asp Leu Gly Asn Ser Asn Ser Asp Leu
                245                 250                 255
```

-continued

```
Ala Leu Leu Asp Glu Arg Gln Leu Ile Asn Lys Leu His Glu Phe Leu
            260                 265                 270

Glu Asn Lys Arg Tyr Leu Val Ile Ile Asp Asp Ile Trp Asp Glu Lys
        275                 280                 285

Leu Trp Glu Tyr Ile Asn Leu Ala Phe Ser Asp Arg Asn Asn Leu Gly
    290                 295                 300

Ser Arg Leu Ile Thr Thr Thr Arg Ile Val Ser Val Ser Asn Ser Cys
305                 310                 315                 320

Cys Ser Ser Ala Asn Asp Ser Ile Tyr Gln Met Lys Pro Leu Ser Thr
                325                 330                 335

Asp Asp Ser Arg Arg Leu Phe His Lys Arg Ile Phe Pro Asp Lys Ser
            340                 345                 350

Ala Cys Pro Asn Glu Phe Glu Gln Val Ser Asn Asp Ile Leu Lys Lys
        355                 360                 365

Cys Gly Gly Val Pro Leu Ala Ile Ile Thr Ile Ala Ser Ala Leu Ala
    370                 375                 380

Ser Gly Gln Gln Val Lys Pro Lys Arg Glu Trp Asp Ile Leu Leu Gln
385                 390                 395                 400

Ser Leu Gly Ser Gly Leu Thr Glu Asp Asn Ser Leu Glu Glu Met Arg
                405                 410                 415

Arg Ile Leu Ser Phe Ser Tyr Tyr Asn Leu Pro Tyr Asp Leu Lys Thr
            420                 425                 430

Cys Leu Leu Tyr Leu Cys Ile Tyr Pro Glu Asp His Glu Ile Asn Arg
        435                 440                 445

Asp Lys Leu Ile Trp Lys Trp Val Ala Glu Gly Phe Val Leu His Gly
    450                 455                 460

Asn Gln Gly Thr Ser Leu Phe Leu Leu Gly Leu Asn Tyr Phe Asn Glu
465                 470                 475                 480

Leu Ile Asn Arg Ser Met Ile Gln Pro Ile Tyr Asp Pro Leu Gly Gln
                485                 490                 495

Val Tyr Ala Cys Arg Val His Asp Met Val Leu Asp Leu Ile Cys Asn
            500                 505                 510

Leu Ser His Glu Ala Lys Phe Val Asn Val Phe Asp Gly Thr Gly Asn
        515                 520                 525

Ile Met Ser Ser Gln Ser Asn Val Arg Arg Leu Ser Leu Gln Asn Lys
    530                 535                 540

Met Glu Asp His Gln Ala Lys Pro Leu Thr Asn Ile Met Ser Met Ser
545                 550                 555                 560

Arg Val Arg Ser Ile Thr Ile Phe Pro Pro Ala Val Ser Ile Met Pro
                565                 570                 575

Ala Leu Ser Arg Phe Glu Val Leu Arg Val Leu Asp Met Ser Asp Cys
            580                 585                 590

Asn Leu Gly Glu Ser Ser Ser Leu Gln Pro Asn Leu Lys Gly Val Gly
        595                 600                 605

His Leu Ile His Leu Arg Tyr Leu Gly Leu Ser Gly Thr Gly Ile Ser
    610                 615                 620

Lys Leu Pro Ala Glu Ile Gly Thr Leu Gln Phe Leu Glu Val Leu Asp
625                 630                 635                 640

Leu Gly Tyr Asn His Glu Leu Asp Glu Leu Pro Ser Thr Leu Phe Lys
                645                 650                 655

Leu Arg Arg Leu Ile Tyr Leu Asn Val Arg Phe Tyr Lys Val Val Pro
            660                 665                 670

Thr Pro Gly Val Leu Gln Asn Leu Thr Ser Ile Glu Val Leu Arg Gly
```

-continued

```
        675                 680                 685

Leu Leu Val Ser Leu Asn Ile Ile Ala Gln Glu Leu Gly Asn Leu Ala
    690                 695                 700

Arg Leu Arg Glu Leu Glu Ile Arg Phe Lys Asp Gly Ser Leu Asp Leu
705                 710                 715                 720

Tyr Glu Gly Phe Val Lys Ser Leu Cys Asn Leu His His Ile Glu Ser
                725                 730                 735

Leu Ser Ile Ser Cys Asn Ser Lys Glu Thr Ser Phe Glu Leu Met Asp
            740                 745                 750

Leu Leu Gly Glu Arg Trp Val Pro Pro Val His Leu Arg Glu Phe Val
        755                 760                 765

Ser Tyr Ile Pro Ser Gln Ile Ser Ala Leu Arg Gly Trp Ile Glu Arg
    770                 775                 780

Asp Pro Ser His Leu Ser Asn Leu Ser Glu Leu Ile Leu Thr Ser Val
785                 790                 795                 800

Lys Glu Val Gln Gln Glu Asp Val Glu Ile Ile Gly Gly Leu Leu Ser
                805                 810                 815

Leu Arg Asn Leu Trp Ile Thr Ser Thr His Gln Thr Gln Arg Leu Leu
            820                 825                 830

Val Ile Arg Ala Asp Gly Phe Arg Cys Met Leu Asn Phe Glu Leu Asn
        835                 840                 845

Cys Gly Ser Ala Ala Gln Ile Met Phe Glu Ser Gly Ala Leu Pro Arg
    850                 855                 860

Ala Glu Arg Val Glu Phe Ser Leu Gly Val Arg Val Ala Lys Glu Asp
865                 870                 875                 880

Gly Asn Arg Gly Phe Asn Leu Gly Leu Gln Gly Asn Leu Leu Ser Leu
                885                 890                 895

Arg Arg Gly Val Arg Ile Trp Met Tyr Cys Gly Gly Ala Arg Val Gly
            900                 905                 910

Glu Ala Lys Glu Ala Glu Ala Ala Val Arg His Ala Leu Asp Ala His
        915                 920                 925

Pro Ser His Pro Leu Ile Leu Ile Glu Met Arg Pro Arg Ile Gln Glu
    930                 935                 940

Asp Ala His Asp Asp Asp Leu Cys Glu Asp Glu Glu Glu Asn
945                 950                 955
```

STEM RUST RESISTANCE GENES AND METHODS OF USE

CROSS-REFERENCE TO RELATED APPLICATIONS

This application is the U.S. National Stage of International Application PCT/US2019/013430, filed Jan. 14, 2019, which designates the U.S. and was published by the International Bureau in English on Jul. 18, 2019, and which claims the benefit of U.S. Provisional Patent Application No. 62/616,553, filed Jan. 12, 2018, all of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070294-0150SEQLST.TXT, created on Jan. 13, 2019 and having a size of 103 kilobytes, and is filed concurrently with the specification. The sequence listing contained in this ASCII formatted document is part of the specification and is herein incorporated by reference in its entirety.

FIELD OF THE INVENTION

The present invention relates to the fields of gene isolation and plant improvement, particularly to enhancing the resistance of plants to plant disease through the use of disease resistance genes.

BACKGROUND OF THE INVENTION

Plant diseases cause significant yield losses in world-wide wheat production. Among the most damaging diseases of wheat are the rusts. Wheat stem rust caused by *Puccinia graminis* f. sp. *tritici* is one of the most devastating diseases affecting wheat production today. While wheat plants comprising resistance (R) genes against *Puccinia graminis* f. sp. *tritici* have proven effective in limiting the agronomic losses caused by wheat stem rust, new races of *Puccinia graminis* f. sp. *tritici* have appeared recently for which the R genes are not effective. While pesticides can be used to control wheat stem rust, pesticides are expensive and at odds with the sustainable intensification of agriculture, and in developing countries, pesticides are simply unaffordable for subsistence farmers.

The sustainable intensification of agriculture will require increased use of genetic solutions instead of chemical solutions (e.g. pesticides) to protect crops against pathogens and pests (Jones et al. (2014) *Philos. T. Roy. Soc. B* 369: 20130087). Wild relatives of domesticated crops, such as wheat, contain an immense diversity of useful R genes that are a valuable resource for sustainable disease control. However, traditional methods for introducing R genes typically involve long breeding timelines to break linkage to deleterious alleles of other genes. Furthermore, R genes can be overcome within a few seasons when deployed one at a time (McDonald and Linde (2002) *Annu. Rev. Phytopathol.* 40:349-379). Molecular cloning, however, makes it possible to avoid linkage drag and simultaneously introduce multiple R genes (Dangl et al. (2013) *Science* 341:746-751), which should delay resistance-breaking pathogen race evolution and thus, provide more durable resistance (McDonald and Linde (2002) *Annu. Rev. Phytopathol.* 40:349-379).

While traditional map-based cloning methods have been employed to isolate R genes from plants, many plant genomes carry large chromosomal regions that are inaccessible to traditional map-based cloning due to suppressed recombination (Gaut et al. (2007) *Nature Rev. Genet.* 8:77-84) and wheat is no exception. Therefore, new, complementary approaches not relying on recombination need to be applied to identify additional R genes in crop plants and their undomesticated relatives.

BRIEF SUMMARY OF THE INVENTION

The present invention provides nucleic acid molecules for resistance (R) genes that are known to confer upon a plant resistance to at least one strain of the pathogen that causes wheat stem rust, *Puccinia graminis* f. sp. *tritici*. In one embodiment, the present invention provides nucleic acid molecules comprising the R gene, SrTA1662, and variants thereof including, for example, orthologs and non-naturally occurring variants.

The present invention further provides plants, plant cells, and seeds comprising in their genomes one or more polynucleotide constructs of the invention. The polynucleotide constructs comprise a nucleotide sequence encoding a resistance (R) protein of the present invention. Such R proteins are encoded by the R genes of the present invention. In a preferred embodiment, the plants and seeds are transgenic wheat plants and seeds that have been transformed with one or more polynucleotide constructs of the invention. Preferably, such wheat plants comprise enhanced resistance to at least one strain of the pathogen that causes wheat stem rust, *Puccinia graminis* f. sp. *tritici*, when compared to the resistance of a control wheat plant that does not comprise the polynucleotide construct.

The present invention provides methods for enhancing the resistance of a wheat plant to wheat stem rust. Such methods comprise introducing into at least one wheat plant cell a polynucleotide construct comprising a nucleotide sequence of an R gene of the present invention. In some embodiments, the polynucleotide construct or part thereof is stably incorporated into the genome of the plant cell, and in other embodiments, the polynucleotide construct is not stably incorporated into the genome of the wheat plant cell. The methods for enhancing the resistance of a wheat plant to wheat stem rust can optionally further comprise regenerating the wheat plant cell into a wheat plant that comprises in its genome the polynucleotide construct. Preferably, such a wheat plant comprises enhanced resistance to wheat stem rust caused by at least one race of *Puccinia graminis* f. sp. *tritici*, relative to a control wheat plant.

The present invention additionally provides methods for identifying a wheat plant that displays newly conferred or enhanced resistance to wheat stem rust. The methods comprise detecting in the wheat plant the presence of at least one R gene, particularly SrTA1662.

Methods of using the wheat plants of the present invention in agricultural crop production to limit wheat stem rust are also provided. The methods comprise planting a wheat seed produced by a wheat plant of the present invention, wherein the wheat seed comprises at least one R gene nucleotide sequence of the present invention. The methods further comprise growing a wheat plant under conditions favorable for the growth and development of the wheat plant, and optionally harvesting at least one seed from the wheat plant.

Additionally provided are plants, plant parts, seeds, plant cells, other host cells, expression cassettes, and vectors comprising one or more of the nucleic acid molecules of the present invention.

SEQUENCE LISTING

Figure 1:
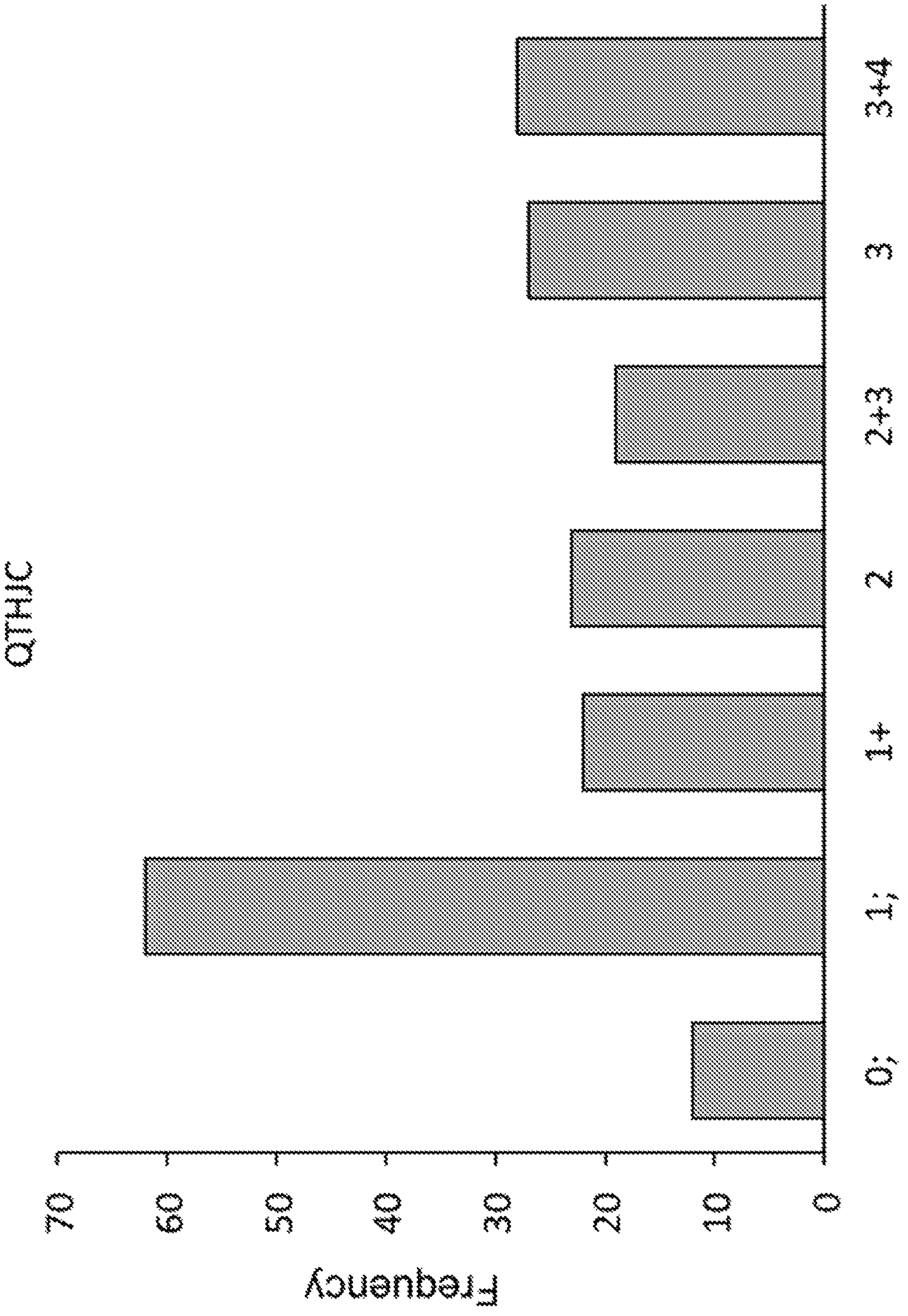
FIG. 1 is a graphical representation of seedling stage disease distribution for the *Puccinia graminis* f. sp. *tritici* (PGT) races QTHJC across 151 non-redundant *Aegilops tauschii* spp. *strangulata* accessions. The number scale at the bottom of each bar indicates the disease variation ranging from resistant (0; to 1;), moderately resistant (1+ to 2), moderately susceptible (2+3) to susceptible (3 to 3+4).

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the 7.64 kb RenSeq contig comprising the open reading frame of the R gene, SrTA1662, from *Aegilops* (*Ae.*) *tauschii* accession TA1662.

SEQ ID NO: 2 sets forth the nucleotide sequence comprising a portion of the R gene, SrTA1662, from *Ae. tauschii* accession TA1662.

SEQ ID NO: 3 sets forth the nucleotide sequence of the coding region of the cDNA of a portion of the R gene, SrTA1662 (SEQ ID NO: 2), from *Ae. tauschii* accession TA1662. If desired, a stop codon (e.g. TAA, TAG, or TGA) can be operably linked to the 3' end of nucleic acid molecule comprising SEQ ID NO: 3. The native stop codon of this cDNA is TGA.

SEQ ID NO: 4 sets forth the predicted amino acid sequence of the nucleotide sequence set forth in SEQ ID NO: 3.

SEQ ID NO: 5 sets forth the linear nucleotide sequence of the pBW_0150 vector described in Example 2 below. The pBW_0150 vector comprises a promoter and terminator region from Sr33 (Periyannan et al. (2013) *Science* 341:786-788) and the open reading frame of SrTA1662. While SEQ ID NO: 5 is provided as a linear nucleotide sequence, the pBW_0150 vector is a circular DNA molecule.

SEQ ID NO: 6 sets forth the nucleotide sequence of the open reading frame in the pBW_0150 vector (SEQ ID NO: 5) comprising a domesticated nucleotide sequence encoding SRTA1662 that is described below in Example 2.

SEQ ID NO: 7 sets forth the amino acid sequence of the R protein encoded by the SrTA1662 coding sequence in the pBW_0150 vector having the sequence set forth in SEQ ID NO: 5.

SEQ ID NO: 8 sets forth the nucleotide sequence comprising the R gene, SrTA1662, from *Ae. tauschii* accession TA1662. For the nucleotide sequence, the promoter region is nucleotides 1-3395, the protein coding region (from the first nucleotide of the stop codon to the last nucleotide of the stop codon and containing introns) is nucleotides 3396-7421, and the terminator regions is nucleotides 7422-10,445.

SEQ ID NO: 9 sets forth the nucleotide sequence of the coding region of the cDNA of SrTA1662 from *Ae. tauschii* accession TA1662. If desired, a stop codon (e.g. TAA, TAG, or TGA) can be operably linked to the 3' end of nucleic acid molecule comprising SEQ ID NO: 9. The native stop codon of this cDNA is TGA.

SEQ ID NO: 10 sets forth the nucleotide sequence of the open reading frame of the SrTA1662 (SEQ ID NO: 8). This sequence is the portion of the genomic sequence of SrTA1662 beginning at first nucleotide of the start codon and ending at the last nucleotide of the stop codon. This sequence contains introns.

SEQ ID NO: 11 sets forth the amino acid sequence of the R protein, SRTA1662, encoded by SrTA1662 from *Ae. tauschii* accession TA1662.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to the isolation of plant resistance (R) genes, particularly R genes that confer upon a wheat plant resistance to wheat stem rust caused by *Puccinia graminis* f. sp. *tritici*. As disclosed hereinbelow, NLR resistance gene enrichment sequencing (RenSeq) (Jupe et al. (2013) *Plant J.* 76:530-544) was employed in the isolation of the R gene, SrTA1662, from a panel of 151 geographically and genetically diverse *Aegilops* (*Ae.*) *tauschii* accessions, the diploid D genome progenitor of hexaploid bread wheat.

The present invention provides nucleic acid molecules comprising the nucleotide sequences of R genes, particularly the nucleotide sequence of SrTA1662 and naturally occurring (e.g. orthologs and allelic variants) and synthetic or artificial (i.e. non-naturally occurring) variants thereof. Such nucleotide sequences of R genes, which are also referred to herein as R gene nucleotide sequences, encode R proteins. R gene nucleotide sequences of the invention include, but not limited to, wild-type R genes comprising a native promoter and the 3' adjacent region comprising the coding region, cDNA sequences, and nucleotide sequences comprising only the coding region. Examples of such R gene nucleotide sequences include the nucleotide sequences set forth in SEQ ID NOS: 1, 8, 9, and 10 and variants thereof. In embodiments in which the native R gene promoter is not used to drive the expression of the nucleotide sequence encoding the R protein, a heterologous promoter can be operably linked to a nucleotide sequence encoding an R protein of the invention to drive the expression of nucleotide sequence encoding an R protein in a plant.

Preferably, the R proteins of the invention are functional R proteins that are capable of conferring on a wheat plant comprising the R protein enhanced resistance to wheat stem rust caused by at least one race of *Puccinia graminis* f. sp. *tritici*. In certain embodiments, the R proteins of the present invention comprise broad-spectrum resistance to multiple races of *Puccinia graminis* f. sp. *tritici* such as, for example, the R protein encoded by SrTA1662.

The present invention further provides transgenic plants comprising a polynucleotide construct which comprise an R gene nucleotide sequence of the invention. In some embodiments, the polynucleotide construct is stably incorporated into the genome of the plant, and in other embodiments, the plant is transformed by a transient transformation method and the polynucleotide construct is not stably incorporated into the genome of the plant. Methods for both the stable and transient transformation of plants are disclosed elsewhere herein or otherwise known in the art. In a preferred embodiment of the invention, the transgenic plants are wheat plants that comprise enhanced resistance to wheat stem rust caused by at least one race of *Puccinia graminis* f. sp. *tritici*.

In certain embodiments, a transgenic plant of the invention comprises a polynucleotide construct comprising a nucleotide sequence encoding an R protein and a heterologous promoter that is operably linked for expression of the nucleotide sequence encoding an R protein. The choice of heterologous promoter can depend on a number of factors such as, for example, the desired timing, localization, and pattern of expression as well as responsiveness to particular biotic or abiotic stimulus. Promoters of interest include, but are not limited to, pathogen-inducible, constitutive, tissue-preferred, wound-inducible, and chemical-regulated promoters.

In certain embodiments of the invention, the transgenic plant, particularly a transgenic wheat plant, can comprise one, two, three, four, five, six, or more nucleotide sequences encoding an R protein. Typically, but not necessarily, the two or more R proteins will be different from each other. For the present invention, an R protein is different from another R protein when the two R proteins have non-identical amino acid sequences. In certain embodiments of the invention, each of the different R proteins for wheat stem rust has one or more differences in resistance characteristics such as, for example, resistance against a different race and/or group of races of *Puccinia graminis* f. sp. *tritici*. It is recognized that by combining two, three, four, five, six, or more nucleotide sequences with each nucleotide sequence encoding a different R protein for wheat stem rust, a wheat plant can be produced that comprises broad spectrum resistance against multiple races of *Puccinia graminis* f. sp. *tritici*. Such a wheat plant finds use in agriculture in regions where multiple races of *Puccinia graminis* f. sp. *tritici* are known to occur.

Examples of wheat stem rust R genes that can be combined in a single wheat plant with an nucleotide sequence of the present invention include Sr22 (WO 2017/024053), Sr26, Sr32, Sr33 (GenBank Accession No. KF031299.1), Sr35 (GenBank Accession No. KC573058.1), Sr39, Sr40, Sr45 (WO 2017/024053), Sr47, Sr50, and the adult plant resistance gene Sr57/Lr34 (GenBank Accession No. FJ436983.1) and Sr55/Lr67.

A transgenic plant of the invention comprising multiple R genes can be produced by transforming a plant that already comprises one or more other R gene nucleotide sequences with a polynucleotide construct comprising an R gene nucleotide sequence of the invention including, for example, an SrTA1662 nucleotide sequence or variant thereof. Such a plant that already comprises one or more other R gene nucleotide sequences can comprise R genes that are native to the genome or the plant, that were introduced into the plant via sexual reproduction, or that were introduced by transforming the plant or a progenitor thereof with an R gene nucleotide sequence. Alternatively, the one or more other R gene nucleotide sequences can be introduced into a transgenic plant of the invention, which already comprises a polynucleotide construct of the invention, by, for example, transformation or sexual reproduction.

In other embodiments, two or more different R gene sequences can be introduced into a plant by stably transforming the plant with a polynucleotide construct or vector comprising two or more R gene nucleotide sequences. It is recognized that such an approach can be preferred for plant breeding as it is expected that the two or more R gene nucleotide sequences will be tightly linked and thus, segregate as a single locus. Alternatively, a polynucleotide construct of the present invention can be incorporated into the genome of a plant in the immediate vicinity of another R gene nucleotide sequence using homologous recombination-based genome modification methods that are described elsewhere herein or otherwise known in the art.

The present invention further provides methods for enhancing the resistance of a wheat plant to wheat stem rust. The methods comprise introducing a polynucleotide construct of the invention into at least one wheat plant cell. In certain embodiments, the polynucleotide construct is stably incorporated into the genome of wheat plant cell. If desired, the methods can further comprise regenerating the plant cell into a wheat plant comprising in its genome the polynucleotide construct. Preferably, such a regenerated wheat plant comprises enhanced resistance to wheat stem rust caused by at least one race of *Puccinia graminis* f. sp. *tritici*, relative to the resistance of a control wheat plant to wheat stem rust caused by the same race or races of *Puccinia graminis* f. sp. *tritici*. If desired, the method can further comprise producing a wheat plant, as described above, comprising one, two, three, four, five, six, or more nucleotide sequences encoding an R protein, preferably each nucleotide sequence encoding a different R protein.

The wheat plants disclosed herein find use in methods for limiting wheat stem rust in agricultural crop production, particularly in regions where wheat stem rust is prevalent. The methods of the invention comprise planting a wheat seed produced by a wheat plant of the present invention, wherein the wheat seed comprises at least one R gene nucleotide sequence of the present invention. The methods further comprise growing a wheat plant under conditions favorable for the growth and development of the wheat plant therefrom, and optionally harvesting at least one seed from the wheat plant.

The present invention additionally provides methods for identifying a wheat plant that displays newly conferred or enhanced resistance to wheat stem rust. The methods find use in breeding wheat plants for resistance to wheat stem rust. Such resistant wheat plant find use in the agricultural production of wheat seeds. The methods comprise detecting in a wheat plant the presence of at least one R gene of the present invention, particularly SrTA1662. In some embodiments of the invention, detecting the presence of the R gene comprises detecting the entire R gene in genomic DNA isolated from the wheat plant. In preferred embodiments, however, detecting the presence of an R gene comprises detecting the presence of at least one marker within the R gene. In other embodiments of the invention, detecting the presence of an R gene comprises detecting the presence of the R protein encoded by the R gene using, for example, immunological detection methods involving antibodies specific to the R protein.

In the methods for identifying a wheat plant that displays newly conferred or enhanced resistance to wheat stem rust, detecting the presence of the R gene in wheat can involve one or more of the following molecular biology techniques that are disclosed elsewhere herein or otherwise known in the art including, but not limited to, isolating genomic DNA and/or RNA from the wheat plant, amplifying nucleic acid molecules comprising the R gene and/or marker therein by PCR amplification, sequencing nucleic acid molecules comprising the R gene and/or marker, identifying the R gene, the marker, or a transcript of the R gene by nucleic acid hybridization, and conducting an immunological assay for the detection of the R protein encoded by the R gene. It is recognized that oligonucleotide probes and PCR primers can be designed to identity the R genes of the present invention and that such probes and PCR primers can be utilized in methods disclosed elsewhere herein or otherwise known in the art to rapidly identify in a population of wheat plants one or more wheat plants comprising the presence of an R gene of the present invention.

Depending on the desired outcome, the polynucleotide constructs of the invention can be stably incorporated into the genome of the plant cell or not stably incorporated into the genome of the plant cell. If, for example, the desired outcome is to produce a stably transformed plant with enhanced resistance to wheat stem rust caused by at least one race of *Puccinia graminis* f. sp. *tritici*, then the polynucleotide construct can be, for example, fused into a plant transformation vector suitable for the stable incorporation of the polynucleotide construct into the genome of the plant cell. Typically, the stably transformed plant cell will be regenerated into a transformed plant that comprises in its genome the polynucleotide construct. Such a stably transformed plant is capable of transmitting the polynucleotide construct to progeny plants in subsequent generations via sexual and/or asexual reproduction. Plant transformation vectors, methods for stably transforming plants with an introduced polynucleotide construct and methods for plant regeneration from transformed plant cells and tissues are generally known in the art for both monocotyledonous and dicotyledonous plants or described elsewhere herein.

The present invention provides nucleotide acid molecules comprising R genes. Preferably, such R genes are capable of conferring upon a host plant, particularly a wheat plant, enhanced resistance to at least one race of the pathogen that causes wheat stem rust, *Puccinia graminis* f. sp. *tritici*. Thus, such R genes find use in limiting wheat stem rust caused by *Puccinia graminis* f. sp. *tritici* in agricultural production. The R genes of the present invention include, but are not limited to, the R genes whose nucleotide sequences are disclosed herein but also include orthologs and other variants that are capable of conferring to a wheat plant resistance to wheat stem rust caused by at least one race of *Puccinia graminis* f sp. *tritici*. Methods are known in the art or otherwise disclosed herein for determining resistance of a plant to stem rust caused by at least one race of *Puccinia graminis* f. sp. *tritici*.

The methods of the present invention find use in producing wheat plants with enhanced resistance to stem rust caused by at least one race of *Puccinia graminis* f. sp. *tritici*. Typically, the methods of the present invention will enhance or increase the resistance of the subject wheat plant to the least one race of *Puccinia graminis* f. sp. *tritici* by at least 25%, 50%, 75%, 100%, 150%, 200%, 250%, 500% or more when compared to the resistance of a control wheat plant to same race or races of *Puccinia graminis* f. sp. *tritici*. Unless stated otherwise or apparent from the context of a use, a control plant for the present invention is a plant that does not comprise the polynucleotide construct of the present invention. Preferably, the control plant is essentially identical (e.g. same species, subspecies, and variety) to the plant comprising the polynucleotide construction of the present invention except the control does not comprise the polynucleotide construct. In some embodiments, the control will comprise a polynucleotide construct but not comprise the one or more R gene sequences that are in a polynucleotide construction of the present invention.

Additionally, the present invention provides transformed plants, seeds, and plant cells produced by the methods of present invention and/or comprising a polynucleotide construct of the present invention. Also provided are progeny plants and seeds thereof comprising a polynucleotide construct of the present invention. The present invention also provides seeds, vegetative parts, and other plant parts produced by the transformed plants and/or progeny plants of the invention as well as food products and other agricultural products produced from such plant parts that are intended to be consumed or used by humans and other animals including, but not limited to pets (e.g., dogs and cats) and livestock (e.g., pigs, cows, chickens, turkeys, and ducks).

Non-limiting examples of the compositions and methods of the present invention are as follows:

1. A nucleic acid molecule comprising a nucleotide sequence selected from the group consisting of:

(a) the nucleotide sequence set forth in SEQ ID NO: 1, 8, 9, or 11;

(b) a nucleotide sequence encoding the amino acid sequence set forth in SEQ ID NO: 11, and optionally, wherein the nucleotide sequence is not naturally occurring;

(c) a nucleotide sequence having at least 85% sequence identity to at least one of the nucleotide sequences set forth in (a), wherein the nucleic acid molecule is capable of conferring resistance to stem rust to a wheat plant comprising the nucleic acid molecule and optionally, wherein the nucleotide sequence is not naturally occurring; and (d) a nucleic acid molecule comprising a nucleotide sequence encoding an amino acid sequence having at least 85% sequence identity to at least one amino acid sequence set forth in (b), wherein the nucleic acid molecule is capable of conferring resistance to stem rust to a wheat plant comprising the nucleic acid molecule and optionally, wherein the nucleotide sequence is not naturally occurring.

2. The nucleic acid molecule of embodiment 1, wherein the nucleic acid molecule is an isolated nucleic acid molecule.

3. The nucleic acid molecule of embodiment 1 or 2, wherein the nucleic acid molecule of (c) or (d) encodes a protein comprising a coiled-coil domain, a nucleotide-binding domain, and a leucine-rich repeat domain.

4. The nucleic acid molecule of embodiment 3, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 11.

5. An expression cassette comprising the nucleic acid molecule of any one of embodiments 1-4 and an operably linked heterologous promoter.

6. A vector comprising the nucleic acid molecule of any one of embodiments 1-4 or the expression cassette of embodiment 5.

7. A vector of embodiment 6, further comprising an additional wheat stem rust resistance gene.

8. The vector of embodiment 7, wherein the additional wheat stem rust resistance gene is selected from the group consisting of Sr22, Sr26, Sr32, Sr33, Sr39, Sr40, Sr45, Sr47, and Sr50.

9. A host cell comprising the nucleic acid molecule of any one of embodiments 1-5, the expression cassette of embodiment 5, or the vector of any one of embodiments 6-8.

10. The host cell of embodiment 9, wherein the host cell is a plant cell, a bacterium, a fungal cell, or an animal cell.

11. The host cell of embodiment 9 or 10, wherein the host cell is not *Aegilops tauschii.*

12. A plant comprising the nucleic acid molecule of any one of embodiments 1-5, the expression cassette of embodiment 5, or the vector of any one of embodiments 6-8.

13. The plant of embodiment 12, wherein the plant is a wheat plant.

14. The plant of embodiment 12 or 13, wherein the plant is not *Aegilops tauschii.*

15. A transgenic plant or seed comprising stably incorporated in its genome a polynucleotide construct comprising a nucleotide sequence selected from the group consisting of:

(a) the nucleotide sequence set forth in SEQ ID NO: 1, 8, 9, or 10;

(b) a nucleotide sequence encoding the amino acid sequence set forth in SEQ ID NO: 11, and optionally, wherein the nucleotide sequence is not naturally occurring;

(c) a nucleotide sequence having at least 85% sequence identity to at least one of the nucleotide sequences set forth in (a), wherein the nucleic acid molecule is capable of conferring resistance to stem rust to a wheat plant comprising the nucleic acid molecule and optionally, wherein the nucleotide sequence is not naturally occurring; and (d) a nucleic acid molecule comprising a nucleotide sequence encoding an amino acid sequence having at least 85% sequence identity to at least one amino acid sequence set forth in (b), wherein the nucleic acid molecule is capable of conferring resistance to stem rust to a wheat plant comprising the nucleic acid molecule and optionally, wherein the nucleotide sequence is not naturally occurring.

16. The transgenic plant or seed of embodiment 15, wherein the nucleic acid molecule of (c) or (d) encodes a protein comprising a coiled-coil domain, a nucleotide-binding domain, and a leucine-rich repeat domain.

17. The transgenic plant or seed of embodiment 16, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 11.

18. The transgenic plant or seed of any one of embodiments 15-17, wherein the polynucleotide construct further comprises a promoter operably linked for the expression of the nucleotide sequence in a plant.

19. The transgenic plant or seed of embodiment 18, wherein the promoter is selected from the group consisting of pathogen-inducible, constitutive, tissue-preferred, wound-inducible, and chemical-regulated promoters.

20. The transgenic plant or seed of embodiment any one of embodiments 15-19, wherein the transgenic plant is a wheat plant and the transgenic seed is wheat seed.

21. The transgenic plant or seed of embodiment 20, wherein the transgenic plant or seed comprises enhanced resistance to wheat stem rust caused by at least one race of *Puccinia graminis* f. sp. *tritici*, relative to a control wheat plant.

22. The transgenic plant or seed of embodiment 20 or 21, wherein the polynucleotide construct comprises at least two nucleotide sequences encoding an R protein for wheat stem rust.

23. The transgenic plant or seed of embodiment 22, wherein each of the at least two nucleotide sequences encoding an R protein for wheat stem rust encodes a different R protein for wheat stem rust.

24. A method for enhancing the resistance of a wheat plant to wheat stem rust, the method comprising introducing a polynucleotide construct into at least one wheat plant cell, the polynucleotide construct comprising a nucleotide sequence selected from the group consisting of:

(a) the nucleotide sequence set forth in SEQ ID NO: 1, 8, 9, or 10;

(b) a nucleotide sequence encoding the amino acid sequence set forth in SEQ ID NO: 11;

(c) a nucleotide sequence having at least 85% sequence identity to at least one of the nucleotide sequences set forth in (a), wherein the nucleic acid molecule is capable of conferring resistance to stem rust to a wheat plant comprising the nucleic acid molecule; and (d) a nucleic acid molecule comprising a nucleotide sequence encoding an amino acid sequence having at least 85% sequence identity to at least one amino acid sequence set forth in (b), wherein the nucleic acid molecule is capable of conferring resistance to stem rust to a wheat plant comprising the nucleic acid molecule.

25. The method of embodiment 24, wherein the nucleic acid molecule of (c) or (d) encodes a protein comprising a coiled-coil domain, a nucleotide-binding domain, and a leucine-rich repeat domain.

26. The method of embodiment 25, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 11.

27. The method of any one of embodiments 24-26, wherein the polynucleotide construct is stably incorporated into the genome of the plant cell.

28. The method of any one of embodiments 24-27, wherein the wheat plant cell is regenerated into a wheat plant comprising in its genome the polynucleotide construct.

29. The method of any one of embodiments 24-28, wherein the polynucleotide construct further comprises a promoter operably linked for the expression of the nucleotide sequence in a plant.

30. The method of embodiment 29, wherein the promoter is selected from the group consisting of pathogen-inducible, constitutive, tissue-preferred, wound-inducible, and chemical-regulated promoters.

31. The method of any one of embodiments 21-30, wherein the wheat plant comprising the polynucleotide construct comprises enhanced resistance to wheat stem rust caused by at least one race of *Puccinia graminis* f. sp. *tritici*, relative to a control wheat plant.

32. The method of any one of embodiments 24-31, wherein the polynucleotide construct comprises at least two nucleotide sequences encoding an R protein for wheat stem rust.

33. The method of embodiment 32, wherein each of the at least two nucleotide sequences encoding an R protein for wheat stem rust encodes a different R protein for wheat stem rust.

34. A wheat plant produced by the method of any one of embodiments 24-33.

35. A seed of the wheat plant of embodiment 34, wherein the seed comprises the polynucleotide construct.

36. A method of limiting wheat stem rust in agricultural crop production, the method comprising planting a wheat seed according to any one of embodiments 20-23 and 35 and growing a wheat plant under conditions favorable for the growth and development of the wheat plant.

37. The method of embodiment 36, further comprising harvesting at least one seed from the wheat plant.

38. Use of the wheat plant or seed of any one of embodiments 20-23, 34, and 35 in agriculture.

39. A human or animal food product produced using the wheat plant or seed of any one of embodiments 20-23, 34, and 35.

40. A polypeptide comprising an amino acid sequence selected from the group consisting of:

(a) the amino acid sequence encoded by the nucleotide sequence set forth in SEQ ID NO: 1, 8, 9, or 10;

(b) the amino acid sequence set forth in SEQ ID NO: 11; and (c) an amino acid sequence having at least 85% sequence identity to the amino acid sequence set forth in SEQ ID NO: 11, wherein a polypeptide comprising the amino acid sequence is capable of conferring resistance to stem rust to a wheat plant comprising the polypeptide, and optionally, wherein the polypeptide is not naturally occurring.

41. The polypeptide of embodiment 40, wherein the polypeptide of (c) comprises a coiled-coil domain, a nucleotide-binding domain, and a leucine-rich repeat domain.

42. The polypeptide of embodiment 41, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 11.

43. A method for identifying a wheat plant that displays newly conferred or enhanced resistance to wheat stem rust, the method comprising detecting in the wheat plant the presence of the R gene, SrTA1662.

44. The method of embodiment 43, wherein the presence of the R gene is detected by detecting at least one marker within SrTA1662.

45. The method of any one of embodiment 43 or 44, wherein SrTA1662 comprises or consists of, the nucleotide sequence set forth in SEQ ID NO: 1, 8, 9, or 10, or a nucleotide sequence encoding SEQ ID NO: 11.

46. The method of any one of embodiments 43-45, wherein detecting the presence of the R gene comprises a member selected from the group consisting of PCR amplification, nucleic acid sequencing, nucleic acid hybridization, and an immunological assay for the detection of the R protein encoded by the R gene.

47. A wheat plant identified by the process of any one of embodiments 43-46.

48. A seed of the wheat plant of embodiment 47.

49. A vector comprising the nucleotide sequence set forth in SEQ ID NO: 8, 9, or 10.

Additional embodiments of the methods and compositions of the present invention are described elsewhere herein.

The methods of the invention can be used to enhance the resistance of a wheat plant to wheat stem rust, particularly stem rust caused by at least one race of *Puccinia graminis* f. sp. *tritici*. Preferred plants of the invention are wheat plants, wheat seeds, wheat plant parts, and wheat plant cells. As used herein, the term “wheat plant” generally refers to a plant that is a member of the *Triticum* genus or a member of another genus within the Triticeae tribe, particularly a member of another genus that is capable of producing interspecific hybrids with at least one *Triticum* sp. Examples of such another genus within the Triticeae tribe are *Aegilops* and *Secale*.

The wheat plants of the present invention include, for example, domesticated and non-domesticated plants. The wheat plants of the present invention include, but are not limited to, the following *Triticum, Aegilops* and *Secale* species: *T. aestivum, T. monococcum, T. turgidum, T. boeoticum, T. timopheevii*, and *T. urartu, Ae. tauschii, S. cereale*, and hybrids thereof. Examples of *T. aestivum* subspecies included within the present invention are *aestivum* (common wheat), *compactum* (club wheat), *macha* (*macha* wheat), *vavilovi* (*vavilovi* wheat), *spelta*, and *sphaecrococcum* (shot wheat). Examples of *T. turgidum* subspecies included within the present invention are *turgidum, carthlicum, dicoccom, durum, paleocoichicum, polonicum, turanicum*, and *dicoccoides*. Examples of *T. monococcum* subspecies included within the present invention are *monococcum* (einkorn) and *aegilopoides*. In one embodiment of the present invention, the wheat plant is a member of the *Triticum turgidum* species; and in particular, a member of the Durum subspecies, for example, a Ciccio, Colosseo, or Utopia cultivar. It is recognized that a wheat plant of the present invention can be a domesticated wheat plant or a non-domesticated wheat plant.

The present invention also encompasses triticale plants, triticale plant parts, and tritcale plant cells comprising an R gene of the invention. As used herein, a “triticale plant” refers to a plant that is created by crossing a rye plant (*Secale cereale*) with either a tetraploid wheat plant (e.g. *Triticum turgidum*) or a hexaploid wheat plant (e.g. *Triticum aestivum*). The present invention also includes seeds produced by the triticale plants described herein and methods for controlling weeds in the vicinity of the triticale plants described herein. As used herein, the term “wheat plant” encompasses triticale plants unless stated otherwise or apparent from the context of use.

The term “wheat plant” is intended to encompass wheat plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like. The present invention also includes seeds produced by the wheat plants of the present invention.

In one embodiment of the invention, the nucleotide sequences encoding R proteins have at least about 80%, 85%, 90%, 91%, 92%, 93%, 94%, 95%, 96%, 97%, 98%, 99% or more sequence identity to the entire nucleotide sequence set forth in SEQ ID NO: 1, 8, 9, and/or 10 or to a fragment thereof. In another embodiment of the invention, the nucleotide sequences encoding R proteins have at least about 80%, 85%, 90%, 91%, 92%, 93%, 94%, 95%, 96%, 97%, 98%, 99% or more sequence identity to the entire nucleotide sequence set forth in SEQ ID NO: 11 or to a fragment thereof.

The present invention encompasses isolated or substantially purified polynucleotide (also referred to herein as "nucleic acid molecule", "nucleic acid" and the like) or protein (also referred to herein as "polypeptide") compositions including, for example, polynucleotides and proteins comprising the sequences set forth in the accompanying Sequence Listing as well as variants and fragments of such polynucleotides and proteins. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the full-length or native protein. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

Polynucleotides that are fragments of a native R polynucleotide comprise at least 16, 20, 50, 75, 100, 125, 150, 175, 200, 300, 400, 500, 1000, 2000, 5000, 7500, or 10000 contiguous nucleotides, or up to the number of nucleotides present in a full-length R polynucleotide disclosed herein.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the R proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an R protein of the invention. Generally, variants of a particular polynucleotide of the invention will have at least about 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. In certain embodiments of the invention, variants of a particular polynucleotide of the invention will have at least about 80%, 85%, 90%, 91%, 92%, 93%, 94%, 95%, 96%, 97%, 98%, 99% or more sequence identity to at least one nucleotide sequence selected from the group consisting of SEQ ID NOS: 1, 8, 9, and 10, and optionally comprises a non-naturally occurring nucleotide sequence that differs from the nucleotide sequence set forth in SEQ ID NO: 1, 8, 9, and/or 10 by at least one nucleotide modification selected from the group consisting of the substitution of at least one nucleotide, the addition of at least one nucleotide, and the deletion of at least one nucleotide.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptide of SEQ ID NO: 11 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 86%, 87%, 88%, 89%, 90%, 91%, 92%, 93%, 94%, 95%, 96%, 97%, 98%, 99% or more sequence identity. In certain embodiments of the invention, variants of a particular polypeptide of the invention will have at least about 80%, 85%, 90%, 91%, 92%, 93%, 94%, 95%, 96%, 97%, 98%, 99% or more sequence identity to the amino acid sequence set forth SEQ ID NO: 11, and optionally comprises a non-naturally occurring amino acid sequence that differs from the amino acid set forth in SEQ ID NO: 11 by at least one amino acid modification selected from the group consisting of the substitution of at least one amino acid, the addition of at least one amino acid, and the deletion of at least one amino acid. "Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of an R protein will have at least about 80%, 85%, 86%, 87%, 88%, 89%, 90%, 91%, 92%, 93%, 94%, 95%, 96%, 97%, 98%, 99% or more sequence identity to the amino acid sequence for the native protein (e.g. the amino acid sequence set forth in SEQ ID NO: 11) as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. Methods for mutagenesis and polynucleotide alterations are well known in the art. See, for example, Kunkel (1985) *PNAS* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant and other variant forms. Likewise, the proteins of the invention encompass both naturally occurring proteins as well as variations and modified forms thereof. More preferably, such variants confer to a plant or part thereof comprising the variant enhanced resistance wheat stem rust caused by at least one race of *Puccinia graminis* f. sp. *tritici*. In some embodiments, the mutations that will be made in the DNA encoding the variant will not place the sequence out of reading frame. Optimally, the mutations will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed herein below.

For example, a wheat plant that is susceptible to wheat stem rust caused by a particular race of *Puccinia graminis* f. sp. *tritici* can be transformed with an SrTA1662 polynucleotide, regenerated into a transformed or transgenic plant comprising the polynucleotide, and tested for resistance to wheat stem rust caused by the particular race of *Puccinia graminis* f. sp. *tritici* using standard resistance assays known in the art or described elsewhere herein. Preferred variant polynucleotides and polypeptides of the present invention confer or are capable of conferring upon a wheat plant enhanced resistance to at least one race of *Puccinia graminis* f. sp. *tritici* that is known to cause wheat stem rust in a susceptible wheat plant.

Variant polynucleotides and proteins also encompass sequences and proteins derived from a mutagenic and recombinogenic procedure such as DNA shuffling. Strategies for such DNA shuffling are known in the art. See, for example, Stemmer (1994) *PNAS* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *PNAS* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 86%, 87%, 88%, 89%, 90%, 91%, 92%, 93%, 94%, 95%, 96%, 97%, 98%, 99%, or greater sequence identity. Functions of orthologs are often highly conserved among species. Thus, isolated polynucleotides that encode R proteins and which hybridize under stringent conditions to at least one of the R proteins disclosed herein or otherwise known in the art, or to variants or fragments thereof, are encompassed by the present invention.

In one embodiment, the orthologs of the present invention have coding sequences comprising at least 80%, 85%, 86%, 87%, 88%, 89%, 90%, 91%, 92%, 93%, 94%, 95%, 96%, 97%, 98%, 99%, or greater nucleotide sequence identity to a nucleotide sequence selected from the group consisting of the nucleotide sequences set forth in SEQ ID NOS: 1, 8, 9, and 10, and/or encode proteins comprising at least 80%, 85%, 86%, 87%, 88%, 89%, 90%, 91%, 92%, 93%, 94%, 95%, 96%, 97%, 98%, 99%, or greater amino acid sequence identity to the amino acid sequence set forth in SEQ ID NO: 11.

Like other NLR proteins, SRTA1662 protein comprises certain conserved domains. In SRTA1662 from *Aegilops tauschii* accession TA1662 (comprising the amino acid sequence set forth in SEQ ID NO: 11), the conserved domains include, for example, a coiled-coil domain (amino acids 10 to 122), a nucleotide-binding domain (amino acids 200 to 468) and a leucine-rich repeat domain (amino acids 580 to 742). Preferably, variant SRTA1662 proteins of the present invention comprise a coiled-coil domain, a nucleotide-binding domain, and a leucine-rich repeat domain corresponding to the domains of SRTA1662 set forth above.

In some embodiments, variant SRTA1662 proteins of the present invention comprise a higher percentage of amino acid sequence identity to one, two, or three of such conserved domains than to the full-length amino acid sequence of the SRTA1662 (SEQ ID NO: 11) or protein disclosed herein. Preferably, such variants comprise a corresponding domain or domains having at least 95%, 96%, 97%, 98%, 99%, or 100% sequence identity to one, two, or three of the domains of SRTA1662 set forth above and further comprise an amino acid sequence having at least 80%, 85%, 86%, 87%, 88%, 89%, 90%, 91%, 92%, 93%, 94%, 95%, 96%, 97%, 98%, or 99% identity to the amino acid sequence set forth in SEQ ID NO: 11.

It is recognized that domains in variant SRTA1662 proteins corresponding to those conserved domains of SRTA1662 set forth above, as well as any particular conserved amino acids therein, can be identified by methods known to those of skill in the art or disclosed elsewhere herein such as, for example, multiple sequence alignment. It is further recognized that the positions of such conserved domains and conserved amino acids within a particular variant SRTA1662 protein can vary from the positions in the amino acid sequence set forth in SEQ ID NO: 11 and that through methods such as, for example, multiple sequence alignment, the corresponding positions of such conserved domains and conserved amino acids can be determined for any variant SRTA1662 protein of the present invention.

Preferably, the variant SRTA1662 proteins of the present invention and the polynucleotides encoding them confer, or are capable of conferring upon a wheat plant comprising such a protein and/or polynucleotide, enhanced resistance to at least one race of *Puccinia graminis* f. sp. *tritici* that is known to cause wheat stem rust in a susceptible wheat plant.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

It is recognized that the R protein coding sequences of the present invention encompass polynucleotide molecules comprising a nucleotide sequence that is sufficiently identical to the nucleotide sequence of any one or more of SEQ ID NOS: 1, 8, 9, and 10. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 86%, 87%, 88%, 89%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *PNAS* 87:2264, modified as in Karlin and Altschul (1993) *PNAS* 90:5873-5877. Such an algorithm is incorporated into the NBLAST and XBLAST programs of Altschul et al. (1990) *J Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST; available on the world-wide web at ncbi.nlm.nih.gov). Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the world-wide web at: ebi.ac.uk/Tools/clustalw/index-.html).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide constructs comprising R protein coding regions can be provided in expression cassettes for expression in the plant or other organism or non-human host cell of interest. The cassette will include 5' and 3' regulatory sequences operably linked to the R protein coding region. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the R protein coding region to be under the transcriptional regulation of the regulatory regions. The expression cassette may additionally contain selectable marker genes.

The expression cassette will include in the 5'-3' direction of transcription, a transcriptional and translational initiation region (i.e., a promoter), a R protein coding region of the invention, and a transcriptional and translational termination region (i.e., termination region) functional in plants or other organism or non-human host cell. The regulatory regions (i.e., promoters, transcriptional regulatory regions, and translational termination regions) and/or the R protein coding region or of the invention may be native/analogous to the host cell or to each other. Alternatively, the regulatory regions and/or the R protein coding region of the invention may be heterologous to the host cell or to each other.

As used herein, "heterologous" in reference to a nucleic acid molecule or nucleotide sequence is a nucleic acid molecule or nucleotide sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The present invention provides host cells comprising at least one of the nucleic acid molecules, expression cassettes, and vectors of the present invention. In preferred embodiments of the invention, a host cell is a plant cell. In other embodiments, a host cell is selected from the group consisting of a bacterium, a fungal cell, and an animal cell. In certain embodiments, a host cell is a non-human animal cell. However, in some other embodiments, the host cell is an in-vitro cultured human cell.

While it may be optimal to express the R protein using heterologous promoters, the native promoter of the corresponding R gene may be used.

The termination region may be native with the transcriptional initiation region, may be native with the operably linked R protein coding region of interest, may be native with the plant host, or may be derived from another source (i.e., foreign or heterologous to the promoter, the R protein of interest, and/or the plant host), or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nuc. Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gown (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Virology 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the R protein coding sequences within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *PNAS* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant—Microbe Interactions* 2:325-331; Somsisch et al. (1986) *PNAS* 83:2427-2430; Somsisch et al. (1988) *Mol. Gen. Genet.* 2:93-98; and Yang (1996) *PNAS* 93:14972-14977. See also, Chen et al. (1996) *Plant J.* 10:955-966; Zhang et al. (1994) *PNAS* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Also of interest are the native promoters from other resistance genes from the target species. These promoters are often pathogen-inducible, and are likely to express the resistance gene at appropriate levels and in appropriate tissues. Examples of such promoters are the Sr57/Lr34, Sr33, Sr35, and Sr22 promoters of wheat (Risk et al. (2012) *Plant Biotechnol J.* 10: 447-487; Periyannan et al. (2013) *Science* 341: 786-788; Saintenac et al. (2013) *Science* 341: 783-786; Steuernagel et al. (2016) *Nature Biotechnol.* 34(6): 652-655, doi: 10.1038/nbt.3543).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *PNAS* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *PNAS* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *PNAS* 86:5400-5404; Fuerst et al. (1989) *PNAS* 86:2549-2553; Deuschle et al. (1990) *Science* 248:480-483; Gossen (1993) Ph.D. Thesis, University of Heidelberg; Reines et al. (1993) *PNAS* 90:1917-1921; Labow et al. (1990) *Mol. Cell. Biol.* 10:3343-3356; Zambretti et al. (1992) *PNAS* 89:3952-3956; Baim et al. (1991) *PNAS* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *PNAS* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not intended to be limiting. Any selectable marker gene can be used in the present invention.

Numerous plant transformation vectors and methods for transforming plants are available. See, for example, An et al. (1986) *Plant Physiol.,* 81:301-305; Fry et al. (1987) *Plant Cell Rep.* 6:321-325; Block (1988) *Theor. Appl. Genet.* 76:767-774; Hinchee et al. (1990) *Stadler Genet. Symp.* 203212.203-212; Cousins, et al. (1991) *Aust. J. Plant Physiol.* 18:481-494; Chee and Slightom (1992) *Gene.* 118: 255-260; Christou et al. (1992) *Trends Biotechnol.* 10:239-246; D'Halluin et al. (1992) *Bio/Technol.* 10:309-314; Dhir et al. (1992) *Plant Physiol.* 99:81-88; Casas et al. (1993) *PNAS* 90:11212-11216; Christou (1993) *In Vitro Cell. Dev. Biol.—Plant;* 29P:119-124; Davies et al. (1993) *Plant Cell Rep.* 12:180-183; Dongand Mchughen (1993) *Plant Sci.* 91:139-148; Franklin et al. (1993) *Plant Cell Rep.* 12(2): 74-79, doi: 10.1007/BF00241938; Golovkin et al. (1993) *Plant Sci.* 90:41-52; Asano et al. (1994) *Plant Cell Rep.* 13; Ayeres and Park (1994) *Crit. Rev. Plant Sci.* 13:219-239; Barcelo et al. (1994) *Plant J.* 5:583-592; Becker et al. (1994) *Plant J* 5:299-307; Borkowska et al. (1994) *Acta Physiol. Plant* 16:225-230; Christou (1994) *Agro. Food Ind. Hi Tech.* 5: 17-27; Eapen et al. (1994) *Plant Cell Rep.* 13:582-586; Hartman, et al. (1994) *Bio-Technology* 12: 919923; Ritala et al. (1994) *Plant Mol. Biol.* 24:317-325; and Wan and Lemaux (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.,* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *PNAS* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lecl transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *PNAS* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *PNAS* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

If desired, the modified viruses or modified viral nucleic acids can be prepared in formulations. Such formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al. Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, antifreezing agents, for seed treatment formulation also optionally colorants and/or binders and/or gelling agents.

In specific embodiments, the polynucleotide constructs and expression cassettes of the invention can be provided to a plant using a variety of transient transformation methods known in the art. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *PNAS Sci.* 91: 2176-2180 and Hush et al. (1994) *J. Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described elsewhere herein.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

Any methods known in the art for modifying DNA in the genome of a plant can be used to alter the coding sequences of an R gene in planta, e.g. to alter the nucleotide sequence of a homologous susceptible allele to that of an allele that provides resistance to at least one race of stem rust. Such methods include genome editing techniques, such as, for example, methods involving targeted mutagenesis, homologous recombination, and mutation breeding. Targeted mutagenesis or similar techniques are disclosed in U.S. Pat. Nos. 5,565,350; 5,731,181; 5,756,325; 5,760,012; 5,795,972, 5,871,984, and 8,106,259; all of which are herein incorporated in their entirety by reference. Methods for gene modification or gene replacement comprising homologous recombination can involve inducing double breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered endonucleases to make double-strand breaks at specific recognition sequences in the genome of a plant, other organism, or host cell. See, for example, Durai et al., (2005) *Nucleic Acids Res* 33:5978-90; Mani et al. (2005) *Biochem Biophys Res Comm* 335:447-57; U.S. Pat. Nos. 7,163,824, 7,001,768, and 6,453,242; Arnould et al. (2006) *J. Mol Biol* 355:443-58; Ashworth et al., (2006) *Nature* 441:656-9; Doyon et al. (2006) *J. Am Chem Soc* 128:2477-84; Rosen et al., (2006) *Nucleic Acids Res* 34:4791-800; and Smith et al., (2006) *Nucleic Acids Res* 34:e149; U.S. Pat. App. Pub. No. 2009/0133152; and U.S. Pat. App. Pub. No. 2007/0117128; all of which are herein incorporated in their entirety by reference.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze and Boch (2010) *Virulence* 1:428-432; Christian et al. *Genetics* (2010) 186: 757-761; Li et al. (2010) *Nuc. Acids Res.* (2010) doi: 10.1093/nar/gkq704; and Miller et al. (2011) *Nature Biotechnology* 29:143-148; all of which are herein incorporated by reference.

The CRISPR/Cas nuclease system can also be used to make double-strand breaks at specific recognition sequences in the genome of a plant for gene modification or gene replacement through homologous recombination. The CRISPR/Cas nuclease is an RNA-guided (simple guide RNA, sgRNA in short) DNA endonuclease system performing sequence-specific double-stranded breaks in a DNA segment homologous to the designed RNA. It is possible to design the specificity of the sequence (Cho et al. (2013) *Nat. Biotechnol.* 31:230-232; Cong et al. (2013) *Science* 339: 819-823; Mali et al. (2013) *Science* 339:823-826; Feng et al. (2013) *Cell Res.* 23(10):1229-1232).

In addition, a ZFN can be used to make double-strand breaks at specific recognition sequences in the genome of a plant for gene modification or gene replacement through homologous recombination. The Zinc Finger Nuclease (ZFN) is a fusion protein comprising the part of the FokI restriction endonuclease protein responsible for DNA cleavage and a zinc finger protein which recognizes specific, designed genomic sequences and cleaves the double-stranded DNA at those sequences, thereby producing free DNA ends (Urnov F. D. et al., *Nat Rev Genet.* 11:636-46, 2010; Carroll D., *Genetics.* 188:773-82, 2011).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions and other modifications.

The nucleic acid molecules, expression cassettes, vectors, and polynucleotide constructs of the present invention may be used for transformation of any plant species, including, but not limited to, monocots and dicots. Preferred plants of the present invention are wheat plants. Examples of other plant species of interest include, but are not limited to, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), *petunia* (*Petunia* spp., e.g., *Petunia*×*hybrida* or *Petunia hybrida*), pea (*Pisum sativum*), bean (*Phaseolus vulgaris*), corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), *citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), palms, oats, barley, vegetables, ornamentals, and conifers.

As used herein, the term "plant" includes plant cells, plant protoplasts, plant cell tissue cultures from which plants can be regenerated, plant calli, plant clumps, and plant cells that are intact in plants or parts of plants such as embryos, pollen, ovules, seeds, tubers, propagules, leaves, flowers, branches, fruits, roots, root tips, anthers, and the like. Progeny, variants, and mutants of the regenerated plants are also included within the scope of the invention, provided that these parts comprise the introduced polynucleotides. As used herein, "progeny" and "progeny plant" comprise any subsequent generation of a plant whether resulting from sexual reproduction and/or asexual propagation, unless it is expressly stated otherwise or is apparent from the context of usage.

In some embodiments of the present invention, a plant cell is transformed with a polynucleotide construct encoding an R protein of the present invention. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Examples of polynucleotide constructs and nucleic acid molecules that encode R proteins are described elsewhere herein.

The use of the terms "DNA" or "RNA" herein is not intended to limit the present invention to polynucleotide molecules comprising DNA or RNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like. Furthermore, it is understood by those of ordinary skill in the art that the nucleotide sequences disclosed herein also encompasses the complement of that exemplified nucleotide sequence.

The invention is drawn to compositions and methods for enhancing the resistance of a plant to plant disease, particularly to compositions and methods for enhancing the resistance of a wheat plant to wheat stem rust. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

The present invention encompasses the nucleic acid molecules and polynucleotide constructs disclosed herein or in the accompanying sequence listing and/or drawings including, but not limited to: nucleic acid molecules and polynucleotide constructs comprising the nucleotide sequences set forth in SEQ ID NOS: 1, 8, 9, and/or 10; and nucleic acid molecules and polynucleotide constructs encoding a protein comprising the amino acid sequence set forth in SEQ ID NO: 11. The present invention further encompasses plants, plant cells, host cells, and vectors comprising at least one of such nucleic acid molecules and/or polynucleotide constructs, as well as food products produced from such plants. Additionally encompassed by the present invention are uses of plants comprising at least one of such polynucleotide constructs in the methods disclosed elsewhere herein such as, for example, methods for enhancing the resistance of a wheat plant to wheat stem rust and methods of limiting wheat stem rust in agricultural crop production.

The following examples are offered by way of illustration and not by way of limitation.

EXAMPLES

Example 1: Isolation of a Candidate Sequence for SrTA1662

Most resistance (R) genes encode nucleotide binding and leucine-rich repeat (NLR) immune receptors (Jones and Dangl (2006) *Nature* 444:323-329). We used NLR resistance gene enrichment sequencing (RenSeq) (Jupe et al. (2013) *Plant J.* 76:530-544), to sequence the NLRs in a panel of 151 geographically and genetically diverse *Ae. tauschii* accessions, the diploid D genome progenitor of hexaploid bread wheat.

Figure 2:
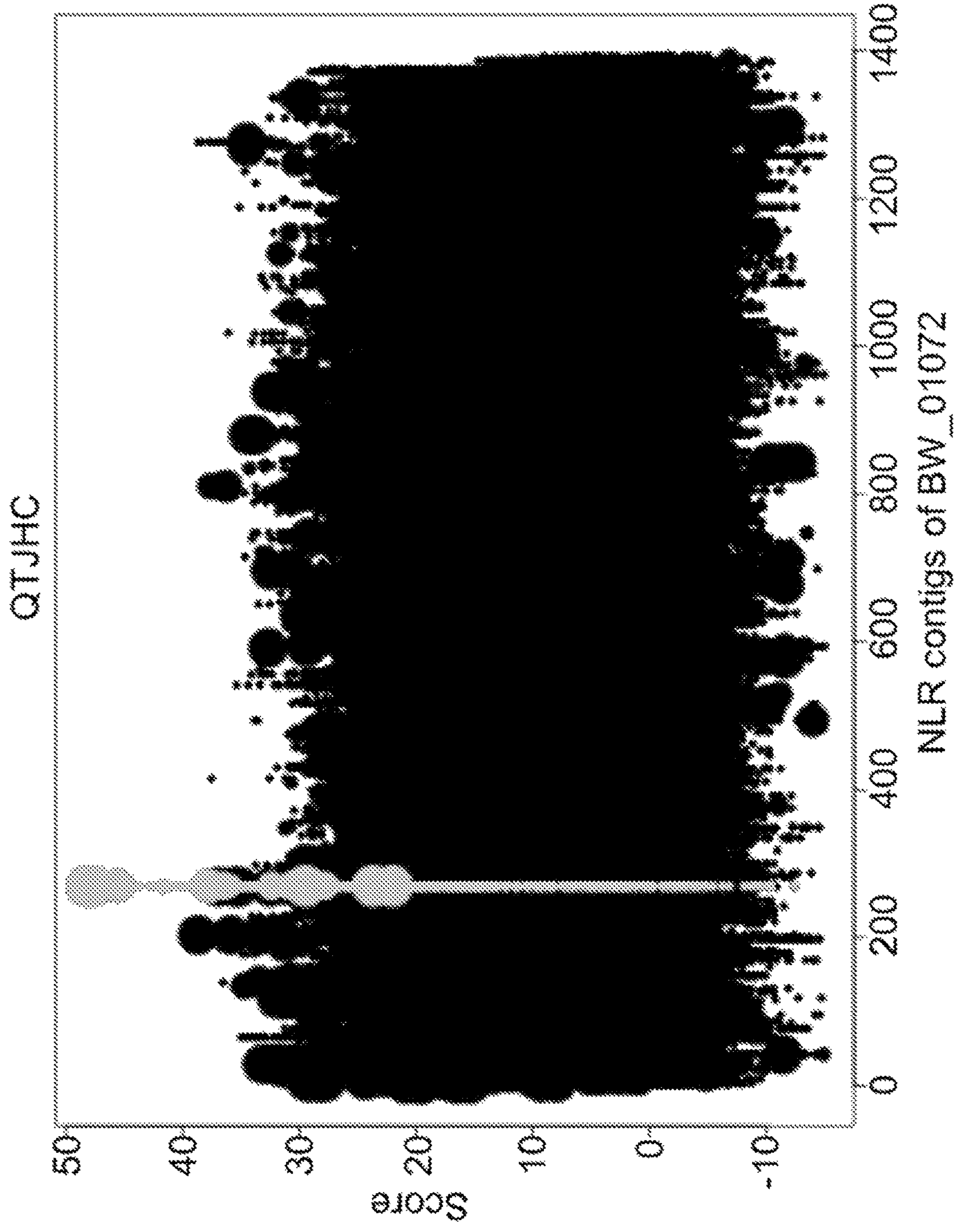
FIG. 2 illustrates the identification of SrTA1662 by association genetics coupled to RenSeq. Each integer on the x-axis represents an NLR contig from the RenSeq assembly of the accession BW_01072 which contains the resistance gene SrTA1662. Each dot on the y-axis represents one or more RenSeq k-mers associated with resistance across the diversity panel to the PGT race QTHJC. Dot size is proportional to the number of k-mers associated with resistance. K-mers associated with the SrTA1662 candidate gene are shown in grey.

We phenotyped the diversity panel with the fungal wheat pathogen *Puccinia graminis* f. sp. *tritici* (PGT) the causal agent of wheat stem rust, using the North American race QTHJC (FIG. 1). We then correlated the infection type phenotypes with the RenSeq genotypes to identify candidate NLRs associated with stem rust resistance. We identified a single discrete peak of association in a 7.64 kb RenSeq contig (FIG. 2; SEQ ID NO: 1). We aligned this candidate Sr gene to the reference genome assembly of wheat cv. Chinese Spring RefSeq1.0 (www.wheatgenome.org). The candidate Sr gene coincided with the known genetic position of SrTA1662, a Sr gene previously introgressed into wheat from *Ae. tauchii* ssp. *strangulata* (Olson et al. (2013) *Theor. Appl. Genet.* 126:1179-1188). The SrTA1662 candidate encodes a coiled-coil NLR with 85% identity to the previously cloned Sr33 gene (Periyannan et al. (2013) *Science* 341:786-788).

Example 2: Creation of a Construct Encoding the SrTA1662 Candidate Gene

To validate the disease resistance function of the candidate SrTA1662 gene sequence, we generated a binary vector transformation construct containing an SrTA1662 expression cassette constructed using the Golden Gate Modular Cloning Tool Kit for Plants (Engler et al. (2014) *ACS Synth. Biol.* 3:839-843). The Sr33 promoter and Sr33 terminator (Periyannan et al. (2013) *Science* 341:786-788) was used to regulate expression of the SrTA1662 genomic sequence from the predicted start codon to the predicted stop codon (SEQ ID NO: 1). Synthetic DNA fragments of these three sequences were obtained from a commercial provider each flanked by a pair of divergent BsaI recognition sites for Golden Gate Cloning and four base pair standard fusion sites for TypeIIS assembly defined in the Plant Common Genetic Syntax (Patron et al. (2015) *New Phytol.* 208:13-19). The native SrTA1662 nucleotide sequence was domesticated by removing four BsaI sites with silent point mutations. The synthetic parts were assembled into the pICH47732 Level one acceptor (Weber et al. (2011) *PLoS One* 6:e16765) and then the gene cassette was cloned into the Notl site of the pVec8 binary vector to give rise to pBW_0150 (SEQ ID NO: 5).

The open reading frame comprising the domesticated SrTA1662 nucleotide sequence is provided in SEQ ID NO: 6, and the amino acid sequence of the R protein encoded thereby is provided in SEQ ID NO: 7. It is noted that amino acid sequence of SEQ ID NO: 7 comprises the amino acid sequence that is set forth in SEQ ID NO: 4 and an additional methionine (M) operably linked to the N-terminal end of the amino acid sequence of SRTA1662. The additional of a single methionine at N-terminal end of the amino acid sequence of SRTA1662 is not expected to have any significant effect on the function of the resulting R protein, relative to the function of native or wild-type SRTA1662.

Example 3: Transformation of Wheat with SrTA1662

To confirm the ability of the SrTA1662 expression construct pBW_0150 (SEQ ID NO: 5) to confer stem rust resistance, we transformed the construct into hexaploid wheat cultivars Fielder and Westonia using established *Agrobacterium*-mediated transformation procedures as described in WO 2017/024053, herein incorporated by reference.

Example 4: Testing of the Resistance of SrTA1662 Against Various PGT Isolates To study the specificity of SrTA1662 against a range of PGT isolates, we infected a subset of *Ae. tauschii* accessions predicted to carry only SrTA1662 out of the four Sr genes described from *Ae. tauschii* ssp. *strangulata*, namely Sr33, Sr45, Sr46 and SrTA1662. Accessions carrying SrTA1662 only were susceptible (infection types 3 to 4) to the Australian pathotype LTBJC (isolate 98-1,2,3,5 and 6) the North American pathotypes RKQQC (isolate 99KS76A), TTTTF (isolate 02MN84a-1-2) and TPMKC (isolate 74MN1409), the Yemeni pathotype TRTTF (isolate 06YEM34-1) and Kenyan pathotype TTKSK (isolate 04KEN156/04). However, they were clearly resistant to the North American pathotypes QTHJC (isolate 75ND717C; infection types 0; to 1) and MCCFC (isolate A-5; infection type 0; to 22-), and the UK pathotype TKTTF (isolate UK-01; infection type 1-). Since we have established that UK-01 is virulent on cv. Fielder, we will in the first instance use this isolate to screen the SrTA1662 primary transgenic plants (Lewis et al. (2018) *Commun. Biol.* 1:13, doi: 10.1038/s42003-018-0013-y).

Example 5: Construction of a Full-Length SrTA1662 Gene

To examine the function of the SrTA1662 candidate, we initially transformed *Triticum aestivum* cultivar Fielder with a construct (SEQ ID NO: 5) containing 3,930 bp of the SrTA1662 candidate gene form the predicted start codon, preceded by the Sr33 promoter (Periyannan et al. (2013) *Science* 341:786-788) and followed by the Sr33 terminator (Periyannan et al. (2013) *Science* 341:786-788). This construct provided at best a very weak resistance response to *Puccinia graminis* f. sp. *graminis* isolate UK-01 (the plants turned susceptible after a window of 4-5 days compared to controls). We subsequently extended the length of the native genomic sequence of the SrTA1662 candidate gene locus by mining whole genome shotgun assemblies of *Aegilops tauschii* accessions BW_01106 and BW_01049 to obtain a 10,445 bp contiguous sequence. This sequence was confirmed by PCR on genomic DNA of *Ae. tauschii* accession 1662 followed by Sanger sequencing. The transcriptional unit of SrTA1662 was then defined by aligning 26 Gb (after data trimming) total leaf transcriptome data of accession BW_01106 to the 10,445 bp contiguous sequence described above. This revealed an additional 3' terminal exon (Exon 3) and an additional intron that had been missing in the first construct of the SrTA1662 gene (SEQ ID NO: 2) which has only two exons. We therefore synthesised a new full-length, native SrTA1662 construct (10,445 bp; SEQ ID NO: 8) containing 3,395 bp before the predicted translational start site and 3,024 bp after the predicted stop codon. Although the full-length, native SrTA1662 gene construct (SEQ ID NO: 8) is longer (10,445 bp) and has one additional exon relative to the first SrTA1662 gene construct (9, 967 bp; SEQ ID NO: 2) the full-length, native SrTA1662 gene construct encodes a protein having 12 fewer amino acids (958 amino acid; SEQ ID NO:11) than the protein predicted to be encoded by the first SrTA1662 gene construct (970 amino acids; SEQ ID NO: 4) because Exon 2 is smaller in the full-length, native SrTA1662 gene construct than in the initial gene construct.

This sequence of the full-length, native SrTA1662 gene (SEQ ID NO: 8) was cloned into the binary vector pGGG (Dolores-Rey et al. (2018) *Plant Sci.* 9: 509) and transformed into *T. aestivum* cultivar Fielder.

Example 6: Scoring Transgenic Wheat Plants for Resistance to Stem Rust

Hexaploid wheat cultivars Fielder and Westonia were transformed essentially as described in Example 3 with the full-length, native SrTA1662 gene (SEQ ID NO: 8) cloned into the binary vector pGGG (see Example 5). Transgenic seedling explants were tested with PGT races predicted to be avirulent on transgenic wheat plants comprising SrTA 1662 (see Example 4) and virulent on cv. Fielder or cv. Westonia wheat plants using established procedures as described in WO 2017/024053. Briefly, transgenic explants were removed from tissue culture and transplanted to soil and allowed to acclimatize. Subsequently, the resulting transgenic plants were inoculated with spores of PGT UK-01. Symptom development (infection type scores) was evaluated at 11 days post inoculation. Of 49 TO plants, 9 were resistant, 2 were moderately resistant, and 38 were susceptible. These results indicate that the SrTA 1662 gene having the nucleotide sequence set forth in SEQ ID NO: 8 is an R gene.

The article “a” and “an” are used herein to refer to one or more than one (i.e., to at least one) of the grammatical object of the article. By way of example, “an element” means one or more element.

Throughout the specification the word “comprising,” or variations such as “comprises” or “comprising,” will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression cassette comprising a heterologous promoter operably linked to a nucleic acid molecule, or a vector comprising the nucleic acid molecule or the expression cassette, wherein the nucleic acid molecule comprises a nucleotide sequence selected from the group consisting of:

(a) the nucleotide sequence set forth in SEQ ID NO: 1, 8, 9, or 10;

(b) a nucleotide sequence encoding the amino acid sequence set forth in SEQ ID NO: 11;

(c) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and (d) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid.

2. A host cell transformed with (a) an expression cassette comprising a heterologous promoter operably linked to a nucleic acid molecule, (b) a vector comprising the nucleic acid molecule or the expression cassette, or (c) the nucleic acid molecule, wherein the nucleic acid molecule comprises a nucleotide sequence selected from the group consisting of:

(i) the nucleotide sequence set forth in SEQ ID NO: 1, 8, 9, or 10;

(ii) a nucleotide sequence encoding the amino acid sequence set forth in SEQ ID NO: 11;

(iii) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and (iv) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid.

3. A transgenic plant or seed comprising stably incorporated in its genome a heterologous polynucleotide comprising a nucleotide sequence selected from the group consisting of:
(a) the nucleotide sequence set forth in SEQ ID NO: 1, 8, 9, or 10;
(b) a nucleotide sequence encoding the amino acid sequence set forth in SEQ ID NO: 11;
(c) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and
(d) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid molecule.

4. The transgenic plant or seed of claim 3, wherein the heterologous polynucleotide further comprises a promoter operably linked for the expression of the nucleotide sequence in a plant.

5. The transgenic plant or seed of claim 4, wherein the promoter is selected from the group consisting of pathogen-inducible, constitutive, tissue-preferred, wound-inducible, and chemical-regulated promoters.

6. The transgenic plant or seed of claim 3, wherein the transgenic plant is a wheat plant and the transgenic seed is a wheat seed.

7. A method for enhancing the resistance of a wheat plant to wheat stem rust, the method comprising introducing a polynucleotide construct into at least one wheat plant cell, the polynucleotide construct comprising (a) an expression cassette comprising a heterologous promoter operably linked to a nucleic acid molecule, (b) a vector comprising the nucleic acid molecule or the expression cassette, or (c) the nucleic acid molecule, wherein the nucleic acid molecule comprises a nucleotide sequence selected from the group consisting of:
(i) the nucleotide sequence set forth in SEQ ID NO: 1, 8, 9, or 10;
(ii) a nucleotide sequence encoding the amino acid sequence set forth in SEQ ID NO: 11;
(iii) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and
(iv) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid.

8. A wheat plant produced by a method comprising introducing a polynucleotide construct into at least one wheat plant cell, the polynucleotide construct comprising (a) an expression cassette comprising a heterologous promoter operably linked to a nucleic acid molecule, (b) a vector comprising the nucleic acid molecule or the expression cassette, or (c) the nucleic acid molecule, wherein the nucleic acid molecule comprises a nucleotide sequence selected from the group consisting of:
(i) the nucleotide sequence set forth in SEQ ID NO: 1, 8, 9, or 10;
(ii) a nucleotide sequence encoding the amino acid sequence set forth in SEQ ID NO: 11;
(iii) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and
(iv) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid.

9. A seed of the wheat plant of claim 8, wherein the seed comprises the polynucleotide construct.

10. A method of limiting wheat stem rust in agricultural crop production, the method comprising planting a transgenic wheat seed and growing from the transgenic wheat seed a wheat plant under conditions favorable for the growth and development of the wheat plant, wherein the transgenic wheat seed comprises stably incorporated in its genome a heterologous polynucleotide comprising a nucleotide sequence selected from the group consisting of:
(a) the nucleotide sequence set forth in SEQ ID NO: 1, 8, 9, or 10;
(b) a nucleotide sequence encoding the amino acid sequence set forth in SEQ ID NO: 11;
(c) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and
(d) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid molecule.

11. The method of claim 10, further comprising harvesting at least one seed from the wheat plant.

12. A human or animal food product produced using a transgenic wheat plant or wheat seed comprising stably incorporated in its genome a heterologous polynucleotide comprising a nucleotide sequence selected from the group consisting of:
(a) the nucleotide sequence set forth in SEQ ID NO: 1, 8, 9, or 10;
(b) a nucleotide sequence encoding the amino acid sequence set forth in SEQ ID NO: 11;
(c) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and
(d) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid molecule.

13. A method for identifying a wheat plant that displays newly conferred or enhanced resistance to wheat stem rust, the method comprising detecting in the wheat plant the presence of the R gene, SrTA1662, wherein SrTA1662 comprises a nucleotide sequence selected from the group consisting of:

(a) the nucleotide sequence set forth in SEQ ID NO: 1, 8, 9, or 10;

(b) a nucleotide sequence encoding the amino acid sequence set forth in SEQ ID NO: 11;

(c) a nucleotide sequence having at least 95% sequence identity to at least one of the nucleotide sequences set forth in SEQ ID NOS: 1 and 8, wherein the nucleic acid molecule is capable of conferring resistance to stem rust to a wheat plant comprising the nucleic acid molecule; and (d) a nucleic acid molecule comprising a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid molecule.

14. The method of claim 13, wherein the presence of the R gene is detected by detecting at least one marker within SrTA1662.

15. The method of claim 13, wherein SrTA1662 comprises or consists of, the nucleotide sequence set forth in SEQ ID NO: 1, 8, 9, or 10, or a nucleotide sequence encoding SEQ ID NO: 11.

16. The expression cassette of claim 1, wherein the nucleic acid molecule comprises a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid molecule.

17. The expression cassette of claim 1, wherein the nucleic acid molecule comprises a nucleotide sequence encoding an amino acid sequence having at least 99% sequence identity to the amino acid sequence set forth in SEQ ID NO: 11, wherein the nucleic acid molecule is capable of conferring resistance to stem rust to a wheat plant comprising the nucleic acid molecule.

18. The transgenic plant or seed of claim 3, wherein the nucleic acid molecule comprises a nucleotide sequence encoding an amino acid sequence having at least 98% sequence identity to the amino acid sequence set forth in SEQ ID NO: 11, wherein the nucleic acid molecule is capable of conferring resistance to stem rust to a wheat plant comprising the nucleic acid molecule.

19. The transgenic plant or seed of claim 3, wherein the nucleic acid molecule comprises a nucleotide sequence encoding an amino acid sequence having at least 99% sequence identity to the amino acid sequence set forth in SEQ ID NO: 11, wherein the nucleic acid molecule is capable of conferring resistance to stem rust to a wheat plant comprising the nucleic acid molecule.

* * * * *